United States Patent
Song et al.

(10) Patent No.: US 9,017,726 B2
(45) Date of Patent: Apr. 28, 2015

(54) BIODEGRADABLE AND THERMOSENSITIVE POLY(ORGANOPHOSPHAZENE)-SUPERPARAMAGNETIC NANOPARTICLE COMPLEX, PREPARATION METHOD AND USE THEREOF

(75) Inventors: Soo-Chang Song, Seoul (KR); Jang Il Kim, Seongnam-si (KR)

(73) Assignee: Korea Institute of Science and Technology, Seoul (KR)

( * ) Notice: Subject to any disclaimer, the term of this patent is extended or adjusted under 35 U.S.C. 154(b) by 755 days.

(21) Appl. No.: 13/173,756

(22) Filed: Jun. 30, 2011

(65) Prior Publication Data
US 2012/0121517 A1 May 17, 2012

(30) Foreign Application Priority Data

Jun. 30, 2010 (KR) .................. 10-2010-0062850

(51) Int. Cl.
| | |
|---|---|
| *A61K 9/14* | (2006.01) |
| *B82Y 5/00* | (2011.01) |
| *A61K 9/00* | (2006.01) |
| *A61K 49/18* | (2006.01) |
| *B82Y 15/00* | (2011.01) |
| *C08G 79/02* | (2006.01) |
| *C08L 85/02* | (2006.01) |

(52) U.S. Cl.
CPC .............. *B82Y 5/00* (2013.01); *A61K 9/0009* (2013.01); *A61K 49/1857* (2013.01); *B82Y 15/00* (2013.01); *C08G 79/025* (2013.01); *C08L 85/02* (2013.01)

(58) Field of Classification Search
None
See application file for complete search history.

(56) References Cited

FOREIGN PATENT DOCUMENTS

| JP | 62-9519 | 1/1987 |
|---|---|---|
| JP | 2002-80715 | 3/2002 |
| KR | 10-2004-0105357 | 12/2004 |

OTHER PUBLICATIONS

Machine translation of JP 2002-080714 to Urabe Hiroshi, 2014.*

* cited by examiner

*Primary Examiner* — Paul Dickinson
(74) *Attorney, Agent, or Firm* — Staas & Halsey LLP

(57) ABSTRACT

The present invention relates to a poly(organophosphazene)-superparamagnetic nanoparticle complex including a biodegradable and thermosensitive poly(organophosphazene) and a iron oxide ($Fe_3O_4$, Magnetite)-series ferrite superparamagnetic nanoparticle, a preparation method, and uses of carrying a physiologically-active material, a bio-material and a bio-material for cancer hyperthermia. The iron oxide is used as a MRI contrast agent for $T_{-2}$ and $T_2{}^*$ weighted image, and the poly(organophosphazene) shows a sol-to-gel behavior depending upon the temperature change. The complex is a bound-type where the superparamagnetic ferrite nanoparticle is bonded to phosphazene-based polymer via hydrophobic binding, and a mixed-type where the superparamagnetic ferrite nanoparticle is physically mixed with the phosphazene-based polymer.

30 Claims, 15 Drawing Sheets

BIODEGRADABLE AND THERMOSENSITIVE POLY(ORGANOPHOSPHAZENE)-SUPERPARAMAGNETIC NANOPARTICLE COMPLEX, PREPARATION METHOD AND USE THEREOF

CROSS-REFERENCE TO RELATED APPLICATION

This application claims priority to and the benefit of Korean Patent Application No. 10-2010-0062850 filed in the Korean Intellectual Property Office on Jun. 30, 2010, the entire contents of which are incorporated herein by reference.

BACKGROUND OF THE INVENTION (a) Field of the Invention

The present invention relates to a poly(organophosphazene)-superparamagnetic nanoparticle complex including a thermosensitive/biodegradable poly(organophosphazene) and a iron oxide ($Fe_3O_4$, Magnetite)-series ferrite superparamagnetic nanoparticle, a preparation method, and uses of carrying a physiologically-active material, biomaterial and a MRI contrast agent. The above phosphazene polymer has reversible sol-to-gel phase transition, biodegradability, and thermosensitivity, and includes a chemical bond formed by at least one method selected from UV radiation, cross-linking agent treatment, additive treatment, enzyme treatment and the addition of at least a polymer.

(b) Description of the Related Art

The phase of thermosensitive hydrogel is sol at low temperature and turns into gel as the temperature increases. The sol-to-gel phase transition can be observed reversibly. Because the thermosensitive hydrogel is in an aqueous polymer solution at room temperature, it can be easily mixed with a therapeutic drug. In addition, if the thermosensitive hydrogel is injected into a needed region without surgical treatment, it forms a three dimensional structure with the body heat and thus is capable of releasing a drug slowly. Thus, the thermosensitive hydrogel has been evaluated highly as an injectable carrier material for drug delivery.

When the thermosensitive hydrogel is used as injectable carrier material, a drug with a low weight-average molecular weight or high hydrophilicity is injected into a body with the polymer carrier, and can be released easily through the three dimensional network structure of gel. 30% or more of the loaded drugs are released at the early stage and the release of drug completes in a short time due to the high diffusion rate of hydrophilic drug (Adv. Drug Deliv. Rev., 31, 197 (1998)).

To remedy the problem, the thermosensitive hydrogel of which a functional group is able to conjugate directly with a drug was introduced. When the thermosensitive polymer conjugated chemically with a hydrophilic drug is injected into a body, the drug can be sustainedly released by degrading tendency of the polymer or the chemical bond between the polymer and drug. The sustained release of drug and the degradation of thermosensitive hydrogel were proven by in vitro experiment. In in vivo experiment, however, there has not been noninvasive method to monitor the behavior of polymer within a body including the degrading tendency of the polymer injected into a body.

The present inventors substituted the dichlorophosphazene linear polymer with amino acid ester and methoxypolyethylene glycol, found that the substituted phosphazene polymer showed a sol-to-gel phase transition where the polymer was in an aqueous solution under the certain temperature but turned into a three-dimensional structural gel above a certain temperature, and reported that the thermosensitive phosphazene polymer was hydrolyzed slowly in an aqueous solution (Macromolecules 32, 2188 (1999), Macromolecules 32, 7820 (1999), Macromolecules 35, 3876 (2002), KR patent no. 10-0259367, KR patent no. 10-0315630, and U.S. Pat. No. 6,319,984).

SUMMARY OF THE INVENTION

The present inventors found the various uses of poly(organophosphazene)-superparamagnetic nanoparticle complex including a biodegradable and thermosensitive phosphazene-based polymer and a superparamagnetic ferrite nanoparticle and completed the present invention.

An embodiment of the present invention is to provide a poly(organophosphazene)-superparamagnetic nanoparticle complex including a biodegradable and thermosensitive poly (organophosphazene) and iron oxide ($Fe_3O_4$, Magnetite)-based ferrite superparamagnetic nanoparticle.

An embodiment of the present invention is to provide a preparation method of poly(organophosphazene)-superparamagnetic nanoparticle complex.

An embodiment of the present invention provides a composition for carrying a physiologically-active material, comprising the poly(organophosphazene)-superparamagnetic nanoparticle complex.

Another embodiment of the present invention provides a bioactive-substance carrier comprising the poly(organophosphazene)-superparamagnetic nanoparticle complex.

Further embodiment of the present invention is to provide a bioactive-substance carrier, comprising the poly(organophosphazene)-superparamagnetic nanoparticle complex and a physiologically-active material.

Still further embodiment of the present invention provides a bio-material comprising the poly(organophosphazene)-superparamagnetic nanoparticle complex.

Further embodiment of the present invention is to provide a contrast agent for magnetic resonance image (MRI) comprising the poly(organophosphazene)-superparamagnetic nanoparticle complex.

DETAILED DESCRIPTION OF THE EMBODIMENTS

The present invention employs a biodegradable and thermosensitive phosphazene-based polymer showing a sol-to-gel behavior depending upon the temperature change, and the phosphazene-based polymer may include as follows:

① a phosphazene-based polymer;
② a phosphazene-based polymer having a functional group;
③ a phosphazene-based polymer bound covalently with a physiologically-active material;
④ a phosphazene-based polymer being capable of crosslinking chemically;
⑤ a phosphazene-based polymer being capable of crosslinking chemically and having a functional group; and/or
⑥ a phosphazene-based polymer bound covalently with a physiologically-active material which is capable of crosslinking chemically.

The present invention relates to a poly(organophosphazene)-superparamagnetic nanoparticle complex including a biodegradable and thermosensitive phosphazene-based polymers of ①~⑥ and a iron oxide ($Fe_3O_4$, Magnetite)-series ferrite superparamagnetic nanoparticle which is used as a MRI contrast agent for $T_{-2}$ and $T_2^*$ weighted image, and uses thereof.

The poly(orgnaophosphazene)-superparamagnetic nanoparticle complex is a mixed-type where phosphazene-based polymer and superparamagnetic nanoparticle are physically mixed or a bound-type where phosphazene-based polymer and superparamgnetic nanoparticle are chemically bound. That is, the complex is formed in a bound-type complex that the phosphazene-based polymer and superparamagnetic nanoparticle are bound through hydrophobic interaction or mixed-type complex that the phosphazene-based polymer and superparamagnetic nanoparticle are simply mixed. Hereinafter, the bound-type poly(organophosphazene)-superparamagnetic nanoparticle complex, and the phosphazene-based bound-type magnetic polymer (or 'bound-type complex') are used as the same meaning, and the mixed-type poly(organophosphazene)-superparamagnetic nanoparticle complex, and the phosphazene-based mixed-type magnetic polymer (or 'mixed-type complex') are used as the same meaning.

In the bound-type complex, the superparamagnetic ferrite nanoparticle includes a hydrophobic surfactant on its surface selected from the group consisting of cis-9-Octadecenoic acid ($CH_3(CH_2)_7CH=CH(CH_2)_7COOH$) and cis-1-Amino-9-octadecene ($CH_3(CH_2)_7CH=CH(CH_2)_7CH_2NH_2$)), and the hydrophobic surfactant can bind chemically via hydrophobic interaction to the ester of hydrophobic amino acid of the phosphazene-based polymer.

The mixed-type complex can be formed by modifying the hydrophobic surface of superparamagnetic ferrite nanoparticle into hydrophilic surface and then mixing physically.

Because the poly(organophosphazene)-superparamagnetic nanoparticle complex has thermosensitive property showing a reversible sol-to-gel behavior depending upon the temperature change, like phosphazene-based polymer of ①~⑥, the complex injected into a body becomes a gel due to the body heat. Thus, the use of the complex makes the release of physiologically-active material controllable easily. Since the complex includes a functional group being capable of forming the chemical bonds such as ionic bond, covalent bond, and coordination bond with drugs, it has an excellent drug loading property. The complex can release a drug slowly, and thus can be useful for carrying a physiologically-active material such as drugs. In addition, the change and dissolution tendency of the magnetic polymer injected to the body and subsequent release tendency of the physiologically-active material can be monitored and/or analyzed quantitatively by using MRI which is non-invasive and has the highest resolution among the currently-used many clinical imaging modalities.

In the present invention, a poly(organophosphazene)-superparamagnetic nanoparticle complex or a hydrogel including the complex can be provided. The iron oxide ($Fe_3O_4$, Magnetite)-series ferrite superparamagnetic nanoparticle which is used as a MRI contrast agent for $T_{-2}$ and $T_2^*$ weighted image is simply mixed physically or bound chemically throught hydrophobic interaction. After the poly(organophosphazene)-superparamagnetic nanoparticle complex and/or the hydrogel including the complex is injected into a body, the pharmacokinetic behavior of hydrogel and subsequent sustained release trend of drugs can be monitored in real time outside the body, by using MRI which is non-invasive and has the highest resolution in the currently-used many clinical imaging modalities.

The poly(organophosphazene)-superparamagnetic nanoparticle complex and/or the hydrogel including the complex can be used for cancer hyperthermia through high frequency magnetic field. In addition, they can be used as a MRI contrast agent to detect specific lesion, because the material to be targeted is chemically bonded to the phosphazene-based magnetic polymer and is able to be injected into a body with a solution form by adjusting the sol-to-gel transition temperature.

Meanwhile, because the poly(organophosphazene)-superparamagnetic nanoparticle complex includes a superparamagnetic nanoparticle, it can transform the magnetic moment or magnetization driven by high frequency magnetic field into heat energy inside the magnetic polymer. The mechanism of transforming into the heat energy has been known well as brownian relaxation or Neel's relaxation on a magnetic nanoparticle having a diameter of 100 nm or smaller (Journal of physics: Condensed Matter 18 (2006) S2919-S2934). Thus, the magnetic polymer and the magnetic hydrogel can be optimized and applied to hyperthermia.

The present inventors disclosed a biodegradable and thermosensitive phosphazene-based polymer showing a sol-to-gel behavior depending upon the temperature change and including a functional group, and a hydrogel including a solution of phosphazene-based polymer in Korean Patent application No. 10-2006-0107230, PCT international application No. PCT/KR2006/004573, and Korean patent application No. 10-2008-0040413, wherein the documents are enclosed herewith as a reference.

Hereinafter, the term 'biodegradability' or 'biodegradable' means a property of material which is harmless to the tissue and is not left by being degraded into harmless material and released from body, when it is injected into a body. The term 'thermosensitivity' or 'thermosensitive' means a property showing a sol-to-gel behavior that sol is changed into gel depending upon the temperature increase. The temperature where the sol-to-gel behavior appears is referred to 'gelation temperature.'=The term 'magnetism' means the magnetic property of superparamagnetic nanoparticle that interacts with high frequency magnetic field at MRI shooting, and refers to a magnetic property of magnetic polymer. The term 'bound-type' means a form of the complex where the superparamagnetic nanoparticle is bound chemically with the phosphazene-based polymer via hydrophobic interaction and the term 'mixed-type' means a form of the complex where the superparamagnetic nanoparticle with hydrophilic surface is mixed physically with the phosphazene-based polymer.

The present invention will be described in more detail hereinafter.

The supermagnetic ferrite nanoparticle useful for the present invention has an inverse spinel structure as represented in FIG. 2. In FIG. 2, magnetite nanoparticle forms a crystal of oxygen and iron atoms, the oxygen atoms form a closed-packing face-centered cubic structure, ferrous ion (2+) and ferric ion (3+) are located on the tetrahedral site or octahedral site.

$$Fe^{3+,T}(Fe^{2+},Fe^{3+})^OO_4^{2-} \qquad \text{[Chemical formula 2a]}$$

Where ferrous ion (2+) located on octahedral cubic can be replaced with other transition metal on the same period of iron in the periodic table and forms the following crystal structural formula (Chem. Eng. J., 129, 51(2007)).

$$Fe^{3+,T}(Me^{2+},Fe^{3+})^OO_4^{2-} \qquad \text{[Chemical formula 2b]}$$

$$Me_{1-\delta}^{2+}Fe_\delta^{3+,T}(Me_\delta^{2+}Fe_{2-\delta}^{3+})^OO_4^{2-} \qquad \text{[Chemical formula 2c]}$$

Where Me is a transition metal on the same column period of iron in the periodic table, for examples, at least one selected from the group consisting of Sc, Ti, V, Cr, Mn, Co, Ni, Cu and Zn, T is Tetrahedral site, O is Octahedral site, and δ is a transformation rate ranging from 0 to 1.

The preparation method of superparamagnetic nanoparticle useful for the present invention can be any generally-known method without limitation.

For example, in case that the nanoparticle is prepared by thermal decomposition method (J. Am. Chem. Soc., 124, 8204(2002), J. Am. Chem. Soc., 126, 273(2004), J. Am. Chem. Soc., 126, 6164(2004), Small, 1, 48(2005), Langmuir, 15, 8633(1999)), the final product includes hydrophobic surfactants such as oleic acid (cis-9-Octadecenoic acid, $CH_3$ $(CH_2)_7CH=CH(CH_2)_7COOH$) and/or oleylamide (cis-1-Amino-9-octadecene, $CH_3(CH_2)_7CH=CH(CH_2)_7CH_2NH_2$) on the surface of nanoparticle, thereby making all superparamagnetic nanoparticles have the hydrophobic surfaces. By using the thermal decomposition method, the nanoparticle with the homogeneous particle size can be obtained advantageously. In addition, the nanoparticle has the hydrophobic surface and thus can form the chemical bond by interacting hydrophobically with the hydrophobic amino acid of the phosphozene-based polymer.

The hydrophobic surface of superparamagnetic nanoparticle can interact hydrophobically with and bind to hydrophobic amino acid ester ($NHCH(R^1)CO_2R_2$) of the phosphozene-based polymer as represented by Chemical formulae 1a, 1b and 1c. The phosphazene-based polymer can interact hydrophobically with and chemically bind to superparamagnetic nanoparticle, so as to form 'bound-type' complex. Thus, the complex can have original physicochemical properties such as biocompatibility and thermosenstivity of phosphazene-based polymer which does not interact with superparamagnetic nanoparticle itself. Moreover, because the thermosensitive phosphazene-based polymer has an excellent biocompatibility, the superparamagnetic nanoparticle having the hydrophobic surface surrounded by the phosphazene-based polymer does not show in vivo toxicity Meanwhile, in case that the superparamagnetic nanoparticle is prepared by the surface ligand exchange method (Langmuir, 15, 8633(1999)), so as to have a modified hydrophilic surface, the nanoparticle can form a complex by simple mixing with the phosphazene-based polymer to produce 'mixed-type' poly(organophosphazene)-superparamagnetic nanoparticle complex. If the materials used in the surface ligand exchange method are biocompatible, the complex does not show in vivo toxicity. The useful materials for modifying to hydrophilic surface may include Polyethylene Glycol (PEG)-based compounds. PEG-based compounds including a modified one end by amination or carboxylation, such as $NH_2$-PEG-$CH_3$ or COOH-PEG-$CH_3$ are more preferable, compared to the compound including —OH groups on both terminals. The weight-average molecular weight of PEG-based compounds is preferably 350 Da to 10,000 Da, but not limited thereto. Amino-PEG550 can be used in an embodiment of the present invention.

An embodiment of the present invention provides a poly (organophosphazene)-superparamagnetic nanoparticle complex including a biodegradable and thermosensitive phosphazene-based polymer and a superparamagnetic ferrite nanoparticle.

The biodegradable and thermosensitive phosphazene-based polymer showing a sol-to-gel behavior depending upon the temperature change can be represented by Chemical formula 1a, Chemical formula 1b and Chemical formula 1c:

[Chemical formula 1a]

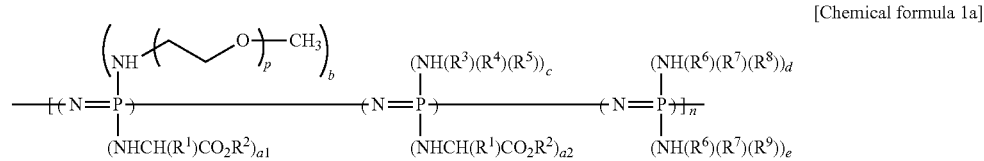

Wherein, p is a number of repeating unit of ethylene glycol ranging from 7 to 50, $NHCH(R^1)CO_2R^2$ is an ester of hydrophobic amino acid, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$, $NH(R^3)(R^4)(R^5)$ is an ester of amino acid, peptide or depsipeptide ester, and $R^3$ is CH(W), $R^4$ is selected from the group consisting of $CO_2$, $CONHCH(X)CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)$ $NH_2$, $CH_2C_3N_2H_3$, and $CH_2SH$, $NH(R^6)(R^7)(R^8)$ and $NH(R^6)(R^7)(R^9)$ are substitutents with a functional group, $R^6$ is CH(Y), $R^7$ is selected from the group consisting of CH, $C_2H_4$, $C_3H_6$, $C_4H_8$, $CH_2C_6H_4$, $CH_2CO_2$, O, CO, $CO_2$, S, N, CON, CONHCH(Z)O, CONH-CH(Z)S, CONHCH(Z)N, COCHNH(Z)CON, CONHCH(Z) CO, CONHCH(Z)$CO_2$, CONHCH(Z)CONHCH(M)O, CONHCH(Z)CONHCH(L)CONHCH(L)O, CONHCH(Z) CONHCH(M)S, CONHCH(Z)CONHCH(M)CONHCH(L) S, CONHCH(Z)CONHCH(M)N, CONHCH(Z)CONHCH (M)CONHCH(L)N, COCHNH(Z)CONHCH(M)CON, COCHNH(Z)CONHCH(M)CONHCH(L)CON, COCHNH (Z)CONHCH(M)CO, COCHNH(Z)CONHCH(M)CON-HCH(L)CO, COCHNH(Z)CONHCH(M)$CO_2$, and COCH-NH(Z)CONHCH(M)CONHCH(L)$CO_2$, $R^8$ is selected from the group consisting of OH, SH, H, $CH_3$, $C_2H_5$, $C_3H_7$, $C_4H_9$, $CH_2C_6H_5$, $CH_2CHCH_2$, and a protecting group listed in Table 1 to Table 5, where Y, Z, L, and M are independently is selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, NHCH(SH)$CO_2H$, $NH(CH_2)qSH$, $NH(CH_2CH_2NH)rH$, $[NHCH(C_4H_8NH_2)CO]rOH$, $[NHCH[(CH_2)_3C(=NH)(NH_2)]CO]_rOH$, folic acid, hyaluronic acid, polyhistidine, cyclodextrin, heparin, chitosan, and protamine, where q is a number of repeating unit of methylene ranging from 1 to 20, r is a number of repeating unit of ethyleneimine, lysine and arginine which ranges 1 to 18,000, $a_1$, $a_2$, b, c, d and e are the content of each substituent where each $a_1$, $a_2$, b, and d is 0.01 to 1.9, each c and e is 0 to 1.9, $a_1+a_2+b+c+d+e=2.0$, n is a polymerization degree of phosphazen polymer ranging from 5 to 100,000;

[Chemical formula 1b]

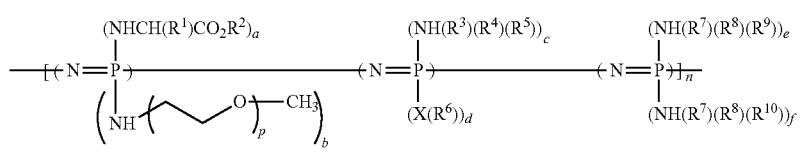

Wherein, p is a numerical value ranging from 7 to 50, in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$ and $CH_2CHCH_2$, in the formula $NH(R^3)(R^4)(R^5)$, $R^3$ is CH(W), $R^4$ is selected from the group consisting of $CO_2$, $CONHCH(X)CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_5NH_2$, $C_3H_6NHC(=NH)NH_2$, $CH_2C_3N_2H_3$ and $CH_2SH$, $XR^6$ is a thiol group or a vinyl group which is capable of cross-linking by UV-radiation, addition of cross-linking agent, addition of additive, addition of catalyst and/or mixing with other phosphazene-based polymer being capable of chemical cross-linking; or tyramine, tyrosine or phenyl derivatives being capable of cross-linking due to the addition of catalyst, wherein X is N or O, $R^6$ is a compounds including a thiol- or vinyl-group, compounds including a thiol- or vinyl-group protected with a protecting group, or tyramine, tyrosine or phenyl derivatives, and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, the protecting group of the thiol-group may be selected from an alkyl, benzyl (e.g., p-methoxybenzyl, o- or p-hydroxy or acetoxybenzyl, p-nitrobenzyl, 2,4,6-trimethylbenzyl, 2,4,6-trimethoxybenzyl, 4-pycoryl, 2-quinolinyl methyl, 2-pycoryl N-oxydo, 9-anthryl methyl, 9-fluorenyl methyl, xanthenyl, p-ferrocenyl methyl), diphenylmethyl, triphenylmethyl thioether (e.g., diphenylmethyl, bis(4-methoxyphenyl)methyl, 5-dibenzosurberyl, triphenylmethyl, diphenyl-4-pyridylmethyl, phenyl, 2,3-dinitrophenyl, t-butyl, 1-adamantyl), a substituted methyl derivative (e.g., methoxymethyl, isobutoxymethyl, benzyloxymethyl, 2-tetrahydropyranyl, benzylthiomethyl, phenylthiomethyl, thiazolidine, acetamidomethyl, trimethylacetamidomethyl, benzamidomethyl, allyloxycarbonylamidomethyl, phenylacetamidomethyl, phthalimidomethyl, acetyl, carboxyl, cyanomethyl), an ethyl derivative (e.g., 2-nitro-1-phenyl)ethyl, 2-(2,4-dinitrophenyl)ethyl, 2-(4'-pyridyl)ethyl, 2-cyanoethyl, 2-(trimethylsilyl)ethyl, 2,2-bis(carboethoxy)ethyl, (1-m-nitrophenyl-2-benzoyl)ethyl, 2-phenylsulfonylethyl, 1-(4-methylphenylsulfonyl)-2-methylprop-2-yl), thioester (e.g., acetyl, benzoyl, trifluoroacetyl, N-[[(p-biphenylyl)isopropoxy]carbonyl]-N-methyl-yaminothiobutyrate), thiocarbonate derivative 2,2,2-trichloroethoxycarbonyl, t-butoxycarbonyl, benzyloxycarbonyl, p-methoxybenzyloxycarbonyl), a thiocarbamate derivative (e.g., N-ethyl, N-methoxymethyl a miscellaneous derivative, an asymmetric disulfide (e.g., ethyl, t-butyl, a substituted S-phenyl disulfide), sulphenyl derivative (e.g., sulfonate, a sulphenyl thiocarbonate, a 3-nitro-2-pyridinesulphenyl sulfide, S-[tricarbonyl[1,2,3,4,5-η]-2,4-cyclohexadien-1-yl]-iron (1+), oxathiolone, and the protecting group of vinyl may be O-nitrophenyl selenoethyl, $NH(R^7)(R^8)(R^9)$ is a substitutent with a functional group, where $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z)CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$ and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, NHCH(SH)$CO_2H$, $NH(CH_2)_qSH$, $NH(CH_2CH_2NH)_qH$, $[NHCH(C_4H_5NH_2)CO]_qOH$, $[NHCH[(CH_2)_3C(=NH)(NH_2)]CO]_q$OH, folic acid, hyaluronic acid, polyhistidine, cyclodextrin, heparin, chitosan, protamine and a protecting group of general functional group, Where, Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4HNH_2$, $C_3H_6NHC(=NH)NH_2$, $CH_2C_3N_2H_3$ and $CH_2SH$, and q is a number of repeating unit ranging from 1 to 18,000, $NH(R^7)(R^8)(R^{10})$ is a thiol group, a vinyl group, tyramine, tyrosine or phenyl derivatives which is capable of cross-linking by UV-radiation, addition of cross-linking agent, addition of additive, addition of catalyst and/or mixing with other phosphazene-based polymer being capable of chemical cross-linking, $R^7$ and $R^8$ are the same substitutents as defined in the $NH(R^7)(R^8)(R^9)$, $R^{10}$ is a compound which is capable of cross-linking by UV-radiation, addition of cross-linking agent, addition of additive, addition of catalyst and/or mixing with other phosphazene-based polymer being capable of chemical cross-linking, is independently selected from the same groups of $R^6$, and $R^6$ and $R^{10}$ can be different from or the same, and specifically is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substituent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000;

ing of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, the protecting group of the thiol-group may be selected from an alkyl, benzyl (e.g., p-methoxybenzyl, o- or p-hydroxy or acetoxybenzyl, p-nitrobenzyl, 2,4,6-trimethylbenzyl, 2,4,6-trimethoxybenzyl, 4-pycoryl, 2-quinolinyl methyl, 2-pycoryl N-oxydo, 9-anthryl methyl, 9-fluorenyl methyl, xanthenyl, p-ferrocenyl methyl), diphenylmethyl, triphenylmethyl thioether (e.g., diphenylmethyl, bis(4-methoxyphe-

[Chemical formula 1c]

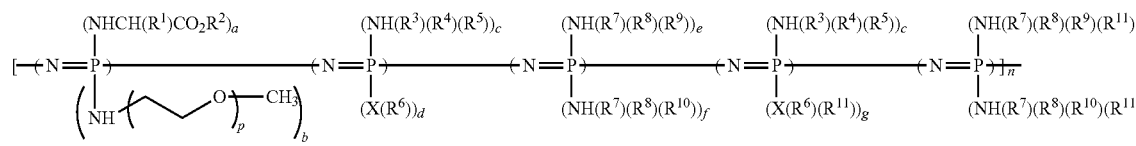

wherein p is a number of repeating unit of ethylene glycol ranging of 7 to 50, in group $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$, $NH(R^3)(R^4)(R^5)$ is an ester of amino acid, peptide or depsipeptide ester, and $R^3$ is CH(W), $R^4$ is selected from the group consisting of $CO_2$, $CONHCH(X)CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, in group $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $R^6$ is a thiol group or a vinyl group which is capable of cross-linking by UV-radiation, addition of cross-linking agent, addition of additive, addition of catalyst and/or mixing with other phosphazene-based polymer being capable of chemical cross-linking; or tyramine, tyrosine or phenyl derivatives being capable of cross-linking due to the addition of catalyst, wherein X is N or O, $R^6$ is a compounds including a thiol- or vinyl-group, compounds including a thiol- or vinyl-group protected with a protecting group, or tyramine, tyrosine or phenyl derivatives, and is selected from the group consistnyl)methyl, 5-dibenzosurberyl, triphenylmethyl, diphenyl-4-pyridylmethyl, phenyl, 2,3-dinitrophenyl, t-butyl, 1-adamantyl), a substituted methyl derivative (e.g., methoxymethyl, isobutoxymethyl, benzyloxymethyl, 2-tetrahydropyranyl, benzylthiomethyl, phenylthiomethyl, thiazolidine, acetamidomethyl, trimethylacetamidomethyl, benzamidomethyl, allyloxycarbonylamidomethyl, phenylacetamidomethyl, phthalimidomethyl, acetyl, carboxyl, cyanomethyl), an ethyl derivative (e.g., 2-nitro-1-phenyl)ethyl, 2-(2,4-dinitrophenyl)ethyl, 2-(4'-pyridyl)ethyl, 2-cyanoethyl, 2-(trimethylsilyl)ethyl, 2,2-bis(carboethoxy)ethyl, (1-m-nitrophenyl-2-benzoyl)ethyl, 2-phenylsulfonylethyl, 1-(4-methylphenylsulfonyl)-2-methylprop-2-yl), thioester (e.g., acetyl, benzoyl, trifluoroacetyl, N-[[(p-biphenylyl)isopropoxy]carbonyl]-N-methyl-yaminothiobutyrate), thiocarbonate derivative 2,2,2-trichloroethoxycarbonyl, t-butoxycarbonyl, benzyloxycarbonyl, p-methoxybenzyloxycarbonyl), a thiocarbamate derivative (e.g., N-ethyl, N-methoxymethyl a miscellaneous derivative, an asymmetric disulfide (e.g., ethyl, t-butyl, a substituted S-phenyl disulfide), sulphenyl derivative (e.g., sulfonate, a sulphenyl thiocarbonate, a 3-nitro-2-pyridinesulphenyl sulfide, S-[tricarbonyl[1,2,3,4,5-η]-2,4-cyclohexadien-1-yl]-iron (1+), oxathiolone, and the protecting group of vinyl may be O-nitrophenyl selenoethyl, $NH(R^7)(R^8)(R^9)$ is a substituent including a functional group, where, $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z)CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)_8CO]_q$,

[OCOC$_6$H$_5$O(CH$_2$)$_3$OC$_6$H$_5$CO]$_q$, and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine, and a general protecting group of a functional group, where Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$HNH$_2$, C$_3$H$_6$NHC(=NH)NH$_2$, CH$_2$C$_3$N$_2$H$_3$, and CH$_2$SH, and q represents a number of a repeating unit and ranges from 1 to 18,000, NH(R$^7$)(R$^8$)(R$^{10}$) is a thiol group, a vinyl group, tyramine, tyrosine or phenyl derivatives which is capable of cross-linking by UV-radiation, addition of cross-linking agent, addition of additive, addition of catalyst and/or mixing with other phosphazene-based polymer being capable of chemical cross-linking, R$^7$ and R$^8$ are the same substitutents as defined in the NH(R$^7$)(R$^8$)(R$^9$), and R$^{10}$ is a compound being capable of cross-linking by UV-radiation, addition of cross-linking agent, addition of additive, addition of catalyst and/or mixing with other phosphazene-based polymer which is capable of chemical cross-linking, is independently selected from the same groups of R$^6$, and R$^6$ and R$^{10}$ can be different from or the same, X(R$^6$)(R$^{11}$) is a substituent bound with physiologically-active material such as drug, X and R$^6$ are the same as define above for X(R$^6$), R$^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, R$^7$, R$^8$, R$^9$, and R$^{11}$ are substituents bound with physiologically-active material such as drug and are the same as defined above, R$^7$, R$^8$, R$^{10}$, and R$^{11}$ are substituents bound with physiologically-active material such as drug and are the same as defined above, a, b, c, d, e, f, g, h and i are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

In the definitions of R$^6$ and R$^{10}$ of Chemical formulae 1b and 1c, the acrylate-based compound is an acrylate; an acrylate including a C1 to C30 substituted or unsubstituted linear or branched alkyl substituted with at least one selected from the group consisting of a halogen, a C1 to C12 alkoxy, an acryloyloxy, and an amino acid (for examples, ethyl acrylate, ethoxyethyl acrylate, diethoxyethyl acrylate, butyl acrylate, propyl acrylate, hexyl acrylate, 3-chloro-2-propyl acrylate, 3-(acryloyloxy)-2-propyl acrylate, glycine ethyl acrylate, and etc.); an acrylate including an amino acid group (for example, glycidyl acrylate, and etc.); ethylene glycol acrylate; or a polyethyleneglycol acrylate including polyethyleneglycol of a molecular weight of 200 to 2,500, the metacrylate-based compound is metacrylate; metacrylate including a C1 to C30 substituted or unsubstituted linear or branched alkyl substituted with at least one selected from the group consisting of a halogen, a C1 to C12 alkoxy, an acryloyloxy, and an amino acid (for examples, ethyl metacrylate, ethoxyethyl metacrylate, diethoxyethyl metacrylate, butyl metacrylate, propyl metacrylate, hexyl metacrylate, 3-chloro-2-propyl metacrylate, 3-(acryloyloxy)-2-propyl metacrylate, glycine ethyl metacrylate, and etc.); metacrylate including an amino acid group (for example, glycidyl metacrylate, and etc.); or polyethyleneglycol metacrylate including polyethyleneglycol of a molecular weight of 200 to 2,500, the acrylamide-based compound is acryl amide; acryl amide including a C1 to C30 substituted or unsubstituted linear or branched alkyl substituted with at least one selected from the group consisting of a halogen, a C1 to C12 alkoxy, acryloyloxy, and an amino acid (for examples, ethyl acrylamide, ethoxyethyl acrylamide, diethoxyethyl acrylamide, butyl acrylamide, propyl acrylamide, hexyl acrylamide, 3-chloro-2-propyl acrylamide, 3-(acryloyloxy)-2-propyl acrylamide, glycine ethyl acrylamide, and etc.); acryl amide including an amino acid group (for example, glycidyl acrylamide); ethyleneglycol acrylamide; or polyethyleneglycol amide including polyethyleneglycol of a molecular weight of 200 to 2,500, the vinyl sulfone-based compound is vinyl sulfone, vinyl sulfone-ethyleneglycol, vinyl sulfone-polyethyleneglycol including polyethyleneglycol of a molecular weight of 200 to 2,500, vinyl sulfone-alkylate including a C1 to C30 alkyl, vinyl sulfone-amino acid (for example, vinyl sulfone-cystein), or vinyl sulfone-peptide, the thiol-based compound is thiol-polyethylene glycol including polyethylene glycol of a molecular weight of 200 to 2,500, or thiol-alkylate including a C1 to C30 alkyl, the cysteine-based compound is cysteine, N-acetyl-cysteine, or N-acetyl-cysteine alkyl ester including a C1 to C30 alkyl (for examples, N-acetyl-cystein methyl ester or N-acetyl-cystein ethyl ester), the cisteamine-based compound is cisteamine, or N-acetyl-cisteamine, the mercaptic acid-based compound is 2-mercapto succinic acid, the allyl pyrimidine-based compound is 1-allyl-2-aminopyridinium, or 1-allyl-6-amino-3-ethyl-5-nitrosouracil, the tyramine-based compound is tyramine, or 3-methoxytyramine, the tyrosine-based compound is tyrosine, or tyrosine methylester, or tyrosine ethylester, and the phenol-based compound is selected from the group consisting of 2-amino-4-phenylphenol, 2-amino-4-teriaryamylphenol, 2-amino-4-tert-butylphenol phenol, 8-amino-2-naphthol, 5-amino-1-naphthol, 4-amino-1-naphthol, 3-amino-2-naphthol, 1-amino-2-naphthol, 4-amino 2,5 dimethylphenol, 5-amino-2-methoxyphenol, 5-amino-2-methylphenol, 4-amino-3-methylphenol, 4-amino-2-methylphenol, 2-amino-5-methylphenol, 2-amino-4-methylphenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitrophenol, 2-amino-5-nitrophenol, 2-amino-4-nitrophenol, 2-amino-4 fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6nitrophenol, and 4-amino-2,6-dibromophenol.

More specifically, $R^9$ is folic acid, hyaluronic acid, cyclodextrin, imidazole-based compounds (Dacarbazine, 1-(3-Aminopropyl)imidazole, Methylhistamine dihydrochloride, 4-(1H-Imidazol-1-yl)aniline, Histamine, Imiquimod, Biotin ethylenediamine, 2-(2-Methylimidazolyl)ethylamine dihydrochloride, 5-Amino-4-imidazolecarboxamide hydrochloride, 5-Aminoimidazole-4-carboxamide, 4-Imidazoleacrylic acid, 4-Imidazolecarboxylic acid, 22-Iminobiotin, L-(+)-Ergothioneine, 4,5-Imidazoledicarboxylic acid, 1-(2-Hydroxyethyl)imidazole, 4(5)-(Hydroxymethyl)imidazole, 4-Imidazolemethanol hydrochloride, Etanidazole, 4-(Imidazol-1-yl) phenol, 2-Hydroxymethyl-1-methyl-5-nitro-1H-imidazole (HMMNI), 2-Mercaptoimidazole, 1-(4-Hydroxybenzyl)imidazole-2-thiol, Thiabendazole, 1,1'-Thiocarbonyldiimidazole, 2-Mercapto-1-methylimidazole, 2-Mercaptoimidazole, Methimazole, 1-(2,3,5,6-Tetrafluorophenyl)imidazole, 1-(Heptafluorobutyryl)imidazole, 1-(Pentafluoropropionyl) imidazole, 1-(Trifluoroacetyl)imidazole, 11-(Trifluoromethanesulfonyl)imidazole, 1-[2-(Trifluoromethyl)phenyl]imidazole, 22-Bromo-1H-imidazole, 2-Butyl-4-chloro-5-(hydroxymethyl)imidazole, 2-Butyl-5-chloro-1H-imidazole-4-carboxaldehyde, 2-Chloro-1H-imidazole, 4-(4-Bromophenyl)-1H-imidazole, 4-(4-Chlorophenyl)-1H-imidazole, 4-(4-Fluorophenyl)-1H-imidazole, 5-Bromo-1-methyl-1H-imidazole, 6-Bromo-1H-benzimidazole, Cyazofamid, Imazalil, Ketoconazole, Fenobam, Imazalil sulfate, Losartan Potassium, Neurodazine, Nutlin-3, SB 220025 trihydrochloride, SB 202190 (4-(4-Fluorophenyl)-2-(4-hydroxyphenyl)-5-(4-pyridyl)-1H-imidazole), PD 169316 (4-(4-Fluorophenyl)-2-(4-nitrophenyl)-5-(4-pyridyl)-1H-imidazole), SB 239063 (trans-1-(4-Hydroxycyclohexyl)-4-(4-fluorophenyl)-5-(2-methoxypyridimidin-4-yl)imidazole), Tioconazole, Triflumizole, 2,4,5-Tribromoimidazole, 5-Chloro-1-methyl-4-nitroimidazole, 2-Ethyl-4-methyl-1H-imidazole-1-propanenitrile, 4,5-Dicyanoimidazole, 5-Ethynyl-1-methyl-1H-imidazole and etc.), histidine, lysine, arginine, cystein, thiolalkylamine (for example, C1-C50 alkyl), spermine, spermidine, polyethyleneimine having various molecular weight, polyhistidine, polylysine, polyarginine, protamine, heparine, chitosan and the protamine and other compounds do not limited by their molecular weight, prepareably has a weight-average molecular weight of 50 to 100,000 but do not limited thereto.

In Chemical formula 1c, $R^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group.

the protein, polypeptide, peptide, fusion protein and antibody are selected from the group consisting of erythropoietin (EPO), Interferon-alpha, Interferon-beta, Interferon-gamma, growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, Insulin, albumin, Botulinum toxin, oxytocin, vasopressin, fibroblast growth factor (FGF), epidermal growth factor (EGF), platelet-derived growth factor (PDGF), keratinocyte growth factor, insulin-like growth factor (IGF), vascular endothelial growth factor (VEGF), transforming growth factor-beta, (TGF-β), nerve growth factor, brain-derived neurotrophic factor (BDNF), neurotrophin-3 (NT-3), neurotrophin-4/5, prolactin, luliberin, LHRH agonists, LHRH antagonists, glucagon, Interleukin-2 (IL-2), Interleukin-11 (IL-11), gastrin, tetragastrin, pentagastrin, urogastrone, secretin, enkephalins, endorphins, angiotensins, tumor necrosis factor (TNF), tumor necrosis factor related apoptosis inducing ligand (TRAIL), heparinase, bone morphogenic proteins (BMPs), human atrial natriuretic peptide (hANP), glucagon-like peptide (GLPep), Exnatide, Calcitonin (human or salmon), Teriparatide, Coagulation factors, hirudin, Anakinra, renin, bradykinin, bacitracins, polymyxins, colistins, tyrocidine, gramicidins, cyclosporins, neurotensin, tachykinin, neuropeptide Y(NPY), peptide YY (PYY), vasoactive intestinal polypeptide (VIP), pituitray adenylate cyclase-activating polypeptide (PACAP) and synthetic analogues thereof, RGD, Collagen, Fibronectin, Laminin, Vitronectin, Proteoglycan, monoclonal antibody, fusion protein, beta-glucocerebrosidase, Lactase, Alglucosidase-α, alpha-galactosidase A, Lipase, Amylase, Protease, Hyaluronidase, L-asparaginase, and cytokines, the hormone is selected from the group consisting of growth hormone (somatotropin), luteinizing hormone releasing hormone (LHRH), somatostatin, thyrotropin releasing hormone (TRH), adrenocorticotropic hormone), Follicle-stimulating hormone (FSH), Human Chorionic Gonadotropin (HCG), Lutropin-α, testosterone, estradiol, progesterone, prostaglandins, and their synthetic analogues, modified material and material having the same efficacy, the vaccine is selected from the group consisting of hepatitis vaccine, HPV vaccine, and lyme disease vaccine, the gene is selected from the group consisting of small interfernce RNA (siRNA), small hairpin RNA (shRNA), micro RNA (miRNA), aptamer, plasmid DNA and antisense oligodeoxynucleotide (AS-ODN), the anti-cancer drug is selected from the group consisting of paclitaxel, doxorubicin, 5-fluorouracil, cisplatin, carboplatin, oxaliplatin, tegafur, irinotecan, docetaxel, cyclophosphamide, gemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassuim, medroxypogexterone acetate, epirubicin, letrozole, pirarubicin, topotecan, altretamine, toremifene citrate, BCNU, taxotere, actinomycin D, Anasterozole, Belotecan, Imatinib, Floxuridine, Gemcitabine, Hydroxyurea, Zoledronate, Vincristine, Flutamide, Valrubicin, Streptozocin, Silibinin, polyethyleneglycol conjugated anti-cancer drug, and their synthetic analogue, modified material and material having the same efficacy, the angiogenesis inhibitor is selected from the group consisting of BMS-275291 (Bristol-Myers Squibb, New York), Clodronate, 6-deoxy-6-demethyl-4-dedimethylaminotetracycline (COL-3), Doxycycline, Marimastat, 2-methoxyestradiol, Squalamine, SU5164, Thalidomide, TNP-470, Combretastatin A4, Soy isoflavone, Enzastaurin, CC 5013 (Revimid; Celgene Corp, Warren, N.J.), Celecoxib, ZD 6474 (inhibitor of vascular endotherial growth factor receptor tyrosine kinase, Halofuginone hydrobromide, Interferon-alpha, Bevacizumab, AE-941 (Neovastat), Interleukin-12, vascular endothelial growth factor trap (VEFG-trap), Cetuximab, Rebimastat, matrix metalloprotease (MMP) inhibitor, Protein kinase C beta inhibitor, Endinhibit, vatalanib (PTK787/ ZK 222584), sunitinib malate (SU11248), cilenqitide (EMD-121974), humanized monoclonal antibody MEDI-522, EOS-200-4, integrin-alpha-5-beta-1 antagonist (ATN-161), and their synthetic analogue, modified material and material having the same efficacy.

The protecting group used for general functional group in Chemical formula 1a to Chemical formula 1c may be generally known protecting groups, and the examples are illustrated in Table 1 to Table 5.

TABLE 1

| Functional group | Protecting group (R' = R⁸) |
|---|---|
| Carboxyl group (RCOOR') | Fluorenylmethyl ester, Methoxymethyl ester ($CH_2OCH_3$), Methylthiomethyl ester ($CH_2SCH_3$), Tetrahydrofuranyl ester, Methoxyethoxymethyl ester ($CH_2OCH_2CH_2OCH_3$), 2-(trimethylsilyl)ethoxymethyl ester ($CH_2OCH_2CH_2Si(CH_3)_3$), Benzyloxymethyl ester ($CH_2OCH_2C_6H_5$), Pivaloyloxymethyl ester ($CH_2O_2CC(CH_3)_3$), Phenylacetoxymethyl ester ($CH_2O_2CCH_2Ph$), Triisopropylsilylmethyl ester ($CH_2Si$-i-$Pr_3$), Cyanomethyl ester ($CH_2CN$), Acetol ester ($CH_2COCH_3$), Phenacyl ester ($CH_2COC_6H_5$), p-Bromophenacyl ester ($CH_2COC_6H_4$-p-Br), α-Methylphenacyl ester ($CH(CH_3)COC_6H_5$), p-Methoxyphenacyl ester ($CH_2COC_6H_4$-p-$OCH_3$), Desyl ester, Carboxamidomethyl ester ($CH_2CONH_2$), p-Azobenzenecarboxamidomethyl ester ($CH_2(O)CNHC_6H_4N=NC_6H_5$), N-Phthalimidomethyl ester, 2,2,2-Trichloroethyl ester ($CH_2CCl_3$), 2-Haloethyl ester ($CH_2CH_2X$, X = I, Br, Cl), ω-Chloroalkyl ester (($CH_2$)$_n$Cl, n = 4, 5), 2-(trimethylsilyl)ethyl ester ($CH_2CH_2Si(CH_3)_3$), 2-Methylthioethyl ester ($CH_2CH_2SCH_3$), 1,3-Dithianyl-2-methyl ester, 2-(p-Nitrophenylsulfenyl)ethyl ester ($CH_2CH_2SC_6H_4$-p-$NO_2$), 2-(p-Toluenesulfonyl)ethyl ester ($CH_2CH_2SO_2C_6H_4$-p-$CH_3$), 2-(2'-Pyridyl)ethyl ester ($CH_2CH_2$-2-$C_5H_4N$), 2-(p-Methoxyphenyl)ethyl ester ($CH_2CH_2C_6H_4$-p-$CH_3$), 2-(diphenylphosphino)ethyl ester ($CH_2CH_2P(C_6H_5)_2$), 1-Methyl-1-phenylethyl ester ($C(CH_3)_2C_6H_5$), 2-(4-Acetyl-2-nitrophenyl)ethyl ester, 2-Cyanoethyl ester ($CH_2CH_2CHN$), t-Butyl ester ($C(CH_3)_3$), 3-Methyl-3-pentyl ester ($CCH_3(C_2H_4)_2$), Dicyclopropylmethyl ester, 2,4-Dimethyl-3-pentyl ester ($CH(i-Pr)_2$), Cyclopentyl ester (c-$C_5H_9$), Cyclohexyl ester (c-$C_6H_{11}$), Allyl ($CH_2CH=CH_2$), Methallyl ester ($CH_2(CH_3)C=CH_2$), 2-Methylbut-3-en-2-yl ester ($C(CH_3)_2CH=CH_2$), 3-Methylbut-2-enyl ester ($CH_2CH=C(CH_3)_2$), 3-Buten-1-yl ester ($CH_2CH_2CH=CH_2$), 4-(Trimethylsilyl)-2-buten-1-yl ester ($CH_2CH=CHCH_2Si(CH_3)_3$), Cinnamyl ester ($CH_2CH=CHC_6H_5$), α-Methylcinnamyl ester ($CH(CH_3)CH=CHC_6H_5$), Prop-2-ynyl ester ($CH_2C\equiv CH$), Phenyl ester ($C_6H_5$), 2,6-Dimethylphenyl ester, 2,6-Diisopropylphenyl ester, 2,6-Di-t-butyl-4-methylphenyl ester, 2,6-Di-t-Butyl-4-methoxyphenyl ester, p-(Methylthio)phenyl ester ($C_6H_4$-p-$SCH_3$), Pentafluorophenyl ester ($C_6F_5$), Benzyl ester ($CH_2C_6H_5$), Triphenylmethyl ester ($C(C_6H_5)_3$), Diphenylmethyl ester ($CH(C_6H_5)_2$) Bis(o-nitrophenyl)methyl ester ($CH(C_6H_4$-o-$NO_2)_2$), 9-Anthrylmethyl ester ($CH_2$-9-Anthryl), 2-(9,10-Dioxo)anthrylmethyl ester, 5-dibenzosuberyl ester, 1-Pyrenylmethyl ester, 2-(trifluoroaceticmthyl)-6-chromonylmethyl ester, 2,4,6-Trimethylbenzyl ester ($CH_2C_6H_2$-2,4,6-($CH_3$)$_3$), p-Bromobenzyl ester ($CH_2C_6H_4$-p-Br), o-Nitrobenzyl ester ($CH_2C_6H_4$-o-$NO_2$), p-Nitrobenzyl ester ($CH_2C_6H_4$-p-$NO_2$), p-Methoxybenzyl ester ($CH_2C_6H_4$-p-$OCH_3$), 2,6-Dimethoxybenzyl ester ($CH_2C_6H_3$-2,6-($OCH_3$)$_2$), 4-(Methylsulfinyl)benzyl ester ($CH_2C_6H_4(O)S$-4-$CH_3$), 4-Sulfobenzyl ester ($CH_2C_6H_4SO_3^-Na^+$), 4-Azidomethoxybenzyl ester ($CH_2C_6H_4OCH_2N_3$), 4-{N-[1-(4,4-Dimethyl-2,6-dioxocyclohexylidene)-3-methlbutyl]amino}benzyl ester, Piperonyl ester, 4-Picolyl ester ($CH_2$-4-pyridyl), p-P-Benzayl ester ($CH_2C_6H_4$-p-P), Trimethylsilyl ester ($Si(CH_3)_3$), Triethylsilyl ester ($Si(C_2H_5)_3$), t-Butyldimethylsilyl ester ($Si(CH_3)_2C(CH_3)$), i-Propyldimethylsilyl ester ($Si(CH_3)_2CH(CH_3)_2$), Phenyldimethylsilyl ester ($Si(CH3)_2C_6H_5$), Di-t-butylmethylsilyl ester ($SiCH_3(t-Bu)_2$), Triisopropylsilyl ester |
| Thiol group (RSR') | S-Alkyl thioether ($C_nH_{2n+1}$), S-Benzyl thioether ($CH_2Ph$), S-p-Methoxybenzyl thioether ($CH_2C6H4$-p-$OCH_3$), S-o- or p-Hydroxy-or-Acetoxybenzyl thioether ($CH_2C6H4$-o-(or p-)-OR', R' = H or Ac), S-p-Nitrobenzyl thioether ($CH_2C_6H_4$-p-$NO_2$), S-2,4,6-Trimethylbenzyl thioether ($CH_2C_6H_2$-2,4,6-$Me_3$), S-2,4,6-Trimethoxybenzyl thioether ($CH_2C_6H_2$-2,4,6-($OMe$)$_3$), S-4-Picolyl thioether ($CH_2$-4-pyridyl), S-2-Quinolinylmethyl thioether, S-2-Picolyl N-Oxide thioether ($CH_2$-2-pyridyl N-Oxide), S-9-Anthrylmethyl thioether ($CH_2$-9-anthtyl), S-9-Fluorenylmethyl thioether, S-Xanthenyl thioether, S-Ferrocenylmethyl thioether, S-Diphenylmethyl thioether ($CH(C_6H_5)_2$), S-Bis(4-methoxyphenyl)methyl thioether ($CH(C_6H_4$-4-$OCH_3)_2$), S-Bis(4-methoxyphenyl)phenylmethyl thioether, S-5-Dibenzosuberyl thioether, S-Triphenylmethyl thioether ($C(C_6H_5)_3$), S-Diphenyl-4-pyridylmethyl thioether ($C(C_6H_5)_2$-4-pyridyl), S-Phenyl thioether ($C_6H_5$), S-2,4-Dinitrophenyl thioether ($C_6H_3$-2,4-($NO_2)_2$), S-t-Butyl thioether ($C(CH_3)_3$), S-1-Adamantyl thioether, S-Methoxymethyl monothioacetal ($CH_2OCH_3$), S-Isobutoxymethyl monothioacetal ($CH_2OCH_2CH(CH_3)_2$), S-Benzyloxymethyl monothioacetal ($CH_2OBn$), S-2-Tetrahydropyranyl monothioacetal, S-Benzylthiomethyl dithioacetal ($CH_2SCH_2C_6H_5$), S-Phenylthiomethyl dithioacetal ($CH_2SC_6H_5$), S-Acetamidomethyl thioacetal ($CH_2NHCOCH_3$), S-Trimethylacetamidomethyl thioacetal ($CH_2NHCOC(CH_3)_3$), S-Benzamidomethyl (thioacetal$CH_2NHCOC_6H_5$), S-Allyloxycarbonylaminomethyl thioacetal ($CH_2NH(O)COCH_2CH=CH_2$), S-Phenylacetamidomethyl thioacetal ($CH_2NH(O)CCH_2C_6H_5$), S-Phthalimidomethyl thioacetal, S-Acetyl, S-Carboxy, and S-Cyanomethyl thioether ($CH_2X$, X = —$COCH_3$, —$CO_2H$, —CN), S-(2-Nitro-1-phenyl)ethyl thioether ($CH(C_6H_5)CH_2NO_2$), S-2-(2,4-Dinitrophenyl)ethyl thioether, S-2-(4'-Pyridyl)ethyl thioether ($CH_2CH_2NC_4H_4$), S-2-Cyanoethyl thioether ($CH_2CH_2CN$), S-2-(Trimethylsilyl)ethyl thioether ($CH_2CH_2TMS$), S-2,2-Bis(carboethoxy)ethyl thioether ($CH_2CH(COOC_2H_5)_2$), S-(1-m-Nitrophenyl-2-benzoyl)ethyl thioether ($CH(C_6H_4$-m-$NO_2)CH_2COC_6H_5$), S-2-phenylsulfonylethyl thioether ($CH_2CH_2SO_2Ph$), S-1-(4-Methylphenylsulfonyl)-2-methylprop-2-yl thioether ($C(CH_3)_2CH_2SO_2C_6H_4$-4-$CH_3$), Triisopropylsilyl thioether, S-Acetyl derivatives ($COCH_3$), S-Benzoyl derivatives ($COC_6H_5$), S-Trifluoroaceticacetyl derivatives ($COCF_3$), S-2,2,2-Trichloroethoxycarbonyl derivatives ($COOCH_2CCl_3$), S-t-Butoxycarbonyl derivatives ($COOC(CH_3)_3$), S-Benzyloxycarbonyl derivatives ($COOCH_2C_6H_5$), S-p-Methoxybenzyloxycarbonyl derivatives ($COOCH_2C_6H_4$-p-$OCH_3$), S—(N-Ethylcarbamate)($CONHC_2H_5$), S—(N-Methoxymethylcarbamate) ($CONHCH_2OCH_3$), S-Ethyl disulfide ($SC_2H_5$), S-t-Butyl disulfide ($SC(CH_3)_3$) |
| Hydroxy group (ROR') | Methyl ether ($CH_3$), Methoxymethyl ether ($CH_2OCH_3$), Methylthiomethyl ether ($CH_2SCH_3$), (Phenyldimethylsilyl)methoxymethyl ether ($CH_2OCH_2Si(CH_3)_2C_6H_5$), Benzyloxymethyl ether ($CH_2OCH_2Ph$), p-Methoxybenzyloxymethyl ether ($CH_2OCH_2C_6H_4O$-p-Me), p-Nitrobenzyloxymethyl ether ($CH_2OCH_2C_6H_4$-4-$NO_2$), o-Nitrobenzyloxymethyl ether ($CH_2OCH_2C_6H_4$-2-$NO_2$), (4-Methoxyphenoxy)methyl ether ($CH_2OC_6H_4$-4-$OCH_3$), Guaiacolmethyl ether ($CH_2OC_6H_4$-2-OMe), t-Butoxymethyl ether ($CH_2O$-t-Bu), 4-Pentenyloxymethyl ether ($CH_2OCH_2CH_2CH_2CH=CH_2$), Siloxymethyl ether ($CH_2OSiR'R''$, R' = t-Bu, R'' = Me; R' = Thexyl, R'' = Me; R' = t-Bu, R'' = Ph), 2-Methoxyethoxymethyl ether ($CH_2OCH_2CH_2OCH_3$), 2,2,2-Trichloroethoxymethyl ether ($CH_2OCH_2CCl_3$), Bis(2-chloroethoxy)methyl ether ($CH(OCH_2CH_2Cl)_2$), 2-(Trimethylsilyl)ethoxymethyl ether ($CH_2OCH_2CH_2SiMe_3$), Methoxymethyl ether, Tetrahydropyranyl ether, 3-Bromotetrahydropyranyl ether, Tetrahydrothiopyranyl ether, 1-Methoxycyclohexyl ether, 4-Methoxytetrahydropyranyl ether, 4-Methoxytetrahydrothiopyranyl ether, 1-[(2-Chloro-4-methyl)phenyl]-4-methoxypiperidin-4-yl ether, 1-(2-Fluorophenyl)-4-methoxypiperidin-4-yl ether, 1,4-Dioxan-2-yl ether, Tetrahydrofuranyl ether, |

TABLE 1-continued

| Functional group | Protecting group (R' = R$^8$) |
|---|---|
| | Tetrahydrothiofuranyl ether, 2,3,3a,4,5,6,7,7a-octahydro-7,8,8-trimethyl-4,7-methanobenzofuran-2-yl ether, 1-Ethoxyethyl ether (CH(OC$_2$H$_5$)CH$_3$), 1-(2-Chloroethoxy)ethyl ether (CH(CH$_3$)OCH$_2$CH$_2$Cl), 1-[2-(Trimethylsilyl)ethoxy]ethyl ether, 1-Methyl-1-methoxyethyl ether (C(OCH$_3$)(CH$_3$)$_2$), 1-Methyl-1-benzyloxyethyl ether (C(OBn)(CH$_3$)$_2$), 1-Methyl-1-benzyloxy-2-fluoroethyl ether (C(OBn)(CH$_2$F)(CH$_3$), 1-Methyl-1-phenoxyethyl ether (C(OPh)(CH$_3$)$_2$), 2,2,2-trichloroethyl ether (CH$_2$CCl$_3$), 1,1-Dianisyl-2,2,2-trichloroethyl ether, 1,1,1,3,3,3-Hexafluoro-2-phenylisopropyl ether (C(CHF$_3$)$_2$Ph), 2-Trimethylsilylethyl ether (CH$_2$SiMe$_3$), 2-(Benzylthio)ethyl ether (CH$_2$CH$_2$SBn), 2-(Phenylselenyl)ethyl ether (CH$_2$CH$_2$SePh), t-Butyl ether, Allyl ether (CH$_2$CH=CH$_2$), Propargyl ether (CH$_2$C≡CH), p-Methoxyphenyl ether (C$_6$H$_4$O-p-Me), p-Nitrophenyl ether (C$_6$H$_4$-p-NO$_2$), 2,4-Dinitrophenyl ether (C$_6$H$_3$-2,4-(NO$_2$)$_2$), 2,3,5,6-Tetrafluoro-4-(trifluoroaceticmethyl)phenyl ether (C$_6$F$_4$CF$_3$), Benzyl ether (CH$_2$Ph), p-Methoxybenzyl ether (CH$_2$C$_6$H$_4$-p-OMe), 3,4-Dimethoxybenzyl ether (CH$_2$C$_6$H$_3$-3,4-(OMe)$_2$), o-Nitrobenzyl ether (CH$_2$C$_6$H$_4$-o-NO$_2$), p-Nitrobenzyl ether (CH$_2$C$_6$H$_4$-p-NO$_2$), p-Halobenzyl ether (CH$_2$C$_6$H$_4$-p-X, X = Br, Cl), 2,6-Dichlorobenzyl ether (CH$_2$C$_6$H$_3$-2,6-Cl$_2$), p-Cyanobenzyl ether (CH$_2$C$_6$H$_4$-p-CN), p-Phenylbenzyl ether (CH$_2$C$_6$H$_4$-p-C$_6$H$_5$), 2,6-Difluorobenzyl ether (CH$_2$C$_6$H$_3$F$_2$), p-Acylaminobenzyl ether (CH$_2$C$_6$H$_4$-p-NHCOR'), p-Azidobenzyl ether (CH$_2$C$_6$H$_4$-4-N$_3$),4-Azido-3-chlorobenxyl ether (CH$_2$C$_6$H$_3$-3-Cl-4-N$_3$), 2-Trifluoroaceticmethylbenzyl ether (CH$_2$C$_6$H$_4$-2-CF$_3$), p-(Methylsulfinyl)benzyl ether (CH$_2$C$_6$H$_4$-p-(MeS(O)), 2- and 4-Picolyl ether(CH$_2$C$_5$H$_4$N), 3-Methyl-2-picolyl N-Oxido ether, 2-Quinolinylmethyl ether, 1-Pyrenylmethyl ether, Diphenylmethyl ether (CHPh$_2$), p,p'-Dinitrobenzhydryl ether (CH(C$_6$H$_4$-p-NO$_2$)$_2$), 5-Dibenzosuberyl ether, Triphenylmethyl ether, p-Methoxyphenyldiphenylmethyl ether (C(Ph)$_2$C$_6$H$_4$-p-OMe), Di(p-methoxyphenyl)phenylmethyl ether (CPh(p-MeOC$_6$H$_4$)$_2$), Tri(p-methoxyphenyl)methyl ether (C(p-MeOC$_6$H$_4$)$_3$), 4-(4'-Bromophenacyloxy)phenyldiphenylmethyl ether (C(Ph)$_2$C$_6$H$_4$-p-(OCH$_2$(O)CC$_6$H$_4$-p-Br), 4,4',4''-Tris(4,5-dichlorophthalimidophenyl)methyl ether, 4,4',4''-Tris(levulinoyloxyphenyl)methyl) ether, 4,4'4''-Tris(benzoyloxyphenyl)methyl) ether, 4,4'-Dimethoxy-3''-[N-(imidazolylmethyl)]trityl ether, 4,4'-Dimethoxy,3''-[N-(imidazolylethyl)carbamoyl)trityl ether, 1,1-Bis(4-methoxyphenyl)-1-pytenylmethyl ether, 4-(17-tetrabenzo[a,c,g,i]fluorenylmethyl)-4',4''-dimethoxytrityl ether, 9-Anthryl ether, 9-(9-Phenyl)xanthenyl ether, Tritylone ether, 1,3-Benzodithiolan-2-yl ether, Benzisothiazolyl-S,S-dioxido ether, Trimethylsilyl (e.g., Si(CH$_3$)$_3$) ether, Triethylsilyl (SiEt$_3$) ether, Triisopropylsilyl (Si(i-Pr)$_3$) ether, Dimethylisopropylsilyl (SiMe$_2$-i-Pr) ether, Diethylisopropylsilyl (SiEt$_2$-i-Pr) ether, Dimethylthesilyl ether ((CH$_3$)$_2$Si(CH$_3$)$_2$CCH(CH$_3$)$_2$), t-Butyldimethylsilyl ether (SiMe$_2$-t-Bu),t-Butyldiphenylsilyl ether (SiPh$_2$-t-Bu), Tribenxylsily ether (Si(CH$_2$C$_6$H$_5$)$_3$), Tri-p-xylylsilyl ether (Si(CH$_2$C$_6$H$_4$-p-CH$_3$)$_3$), Triphenylsilyl ether (SiPh$_3$), Diphenylmethylsily ether (SiMePh$_2$), Di-t-butylmethylsilyl ether (SiMe(t-Bu)$_2$),Tris(trimethylsilyl)silyl ether ([Si[Si(CH$_3$)$_3$]$_3$), (2-Hydroxystyryl)dimethylsilyl ether, (2-Hydroxystyryl)diisopropylsilyl ether, t-Butylmethoxyphenylsilyl ether (SiPh(OCH$_3$)-t-Bu), t-Butoxydiphenylsilyl ether (Si(t-OBu)Ph$_2$), Formate ester (CHO), Benzoylformate ester (COCOPh), Acetate ester (COCH$_3$), Chloroacetate ester (COCH$_2$Cl), Dichloroacetate ester (COCHCl$_2$), Trichloroacetate ester (COCCl$_3$), Trifluoroaceticacetate ester (COCF$_3$), Methoxyacetate ester (COCH$_2$OMe), Triphenylmethoxyacetate ester (COCH$_2$OCPh$_3$), Phenoxyaetate ester (COCH$_2$OPh), p-chlorophenoxyacetate ester (COCH$_2$OC$_6$H$_4$-p-Cl), phenylacetate ester (COCH$_2$Ph), p-P-Phenylacetate ester (COCH$_2$C$_6$H$_4$-p-P), Diphenylacetate ester (COCHPh$_2$), Nicotinate ester, 3-Phenylpropionate ester (COCH$_2$CH$_2$Ph), 4-Pentenoate ester (COCH$_2$CH$_2$CH=CH$_2$), 4-Oxopentanoate ester (COCH$_2$CH$_2$COCH$_3$), 4,4-(Ethylenedithio)pentanoate ester, 5-[3-Bis(4-methoxyphenyl)hydroxymethylphenoxy]levulinic acid ester, Pivaloate (COC(CH$_3$)$_3$) ester, Crotonate ester (COCH=CHCH$_3$), 4-Methoxycrotonate ester (COCH=CHCH$_2$OCH$_3$), Benzoate ester (COPh), p-Phenylbenzoate ester (COC$_6$H$_4$-p-C$_6$H$_5$), 2,4,6-Trimethylbenzoate ester (COC$_6$H$_2$-2,4,6-Me$_3$), Alkyl methyl carbonate (CO$_2$CH$_3$), Methoxymethyl carbonate (CO$_2$CH$_2$OCH$_3$), alkyl 9-fluorenylmethyl carbonate, Alkyl ethyl carbonate (CO$_2$Et), Alkyl 2,2,2-Trichloroethyl carbonate (CO$_2$CH$_2$CCl$_3$), 1,1-Dimethyl-2,2,2-trichloroethyl carbonate (CO$_2$C(CH$_3$)$_2$CCl$_3$), Alkyl 2-(trimethylsilyl)ethyl carbonate (CO$_2$CH$_2$CH$_2$SiMe$_3$), Alkyl 2-(phenylsulfonyl)ethyl caronate (CO$_2$CH$_2$CH$_2$SO$_2$Ph), Alkyl isobutyl carbonate (CO$_2$CH$_2$CH(CH$_3$)$_2$), Alkyl vinyl carbonate (CO$_2$CH=CH$_2$), Alkyl allyl carbonate (CO$_2$CH$_2$CH=CH$_2$), Alkyl p-nitrophenyl carbonate (CO$_2$C$_6$H$_4$-p-NO$_2$), Alkyl benzyl carbonate (CO$_2$Bn), Alkyl p-methoxybenzyl carbonate (CO$_2$CH$_2$C$_6$H$_4$-p-OMe), Alkyl 3,4-dimethoxybenzyl carbonate (CO$_2$CH$_2$C$_6$H$_3$-3,4-(OMe)$_2$), Alkyl o-nitrobenzyl carbonate (CO$_2$CH$_2$C$_6$H$_4$-o-NO$_2$), Alkyl p-nitrobenzyl carbonate (CO$_2$CH$_2$C$_6$H$_4$-p-NO$_2$), 2-Dansylethyl carbonate, 2-(4-Nitrophenyl)ethyl carbonate (CO$_2$CH$_2$CH$_2$C$_6$H$_4$-4-NO$_2$), 2-(2,4-dinitrophenyl)ethyl carbonate (CO$_2$CH$_2$CH$_2$C$_6$H$_3$-2,4-(NO$_2$)$_2$), 2-Cyano-1-phenylethyl carbonate (CO$_2$(C$_6$H$_5$)CHCH$_2$CN), Alkyl S-Benzyl thiocarbonate (COSCH$_2$Ph), Alkyl 4-ethoxy-1-naphthyl carbonate, Alkyl methyl dithiocarbonate (SCSCH$_3$), 2-iodobenzoate ester (COC$_6$H$_4$-2-I), 4-Azidobutyrate ester (CO(CH$_2$)$_3$N$_3$), 4-Nitro-4-methylpentanoate ester, o-(dibromomethyl)benzoate ester (COC$_6$H$_4$-o-(CHBr$_2$)), 2-Formylbenzenesulfonate ester, Alkyl 2-(methylthiomethoxy)ethyl carbonate (CO$_2$CH$_2$CH$_2$OCH$_2$SCH$_3$), 4-(Methylthiomethoxy)butyrate ester (CO(CH$_2$)$_3$OCH$_2$SCH$_3$), 2-(Methylthiomethoxymethyl)benzoate ester (COC$_6$H$_4$-2-(CH$_2$OCH$_2$SCH$_3$)), 2-(Chloroacetoxymethyl)benzioate ester, 2-[(2-chloroacetoxy)ethyl]benzoate ester, 2-[2-(Benzyloxy)ethyl]benzoate ester, 2-[2-(4-Methoxybenzyloxy)ethyl]benzoate ester, 2,6-Dichloro-4-methylphenoxyacetate ester, 2,6-Dichloro-4-(1,1,3,3-tetramethylbutyl)phenoxyacetate ester, 2,4-Bis(1,1-dimethylpropyl)phenoxyacetate ester, Chlorodiphenylacetate ester, Isobutyrate ester, Monosuccinoate ester, (E)-2-Methyl-2-Butenoate ester, o-(Methoxycarbonyl)benzoate ester, p-P-Benzoate ester, α-Naphthoate ester, Nitrate ester, Alkyl N,N,N',N'-tetramethylphosphorodiamidate, 2-Chlorobenzoate ester, 4-Bromobenzoate ester, 4-Nitrobenzoate ester, 3,5-Dimethoxybenzoate carbonate, A wild and woolly photolabile fluorescent ester, Alkyl N-phenylcarbamate, Borate ester, Dimethylphosphinothioyl ester ((S)P(CH$_3$)$_2$), Alkyl 2,4-dinitrophenylsulfenate (SC$_6$H$_3$-2,4-(NO$_2$)$_2$), Sulfate, Allylsulfonate (SOCH$_2$CH=CH$_2$), Methanesulfonate (SO$_2$Me), Benzylsulfonate (SO$_2$Bn), Tosylate (SO$_2$C$_6$H$_4$CH$_3$),2-[(4-Nitrophenyl)ethyl]sulfonate (SO$_2$CH$_2$CH$_2$C$_6$H$_4$-4-NO$_2$) |
| Amino group (RNR') | Formamide (CHO), Acetamide (Ac), Chloroacetamide (COCH$_2$Cl), Trichloroacetamide (COCCl$_3$), Trifluoroaceticacetamide (COCF$_3$), Phenylacetamide (COCH$_2$C$_6$H$_5$), 3-Phenylpropanamide (COCH$_2$CH$_2$C$_6$H$_5$), Pent-4-enamide ((O)CH$_2$CH$_2$CH=CH$_2$), Picolinamide (CO-2-pyridyl), 3-Pyridylcarboxamide (CO-3-Pyridyl), N-Benzoylphenylalanyl derivatives (COCH(NHCOC$_6$H$_5$)CH$_2$C$_6$H$_5$), Benzamide (COC$_6$H$_5$), p-Phenybenzamide (COC$_6$H$_4$-p-C$_6$H$_5$) |

TABLE 1-continued

| Functional group | Protecting group (R' = R$^8$) |
|---|---|
| Amide group (CORNR') | N-Allylamide (CH$_2$CH=CH$_2$), N-t-Butylamide (t-Bu), N-Dicyclopropylmethylamide (CH(C$_3$H$_5$)$_2$), N-Methoxymethylamide (CH$_2$OCH$_3$), N-Methylthiomethylamide (CH$_2$SCH$_3$), N-Benzyloxymethylamide (CH$_2$OCH$_2$C$_6$H$_5$), N-2,2,2-Trichloroethoxymethylamide (CH$_2$OCH$_2$CCl$_3$), N-t-Butyldimethylsilyloxymethylamide (CH$_2$OSi(CH3)$_2$-y-C$_4$H$_9$), N-Pivaloyloxymethylamide (CH$_2$CO$_2$C(CH$_3$)$_3$), N-Cyanomethylamide (CH$_2$CHN), N-Pyrrolidinomethylamide, N-Methoxyamide (OMe), N-Benzyloxyamide (OCH$_2$C$_6$H$_5$), N-Methylthioamide (SMe), N-Triphenylmethylthioamide (SCPh$_3$), N-t-Butyldiethylsilylamide (Si(CH$_3$)$_2$-t-C$_4$H$_9$), N-Triisopropylsilylamide (Si(i-Pr)$_3$), N-4-Methoxyphenylamide (C$_6$H$_4$-4-OCH$_3$), N-4-(Methoxymethoxy)phenylamide (C$_6$H$_4$(OCH$_3$)$_2$), N-2-Methoxy-1-naphthylamide (C$_{10}$H$_6$-2-OCH$_3$), N-Benzylamide (CH$_2$C$_6$H$_5$), N-4-Methoxybenzylamide (CH$_2$C$_6$H$_4$-4-OCH$_3$), N-2,4-Dimethoxybenzylamide N-3,4-Dimethoxybenzylamide (CH$_2$C$_6$HH$_3$-2,4(3,4)-(OCH$_3$)$_2$), N-2-Acetoxy-4-methoxybenzylamide (CH$_2$C$_6$HH$_3$-4-OMe-2-Ac), N-o-nitrobenzylamide (CH$_2$C$_6$H$_4$-2-NO$_2$), N-Bis(4-methoxyphenyl)methylamide (CH(C$_6$H$_4$-4-OMe)$_2$), N-Bis(4-(methoxyphenyl)phenylmethylamide (CPh—(C$_6$H$_4$-4-OMe)$_2$), N-Bis(4-methylsulfinylphenyl)methylamide (CH(C$_6$H$_4$(O)S-4-Me)$_2$), N-Triphenylmethylamide (C(C$_6$H$_5$)$_3$), N-9-Phenylfluorenylamide, N-t-Butoxycarbonylamide (CO-t-OC$_4$H$_9$), N-benzyloxycarbonylamide, N-Methoxycarbonylamide (COOMe), N-Ethoxycarbonylamide (COOEt), N-p-Toluenesulfonylamide, N-Butenylamide (CH=CHCH$_2$CH$_3$), N-[(E)-2-(Methoxycarbonyl)vinyl]amide (CH=CCO$_2$Me), N-Diethoxymethylamide (CH(OEt)$_2$), N-(1-Methoxy-2,2-dimethylpropyl)amide, N-2-(4-Methylphenylsulfonyl)ethylamide (CH$_2$CH$_2$SO$_2$C$_6$H$_4$-4-CH$_3$) |

In poly(organophosphazene)-superparamagnetic nanoparticle complex according to the present invention, a hydrophobic amino acid ester [NHCH(R$^1$)CO$_2$R$^2$ in the above Chemical Formula 1a] and a hydrophilic molecule, methoxy polyethylene glycol, having a weight-average molecular weight ranging 350 to 10,000 are introduced into a dichlorophosphazene linear polymer in order for the polymer to show the temperature sensitive and biodegradation; furthermore, amino acid, peptide, or depsipeptide ester [NH(R$^3$)(R$^4$)(R$^5$) in the above Chemical Formula 1a] being capable of controlling the degradation speed of the polymer may be partially introduced thereto.

The hydrophobic amino acid ester (NHCH(R$^1$)CO$_2$R$^2$) forms the bound-type complex by hydrophobically interacting with a hydrophobic surfactant such as oleic acid (cis-9-Octadecenoic acid, CH$_3$(CH$_2$)$_7$CH=CH(CH$_2$)$_7$COOH), and/or oleylamine (cis-1-Amino-9-octadecene, CH$_3$(CH$_2$)$_7$CH=CH(CH$_2$)$_7$CH$_2$NH$_2$) on the surface of superparamagnetic nanoparticle.

In addition, the poly(organophosphazene)-superparamagnetic nanoparticle complex according to the present invention can have a functional group by directly introducing a substitutent having a functional group such as hydroxyl group, amide group, amino group, thiol group, or carboxyl group at the side chain [NH(R$^7$)(R$^8$)(R$^9$) in Chemical Formula 1b and 1c] to the main chain of the polymer; or by introducing the main chain of the polymer with an amino acid ester or a peptide ester that the functional group is substituted with a protection group, then deprotecting or introducing a substitutent having hydroxyl group to the main chain of the polymer, and esterificating the same to change to a carboxyl group.

Furthermore, it is possible to introduce a functional group to polyphosphazene by reacting lysine, arginine, cysteine, thiolan alkylamine, or polyethylene imine, polylysine, polyarginine or protamine having the various molecular weights with a polyphosphazene having carboxylic acid.

The usable protection group may include any protection group available for commonly used for protecting each functional group (Protective groups in organic synthesis, Theodora W. Greene, Peter G. M. Wuts, Wiley-interscience, Third Edition), which can be easily selected by any one having ordinary skills in the art (see table 1).

When R$^6$, R$^9$, and R$^{10}$ introduced to the polymer include various functional groups such as hydroxyl group, amide group, amino group, carboxyl group, thiol group, vinyl group and the like, they may be covalently bound with at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group to be introduced into the polymer.

It is possible to control a ethylene (gelling ethyl showing a sol-to-gel behavior of poly(organophosphazene)-superparamagnetic nanoparticle complex according to the present invention), a gel solidity, and/or degradation speed by adjusting the kind of the hydrophobic amino acid ester, the kind of amino acid, a peptide, or depsipeptide ester capable of controlling a degradation speed, the kind of the substitutent having functional group, the chain length of the methoxypolyethylene glycol, the composition of all substitutents, the molecular weight of phosphazene-based polymer, polydispersity index, the concentration of phosphazene-based polymer solution and so on.

For example, as the composition of hydrophobic amino acid is increased, the gelation temperature is decreased. As the concentration of phosphazene-based polymer solution is increased, the gelation temperature is decreased and the gel solidity is increased. As the chain length of methoxy polyethylene glycol is longer, the gel solidity is stronger and the galation temperature is higher. The poly(organophosphazene)-superparamagnetic nanoparticle complex including depsipeptide ester is biodegraded faster than that of poly(organophosphazene)-superparamagnetic nanoparticle complex having no depsipeptide ester. The poly(organophosphazene)-superparamagnetic nanoparticle complex including substitutent having a carboxylic acid functional group is biodegraded faster than that of poly(organophosphazene)-superparamagnetic nanoparticle complex including no substitutent having a carboxylic acid functional group.

The poly(organophosphazene)-superparamagnetic nanoparticle complex according to the present invention is introduced with a hydrophobic material and a hydrophilic material. The complex may include a material for controlling the degradation speed selected from the group consisting of amino acid, peptide, and depsipeptide and/or one having a side chain of a functional group selected from the group consisting of hydroxyl, amide, amino, thiol, and carboxyl.

The complex according to the present invention has a sol-to-gel behavior at a temperature ranging from 5 to 70° C., and preferably 15 to 50° C., and my be a weight-average molecular weight ranging from 3,000 to 1,500,000.

The poly(organophosphazene)-superparamagnetic nanoparticle complex includes both the bound-type complex and the mixed-type complex.

Because the poly(organophosphazene)-superparamagnetic nanoparticle complex according to the present invention has both the biocompatibility and thermosensitivity of the phosphazene-based polymer, and imaging property of superparamagnetic nanoparticle, it can be monitored visibly for the injection or delivery to the target site, when it is used for injectable bio-material or a composition for carrying a physiologically-active material. Thus, the complex is useful for a contrast agent for MRI.

The content ratio of phosphazene-based polymer and superparamagnetic nanoparticle in the complex can be adjusted suitably depending on the desired signal intensity, and, for the bound-type complex, the amount of hydrophobic amino acid capable of hydrophobic binding in the phosphazene-based polymer. For example, in case of 100 mg of phosphazene-based polymer is used, the amount of superparamagnetic nanoparticle can be 0.05 mg to 20 mg, and preferably 1.1 mg to 10 mg based on iron content of nanoparticle. When the amount of superparamagnetic nanoparticle is less than the lower limit, it is difficult to obtain the desired distinguishable image of the target site. When the amount of superparamagnetic nanoparticle exceeds the upper limit, it can invade the constrat of surrounding tissue in the contrast image.

The bound-typed poly(organophosphazene)-superparamagnetic nanoparticle complex according to the present invention where the hydrophobic surfactant is contained on the surface of superparamagnetic nanoparticle is schematically shown in the following:

[Chemical formula 3a]

(A complex of Chemical formula 1a and and superparamagnetic nanoparticle)

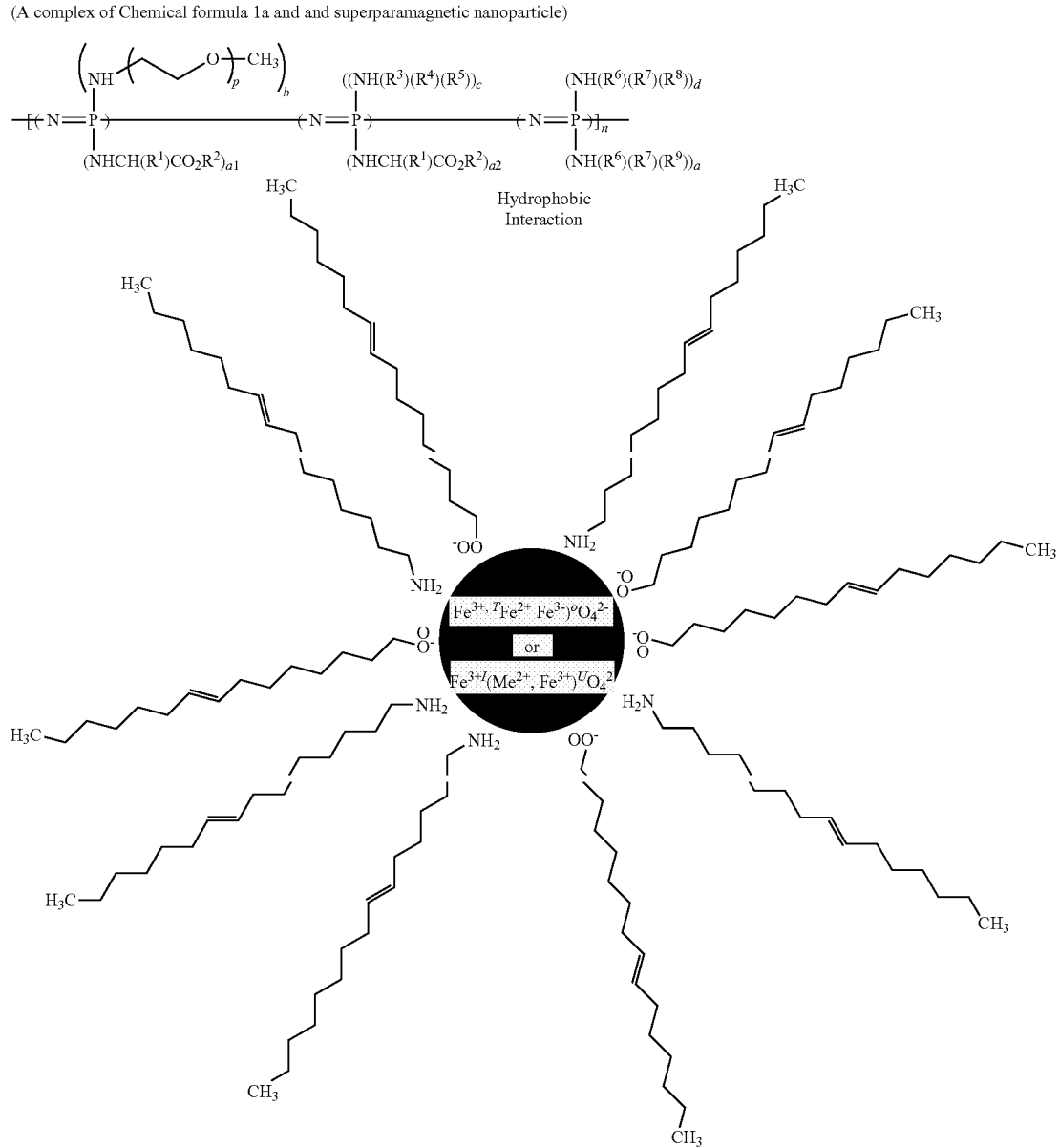

-continued
[Chemical formula 3b]
(A complex of Chemical formula 1b and and superparamagnetic nanoparticle)
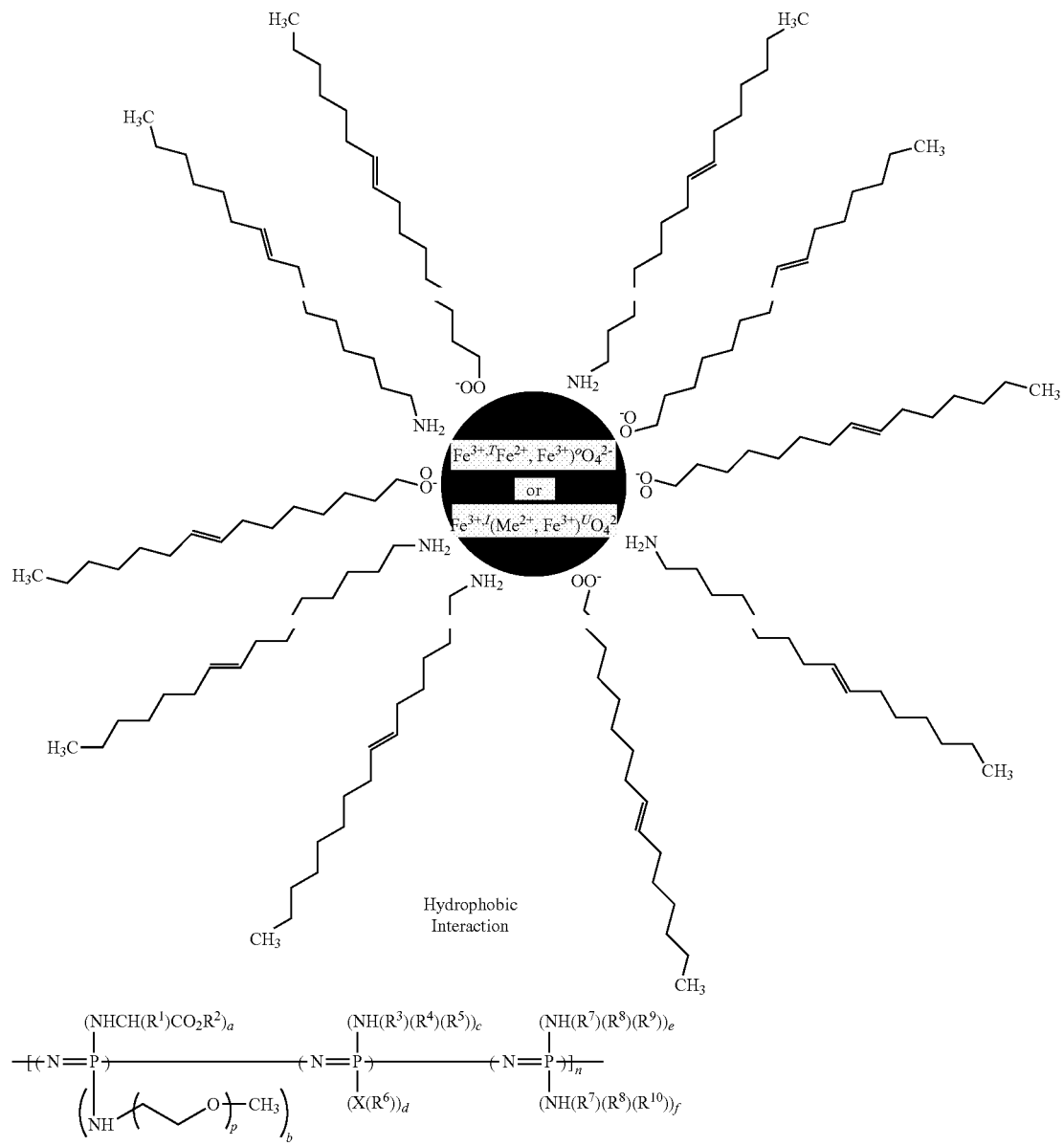
[Chemical formula 3c]
(A complex of Chemical formula 1c and and superparamagnetic nanoparticle)
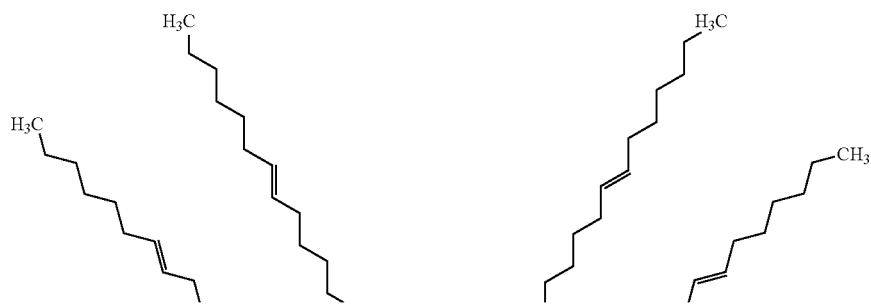

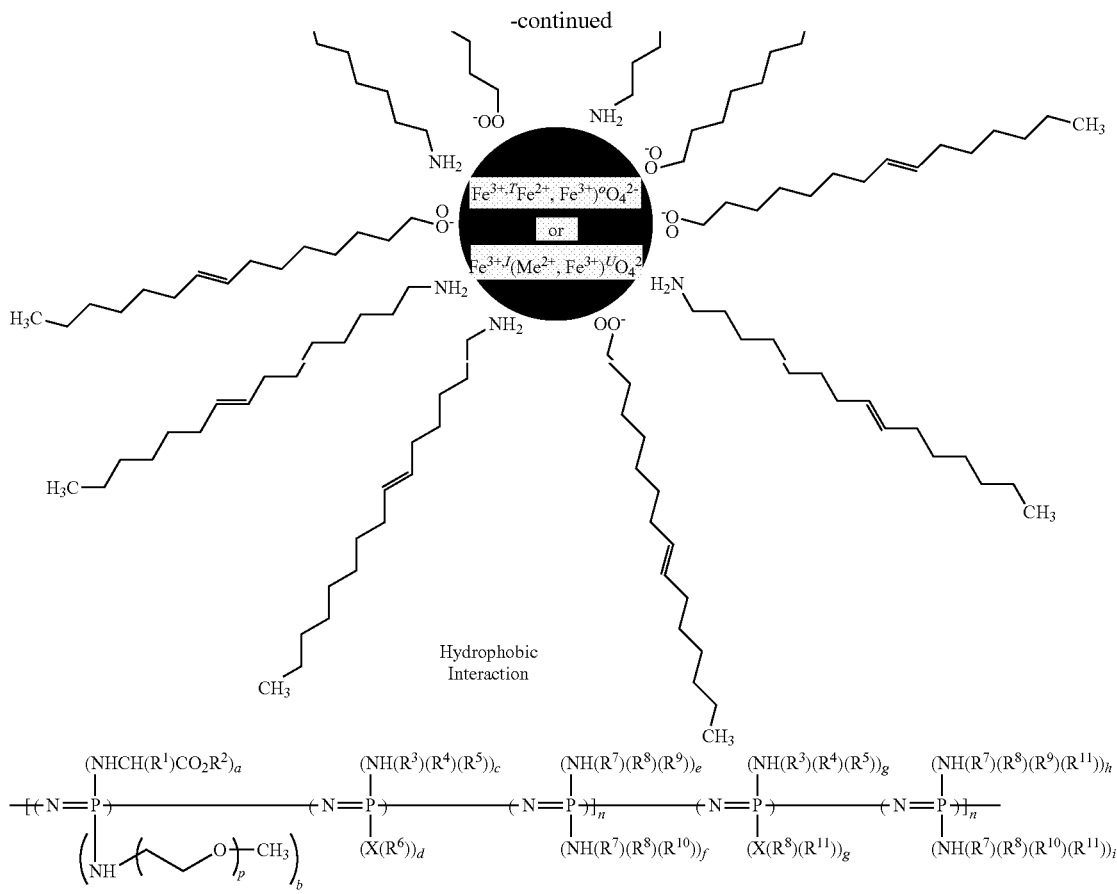

In the Chemical formulae 3a-3c, the functional group of superparamagnetic nanoparticle refers to the following hydrophobic surfactant:

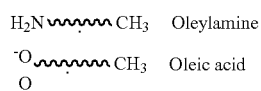

An embodiment of the present invention provides a hydrogel comprising poly(organophosphazene)-superparamagnetic nanoparticle complex and/or a solution thereof, and showing a sol-to-gel behavior depending upon the temperature change.

The solution of poly(organophosphazene)-superparamagnetic nanoparticle complex contains the complex in at least a solvent selected from the group consisting of buffer solution, acidic solution, basic solution, salt solution, water, saline, water for injection at a concentration of 1 to 50 wt %, and preferably 3 to 30 wt %. The content of superparamagnetic nanoparticle can be 0.5 to 50 μM/mL, and preferably 10 to 25 μM/mL, based on iron content of nanoparticle. When the amount of superparamagnetic nanoparticle is less than the lower limit, it is difficult to obtain the desired distinguishable image of the target site. When the amount of superparamagnetic nanoparticle exceeds the upper limit, it can invade the constrat of surrounding tissue in the contrast image. The hydrogel including poly(organophosphazene)-superparamagnetic nanoparticle complex according to the present invention has a sol-to-gel behavior at a temperature ranging from 5 to 70° C., and preferably 15 to 50° C., and may have a gel phase in the body temperature. The hydrogel can be used for various injectable bio-material, a composition carring a physiologically-active material, a MRI contrast agent, and the like.

In the hydrogel, when the phosphazene-based polymer of the complex is represented by Chemical formula 1b and 1c, the chemical bond can be formed by at least a method selected from the following five methods:

1) use of a mixed solution of a bound-typed poly(organophosphazene)-superparamagnetic nanoparticle complex including a thiol substituent and a phosphazene-based polymer including a vinyl substituent; a mixed solution of a phosphazene-based polymer including a thiol substituent and a poly(organophosphazene)-superparamagnetic nanoparticle complex including a vinyl substituent; and/or a mixed solution of at least a poly(organophosphazene)-superparamagnetic nanoparticle complex including a thiol substituent and at least a poly(organophosphazene)-superparamagnetic nanoparticle complex including a vinyl substituent, 2) UV-radiation, 3) addition of crosslinking agent, 4) addition of additive, and 5) addition of catalyst.

First of all, 1) in case of a mixed solution of at least a poly(organophosphazene)-superparamagnetic nanoparticle complex including a thiol substituent and at least a poly(organophosphazene)-superparamagnetic nanoparticle complex including a vinyl substituent, the chemical crosslinking bond may be formed by mixing at least a solution of the complex including a thiol substituent as $R^6$ and/or $R^{10}$ of Chemical formula 1b and 1c, and at least a solution of the complex including a vinyl substituent as $R^6$ and/or $R^{10}$ of Chemical formula 1b and 1c and performing the Michael-addition reaction between the thiol substituent and the vinyl substituent. At this reaction, at least a photoinitiator, at least a crosslinking agent and/or at least an additive are further added to form or accelerate the crosslinking bond formation.

In case of 2) UV radiation, the poly(organophosphazene)-superparamagnetic nanoparticle complex including a vinyl substituent as $R^6$ and/or $R^{10}$ of Chemical formula 1b and 1c is capable of forming the chemical crosslinking bond by UV-radiation, and thus can form the chemical bond by UV-radiation and optionally the addition of photoinitiator. Accordingly, the hydrogel may contain at least a solution of poly(organophosphazene)-superparamagnetic nanoparticle complex represented by Chemical formula 1b and 1c, and the photoinitiator. The photoinitiator can be contained in an amount of $1 \times 10^{-6}$ to 10 wt % and preferably $1 \times 10^{-3}$ to 1 wt % based on the weight of poly(organophosphazene)-superparamagnetic nanoparticle complex. When the amount of photo-initiator is less than the range, it is impossible to obtain the desirable effects of photo-initiator; on the other hand, when the amount is more than the range, it affects the effect of the effective ingredients and the physical property of the polymer showing the sol-to-gel behavior.

The photo-initiator useful in the present invention may include any compounds as long as it can form a radical by being irradiated, for example, it may be at least one selected from the group consisting of ketone-based compound, phosphine oxide-based compound, an alkylester-based compound, benzoyl-based compound, titanate, iodonium salt, dibenzoyl-based compound, thiocarbonate-based compound, dion-based compound, and potassium sulfate. More preferably, the photoinitiator is at least one selected from the group consisting of benzoyl peroxide, 2,2-dimethoxy-2-phenyl acetophenone, 2-hydroxy-1-[4-(2-hydroxytoxy)phenyl]-2-methyl-1-propanone, acylphosphineoxide-based compound, methylbenzoylformate, oxy-phenyl-acetic acid 2-[2-oxo-2-phenyl-acetoxy-ethoxy]ethyl ester, oxy-phenyl-acetic 2-[2-hydroxy-ethoxy]-ethyl ester, α,α-dimethoxy-a-phenylacetophenone, 2-benzyl-2-(dimethylamino)-1-[4-(4-morpholinyl)phenyl]1-butanone, benzophenone, 2-hydroxy-4'-(2-hydroxyethoxy)-2-methylpropinophenone, 1-hydroxycyclohexyl-phenyl-ketone, 2-methyl-1-[4-(methylthio)phenyl]-2-(4-morpholinyl) 1-propanone, 1-[4-(2-hydroxyethoxy)-phenyl]-2-hydroxy-2-methyl-1-propan-1-one, 2-hydroxy-2-methyl-1-phenyl-1-propanone, diphenyl (2,4,6-trimethylbenzoyl)-phosphine oxide, phosphine oxide, phenyl bis(2,4,6-trimethyl benzoyl), bis(eta 5-2,4-cyclopentadien-1-yl)titanium, bis[2,6-difluoro-3-(1H-pyrrol-1-yl)phenyl]titanium, iodonium, (4-methylphenyl)[4-(2-methylpropyl)phenyl iodonium salt, hexafluorophosphate iodonium salt, dibenzoyl disulfide-based compound, diphenyl thiocarbonate, 2,2'-azobisisobutynonitrile, camphorquinone (camphorquinone), eosine dye (dye eosin), potassium persulfate, potassium peroxodisulfate, and so on.

In a case of poly(organophosphazene)-superparamagnetic nanoparticle complex that $R^6$ and/or $R^{10}$ is a substituent having a thiol group in Chemical Formulae 1b and 1c, it can form cross-linking by irradiating the ultraviolet and adding the photo-initiator together with adding a cross-linking agent having a vinyl group being capable of forming the cross-linking with the thiol group.

3) When it forms chemical cross-linking by the cross-linking agent, the hydrogel of the present invention may include at least one poly(organophosphazene)-superparamagnetic nanoparticle com represented by Chemical Formulae 1b and 1c and at least one cross-linking agent selected from the group consisting of a thiol-based cross-linking agent and a vinyl-based cross-linking agent. The thiol-based cross-linking agent can form a chemical cross-linking by carrying out a Michael-addition-type reaction with the vinyl group present in the posphazene polymer; the vinyl-based cross-linking agent can form a chemical cross-linking by carrying out a Michael-addition-type reaction with each vinyl group or thiol group present in the poly(organophosphazene)-superparamagnetic nanoparticle complex. The added amount of cross-linking agent may ranges from $1 \times 10^{-6}$ to 30 wt % and preferably $1 \times 10^{-3}$ to 10 wt % based on the total weight of poly(organophosphazene)-superparamagnetic nanoparticle complex. When the amount of cross-linking agent is less than the range, it is impossible to obtain the desirable effects of cross-linking agent; on the other hand, when it is more than the range, it may affect on the effects of the effective ingredient and/or the sol-to-gel behavior physical property of the polymer.

The cross-linking agent useful in the present invention may include any material as long as it can carry out a Michael-addition-type reaction with a thiol or vinyl group of the Chemical Formulae 1b and 1c, so it can include any material having two or more thiol group and/or vinyl group. The cross-linking agent may be at least one compound having two or more thiol and/or vinyl, for example, a thiol-containing compound such as a thiol-based compound, a dithiol-based compound, and a mercapto-based compound, and a vinyl-containing compound such as sulfur-containing amino acid, sulfur-containing oligopeptide, an acrylate-based compound, a diacrylate-based compound, a triacrylate-based compound, a tetraacrylate-based compound, a pentaacrylate-based compound, a hexaacrylate-based compound, a metacrylate-based compound, a dimetacrylate-based compound, a (di)vinyl-based compound, a protoporphyin-based compound, a (di)vinyl-polyethyleneglycol-based compound, a (di)vinylsulfone-polyethyleneglycol-based compound, a diol-based compound, an allyl-based compound, a diallyl-based compound, a triallyl-based compound, and so on.

More preferably, the cross-linking agent may be at least one selected from the group consisting of toluene-3,4-dithiol, 4-amino-4H-1,2,4-triazole-3,5-dithiol, (1,2,4) thiadiazole-3,5-dithiol, 5-(4-chloro-phenyl)-pyrimidine-4,6-dithiol, 7-H-purine-2,6-dithiol, M-carborane-1,7 dithiol, O-carborane-1,2-dithiol, 1,3,4-thiadiazole, 1,6-hexanedithiol, 2,5-dithiol, benzene-1,2-dithiol, benzene-1,3-dithiol, biphenyl-4,4'-dithiol, bismuthiol, 2,3-dimercapto-1-propane sulfonic acid sodium salt monohydrate, 2,4-dimercapto-5-methyl pyrimidine, 2,6-dimercapto-7-methyl purine, 2,8-dimercapto-6-hydroxy purine, 6,8-dimercapto-2-hydroxy purine, 2,2'-(ethylenedioxy)diethane thiol, 1,3-dimercapto-1-propanol, 1,2-ethanedithiol, ethylene glycol dithioacetate, 1,5-dimercaptopentane, 1,3-propanedithiol, dimercaptomethane, pentaerythritol tetrakis(2-mercaptopropinonate), pentaerythritol tetrakis(3-mercaptopropinonate), trimethylolpropane tris(2-mercaptoacetate), trimethylolpropane tris(3-mercaptoacetate), dithiothreitol, thiol-substituted poly(ethylene glycol) derivatives such as a poly(ethylene glycol)-dithiol-based compound having a molecular weight of 200 to 2,500, a N-thiol-glycylglycylglycyl-terminated poly(ethylene glycol)-based compound, a 3-arm poly(ethylene glycol)-thiol-based compound having a molecular weight of 1,000 to 20,000, a 4-arm poly(ethylene glycol)-thiol-based compound having a molecular weight of 2000 to 20,000, a 8-arm poly(ethylene glycol)-thiol-based compound having a molecular weight of 10,000 to 40,000, thiol-substituted polymers such as poly(ethylene glycol-2-mercaptosuccinic acid) having a molecular weight of 200 to 25,000, biscysteine-oligopeptide, poly(ethylene glycol) derivatives having an acrylate substituent such as propylene glycol glycerolate diacrylate, di(ethylene glycol)diacrylate, tri(propylene glycol)diacrylate, tetra (ethylene glycol)diacrylate, tri(propylene glycol)glycerolate diacrylate, trimethylolpropane benzoate diacrylate, trimethylolpropane etoxylate methyl ether diacrylate, bisphenol A propoxylate diacrylate, bisphenol A propoxylate glycerolate diacrylate, bisphenol F etoxylate diacrylate, fluorescein O,O'-diacrylate, neopentyl glycol diacrylate, neopentyl glycol propoxylate diacrylate, pentaerythritol diacrylate monostearate, ethylene diacrylate, oxydiethylene diacrylate, 3-hydroxy-2,2-dimethylpropyl 3-hydroxy-2,2-dimethylpropinonate diacrylate, glycerol 1,3-diglycerolate diacrylate, 1,3-butanediol diacrylate, 1,4-butanediol diacrylate, 1,6-hexanediol diacrylate, 1,6-hexanediol etoxylate diacrylate, 1,6-hexanediol propoxylate diacrylate, bisphenol A etoxylate diacrylate having a molecular weight of 200 to 40,000, bisphenol A glycerolate diacrylate, pentaerythritol propoxylate triacrylate, pentaerythritol tetraacrylate, pentaerythritol triacrylate, trimethylpropane deoxylate triacrylate, trimethylolpropane propoxylate triacrylate, trimethylolpropane triacrylate, poly(ethylene glycol)triacrylate having a molecular weight of 200 to 2,500, poly(ethylene glycol)tetraacrylate having a molecular weight of 200 to 2,500, poly(ethylene glycol) octaacrylate having a molecular weight of 200 to 2,500, acrylated 1,6-bis(p-carboxylphenoxy)hexane, acrylate 1,3-bis(p-carboxylphenoxy)propane, acrylate sebacic acid, poly(propylene glycol)diacrylate having various molecular weights, a poly(ethylene glycol)-acrylate-based compound having a molecular weight of 200 to 2,500, a N-acrylate-glycylglycylglycyl-terminated poly(ethylene glycol)-based compound, a 3-arm poly(ethylene glycol)-acrylate-based compound having a molecular weight of 1,000 to 20,000, a 4-arm poly(ethylene glycol)-acrylate-based compound having a molecular weight of 2000 to 20,000, a 8-arm poly(ethylene glycol)-acrylate-based compound having a molecular weight of 10,000 to 40,000, a polymer having an acrylate substituent such as poly(ethylene glycol)-b-poly(lactic acid)-diacrylate having a molecular weight of 2,000 to 40,000, poly(ethylene glycol)-b-poly(glycolid)-diacrylate having a molecular weight of 2,000 to 40,000, poly(ethylene glycol)-b-poly(alpha-hydroxyl acid)-diacrylate having a molecular weight of 2,000 to 40,000, poly(ethylene glycol) derivatives having a metacrylate substituent, ethylene glycol dimetacrylate, bisphenol A dimetacrylate, 1,3-bis(3-metaacryloxyloxypropyl)-1,1,3,3-tetramethyldisiloxane, 1,3-butanediol dimetacrylate, 1,4-butanediol dimetacrylate, bisphenol A etoxylate dimetacrylate, bisphenol A glycerolate dimetacrylate, di(ethylene glycol)dimetacrylate, diurethane dimetacrylate, fluorescein O,O'-dimetacrylate, glycerol dimetacrylate, neopentyl glycol dimetacrylate, ethylene dimetacrylate, oxydiethylene dimetacrylate, di(ethylene glycol)dimetacrylate, poly(lauryl metacrylate-co-ethylene glycol dimetacrylate) having a molecular weight of 200 to 40,000, poly(methyl metacrylate-co-ethylene glycol dimetacrylate) having a molecular weight of 200 to 40,000, poly(propylene glycol) dimetacrylate having a molecular weight of 200 to 2,500, tetraethylene glycol dimetacrylate, triethylene glycol dimetacrylate, 2,2-bis[4-(2-hydroxy-3-methacryloyloxypropyl)phenyl]propane, etoxylate 2,2-bis[4-(2-hydroxy-3-metaacryloyloxypropyl)phenyl]propane, 1,6-bis-[2-metaacryloyloxyethoxycarbonylamino]2,4,4-trimethylhexane, dodecanediol dimetacrylate, trimethylolpropane trimetacrylate, metacrylated 1,6-bis(p-carboxylphenoxy)hexane, metacrylate 1,3-bis(p-carboxylphenoxy)propane, metacrylate sebacic acid, a poly(ethylene glycol)-metacrylate-based compound having a molecular weight of 200 to 2,500, a N-metacrylate-glycylglycylglycyl-terminated poly(ethylene glycol)-based compound, a 3-arm poly(ethylene glycol)-metacrylate-based compound having a molecular weight of 1,000 to 20,000, a 4-arm poly(ethylene glycol)-metacrylate-based compound having a molecular weight of 2000 to 20,000, a 8-arm poly(ethylene glycol)-metacrylate-based compound having a molecular weight of 10,000 to 40,000, a polymer having a metacrylate substitutent such as poly(ethylene glycol)-b-poly(lactic acid)-dimetacrylate having a molecular weight of 200 to 40,000, poly(ethylene glycol)-b-poly(glycolid)-dimetacrylate having a molecular weight of 200 to 40,000, poly(ethylene glycol)-b-poly(a-hydroxylic acid)-dimetacrylate having a molecular weight of 200 to 40,000, diethylene glycol divinyl ether, triethylene glycol divinyl ether, divinylbenzene, poly(1,4-butanediol)divinyl ether, polytetrahydrofuran divinyl ether, 1,6-hexanediol divinyl ether, 1,1,3,3,-tetramethyl-1,3-divinyldisiloxane, 1,3-divinyltetramethyldisiloxane, 1,4-pentadiene-3-ol, 1,4-divinyl-1,1,2,2,3,3,4,4-octamethyltetrasilane, 2,5-divinyltetrahydropyran, 3,9-divinyl-2,4,8,10-tetraoxaspiro[5,5]undecane, 3,6-divinyl-2-methyltetrahydrofuran, divinylphenylphosphine, poly(ethylene glycol)divinyl ether having a molecular weight of 200 to 2,500, poly(styrene-co-bromostyrene-co-divinylbenzene), poly(styrene-co-divinylbenzene), protoporphyin IX, protoporphyin IX dimethyl ester, protoporphyin IX disodium salt, protoporphyin IX zinc, molecular weight 1,000 to 20,000̲ 3-arm poly(ethylene glycol)-vinyl-based compound, a 4-arm poly(ethylene glycol)-vinyl-based compound having a molecular weight of 2000 to 20,000, a 8-arm poly(ethylene glycol)-vinyl-based compound having a molecular weight 10,000 to 40,000, triallyl-1,3,5-triazine-2,4,6-1H, 3H, and 5H-trione, trimethylopropane diallyl ether, 1,6-hexadiene, divinyl sulfoxide, α,ω-divinyl sulfone-poly(ethylene glycol), vinyl sulfone-3-arm poly(ethylene glycol) having a molecular weight of 1000 to 20,000, vinyl sulfone-4-arm poly(ethylene glycol) having a molecular weight of 2000 to 20,000, vinyl sulfone-8-arm poly(ethylene glycol) having a molecular weight of 10,000 to 40,000, and 1,6-hexanediol di-(endo, exo-norborne-2-en-5-carboxylate), and so on.

4) In case that the chemical crosslinking is formed by adding the additive, a mixed solution of at least one poly(organophosphazene)-superparamagnetic nanoparticle complex that includes a thiol substituent as $R^6$ and/or $R^{10}$ of Chemical formula 1b and 1c, and at least one poly(organophosphazene)-superparamagnetic nanoparticle complex that includes a vinyl substituent as $R^6$ and/or $R^{10}$ of Chemical formula 1b and 1c, or a solution of at least one poly(organophosphazene)-superparamagnetic nanoparticle complex that includes a thiol substituent as $R^6$ and/or $R^{10}$ of Chemical formula 1b and 1c can form the crosslinking bond by adding the additive. The amount of additives can be $1\times10^{-6}$ to 30 wt % and preferably $1\times10^{-3}$ to 1 wt %, based on the weight of poly(organophosphazene)-superparamagnetic nanoparticle complex. When the amount of additive is less than the range, it is impossible to obtain the desirable effects of additive; on the other hand, when it is more than the range, it may affect on the effects of the effective ingredient and/or the sol-to-gel behavior physical property of the polymer.

The additive useful in the present invention may include any material as long as it can accelerate the crosslinking reaction formed between a thiol and vinyl group, or thiol groups of the Chemical Formulae 1b and 1c. For examples, the additives may be any compounds adjusting the pH to weak base such as sodium hydroxide, ammonia, potassium hydroxide, triethylamine, sodium phosphate, TRIS base, and 4-(2- hydroxyethyl)-1-piperazineethanesulfonic acid (HEPES); catalysts such as hydrogen peroxide and ammonium peroxide; and/or an organic solvent such as DMSO.

In addition, 5) when the cross-linking is formed by enzyme, the hydrogel according to the present invention may include at least one poly(organophosphazene)-superparamagnetic nanoparticle complex that includes a thiol substituent as $R^6$ and/or $R^{10}$ of Chemical formula 1b and 1c and oxydoreductase enzymes and/or hydrogen peroxide solution. In this case, the oxydoreductase enzymes refers to all enzymes being carrying out an enzyme-substrate reaction with tyramine or tyrosine present in the phosphazene-based polymer so as to form a enzymatic cross-link, for example, it may include at least one selected from the group consisting of transglutaminase, laccase, bilirubin oxidase (BOD), manganese (II), hematin, horseradish peroxidase, and so on. It is preferable that it includes horseradish peroxidase. The hydrogen peroxide functions catalysis and promotes the reaction together with the oxydoreductase. The enzyme is added in an amount of $1 \times 10^{-6}$ to 200 wt %, and preferably $1 \times 10^{-3}$ to 100 wt % based on the total weight of phosphazene-based polymer. When the amount of enzyme is less than the range, it is impossible to obtain a desirable enzyme effect; on the other hand, when it is more than the range, it affects on the desirable effect of an effective ingredient and/or the sol-to-gel behavior physical property of the polymer of the present invention.

The hydrogel shows a sol-to-gel behavior depending on the temperature change, and excellent gel solidity. Because the hydrogel with or without the crosslinking bond becomes a gel in the body temperature, the hydrogel injected into a body forms gel phase with three dimensional structure. Particularly, in case that the hydrogel can forms the crosslinking bond, the crosslinking bond is formed in the hydrogel by carrying out UV radiation and/or addition of crosslinking agent, thereby providing excellent gel solidity inside the body. Moreover, the gel solidity can maintain two months or longer, and preferably one year or longer.

The poly(organophosphazene)-superparamagnetic nanoparticle complex including the chemical crosslinking bond can be considered to have the same applications as those of conventional biomaterial which are disclosed in Korean patent application No. 10-2006-0107230, PCT international application No. PCT/KR2006/004573, and Korean patent application No. 10-2008-0040413. The conventional biomaterials satisfy the sufficient gel solidity used for the biomaterial injected into a body; for examples, a biomaterial for plastic surgery and orthopedic surgery such as a filler, a biomaterial for tissue engineering such as an artificial cartilage, dental biomaterial, a biomaterial for preventing vascular adhesion such as a stent, a biomaterial for preventing a vessel adhesion, a biomaterial used for vascular occlusion and so on.

When the physiologically-active material is simply mixed in the poly(organophosphazene)-superparamagnetic nanoparticle complex including the chemical crosslinking bond and/or the hyrogel containing the complex, it is possible to prevent the large amount of drug releasing at an early stage due to the dense infrastructure, compared to the hydrogel without the crosslinking bond. The hydrogel that a physiologically-active material binds covalently to poly(organophosphazene)-superparamagnetic nanoparticle complex represented by Chemical formula 1c can release the physiologically-active material continuously and effectively compared to the hydrogel mixed physiologically-active material and poly(organophosphazene)-superparamagnetic nanoparticle complex and has an excellent property of carrying the physiologically-active material, because the drug release speed of hydrogel is controlled by the dissociation speed of the covalent bond.

The chemical crosslinking bond of hydrogel according to the present invention makes the hydrogel show a sol-to-gel behavior depending on the temperature change and have a sufficient gel solidity required for various biomaterial applications; and provides denser network structure and smaller-sized hole, thereby maintaining the sufficient solidity and volume for a long time. In addition, after the hydrogel of the present invention is injected into a body, in vivo behavior of hydrogel and subsequent drug release tendency can be monitored by using non-invasive MRI with high resolution in real time outside the body.

In addition, the poly(organophosphazene)-superparamagnetic nanoparticle complex and/or the hydrogel containing the complex can contribute to the improvement in biocompatibility and function of biomaterial due to the supported or covalently-bound physiologically-active material. In the use of biomaterial for carring the physiologically-active material, the covalent bond between physiologically-active material and the polymer suppresses the excessive drug release at early stage. Because the breakage of the covalent bond releases the bound physiologically-active material, the release rate of physiologically-active material can be controlled by the kind of covalent bond.

An embodiment of the present invention provides a composition for carrying a physiologically-active material comprising a poly(organophosphazene)-superparamagnetic nanoparticle complex and/or a hydrogel including the poly(organophosphazene)-superparamagnetic nanoparticle complex.

Another embodiment of the present invention provides a carrier for physiologically-active material a comprising a poly(organophosphazene)-superparamagnetic nanoparticle complex and/or a hydrogel including the poly(organophosphazene)-superparamagnetic nanoparticle complex; and a physiologically-active material.

The physiologically-active material to be delivered can be supported by simple mixing in poly(organophosphazene)-superparamagnetic nanoparticle complex or hydrogel, or can be covalently-bound one ($R^{11}$) as represented by Chemical formula 1c.

The physiologically-active material what is carried in a simple mixture is at least one drug selected from the group consisting of protein, polypeptide, peptide, vaccine, gene, hormone, anti-cancer drug, angiogenesis inhibitor, and/or at least one therapeutic cell.

The kinds of drugs such as protein, polypeptide, peptide, vaccine, gene, hormone, anti-cancer drug, and angiogenesis inhibitor are the same as defined in $R^{11}$ of Chemical formula 1c.

The therapeutic cell can be at least one selected from the group consisting of preosteoblast, chondrocyte, umbilical vein endothelial cell (UVEC), osteoblast, adult stem cell, schwann cell, oligodendrocyte, hepatocyte, mural cell (treated in combination of UVEC), myoblast, insulin secreting cell, endothelial cell, smooth muscle cell, fibroblast, β cell, endodermal cell, hepatic stem cell, juxraglomerular cell, skeletal muscle cell, keratinocyte, melanocyte, langerhans cell, merkel cell, dermal fibroblast, preadipocyte, and adipocyte.

When the physiologically-active material is simply mixed in a composition for carrying a physiologically-active material, the physiologically-active material is contained in the carrier at an amount of $1 \times 10^{-8}$ to 50 vol %, and preferably $1 \times 10^{-4}$ to 20 vol %, based on the total volume of the composition. In addition, when the cell is used as physiologically-active material, the cell is contained in an amount of $1 \times 10^{-8}$ to 50 vol % based on the total volume of the composition. When the drug or cell is less than the range, it is impossible to obtain the desirable effects of additive; on the other hand, when it is more than the range, it may affect on the effects of the effective ingredient and/or the sol-to-gel behavior physical property of the polymer.

An embodiment of the present invention provides a biomaterial comprising a poly(organophosphazene)-superparamagnetic nanoparticle complex and/or a hydrogel containing a solution of the poly(organophosphazene)-superparamagnetic nanoparticle complex.

Particularly, when the phosphazene-based polymer is represented by Chemical formula 1b or 1c, and can forms the chemical crosslinking bond, the phase of complex and/or the hydrogel changes from sol to gel depending on the kinds of substituents and composition of the ingredients and the temperature change. In addition, because the phase changes from sol to gel by UV-radiation, the crosslinking agent addition, additive addition, catalyst addition, and/or the formation of chemical crosslinking bond between the substituents of phosphazene-based polymer, the sol-to-gel behavior and gel property can be easily controlled. Thus, the complex and hydrogel can be used for various industrial applications.

The biomaterial can be used for a biomaterial injected into a body; for examples, a biomaterial for plastic surgery and orthopedic surgery such as a filler, a biomaterial for tissue engineering such as an artificial cartilage, dental biomaterial, a biomaterial for preventing vascular adhesion such as a stent, a biomaterial for preventing a vessel adhesion, a biomaterial used for vascular occlusion, treatment of cancer hyperthermia and so on.

The biomaterial and/or the composition for carrying the physiologically-active material is in a sol phase at a room temperature, because of the sol-to-gel behavior caused by the chemical crosslinking bond of the bound-type poly(organophosphazene)-superparamagnetic nanoparticle complex and by the temperature change. The biomaterial and/or the composition can be easily injected by various routes such as injection, and the injected biomaterial becomes gel at the body temperature, and has increased gel solidity because of the chemical crosslinking bond of hydrogel, thereby providing various applications. The physiologically-active material including various functional groups is directly introduced into the polymer and then crosslinked, and thus improves the function and biocompatibility of biomaterial. The hydrogel of bound-type poly(organophosphazene)-superparamagnetic nanoparticle complex according to the present invention may be injected into a body by the administration such as oral administration, buccal administration, intranasal administration, intraperitoneal administration, a hypodermic injection, intramuscular injection, transdermal administration, or intratumor administration, and it is more preferable that it is administrated by a local administration such as a hypodermic injection, intramuscular injection, transdermal administration, or intratumor administration.

The physiologically-active material is contained alone in the phosphazene-based polymer, in case that the phosphazene-based polymer is represented by Chemical formula 1b and 1c and can forms chemical crosslinking bond by UV-radiation, the crosslinking agent addition, additive addition, catalyst addition, and/or the formation of chemical crosslinking bond between the substituents of poly(organophosphazene)-superparamagnetic nanoparticle complex, the physiologically-active material is mixed with the complex simultaneously, before or after UV-radiation, the crosslinking agent addition, additive addition, catalyst addition, and/or addition of poly(organophosphazene)-superparamagnetic nanoparticle including a functional group, and thus the can be supported effectively in the complex due to the chemical crosslinking bond.

The carrier for physiologically-active material including a hydrogel which comprises a poly(organophosphazene)-superparamagnetic nanoparticle complex bound covalently with physiologically-active material as represented by Chemical formula 1c, or a solution of the poly(organophosphazene)-superparamagnetic nanoparticle complex can further comprises the following additives.

By further containing various additives, the carrier for physiologically-active material such as drug and including bound-type poly(organophosphazene)-superparamagnetic nanoparticle complex, has an increased the effectiveness of carrier. When the polypepdie or protein drug is delivered, the suitable additives maintain the drug stability in the hydrogel, and control the drug release rate from the hydrogel by inducing an ioninic bond between the drug and the additives. When the cell is delivered, the additives added to hydrogel of poly(organophosphazene)-superparamagnetic nanoparticle complex increases the cell activity after delivering the cell into a body.

That is, the additives induce the various interactions such as the chemical binding (for example, ionic bond) between the poly(organophosphazene)-superparamagnetic nanoparticle or hydrogel of poly(organophosphazene)-superparamagnetic nanoparticle complex and the physiologically-active material such as drug, and thus controls the release of physiologically-active material and/or increase the in vivo activity of the physiologically-active material such as therapeutic cell. In addition, the accurate information on in vivo state of the phosphazene-based 'bound-type' magnetic polymer or hydrogel thereof used for all applications and the other materials contained the polymer or hydrogel can be obtained at any time with MRI considered as non-invasive and high-resolution analyzing method. Moreover, besides the non-invasive diagnosis using the MRI, the bound-type poly(organophosphazene)-superparamagnetic nanoparticle complex or the hydrogel thereof can be used for hyperthermia due to the thermal energy conversion of the superparamagnetic nanoparticle and thus have secondary combination therapy.

The added amount of additives may range from $1 \times 10^{-6}$ to 30 wt % and preferably $1 \times 10^{-3}$ to 10 wt % based on the total weight of carrier. When the amount of cross-linking agent is less than the range, it is impossible to obtain the desirable effects of cross-linking agent; on the other hand, when it is more than the range, it may affect on the effects of the effective ingredient and/or the sol-to-gel behavior physical property of the polymer.

The additives may be any material, as long as they can induce various interaction between the bound-type poly(organophosphazene)-superparamagnetic nanoparticle complex and physiologically-active material, and for examples, can be at least one selected from the group consisting of a cationic, anionic or neutral polymer with weight-average molecular weight of 200 to 750,000, amino acid, peptide, protein, fatty acid, phospholipid, vitamins, drug, polyethyleglycol ester, steroid, amine compound, acrylat-based copolymer, organic solvent, preservative, saccharide, polyol, sugar-containing polyol, sugar-containing amino acid, surfactant, sugar-containing ion, silicate, metal salt, and ammonium salt.

More specifically, the exemplified additives include at least one selected from the group consisting of neutral polymers (for example, polymers having a molecular weight of 200 to 750,000) such as poly(ethylene glycol), poly(vinyl pyrrolidone); cationic polymers (for example, polymers having a molecular weight of 200 to 750,000) such as poly-L-arginine, poly-L-lysine, polyethylenimine, chitosan, and protamin; anionic polymers such as polyvinylacetate (PVA), hyaluronic acid, chondroitin sulphate, dextran sulfate, heparin, and alginate; growth factors such as amiloride, procainamide acetyl-beta-methylcholine, spermine, spermidine, lysozyme, fibroin, albumin, collagen, transforming growth factor-beta (TGF-beta), fibroblast growth factor (bFGF), vascular endothelial growth factor (VEGF) and the like, and bio-materials such as bone morphogenetic proteins (BMPs), dexamethason, fibronectin, fibrinogen, thrombin, protein, dexrazoxane, leucovorin, ricinoleic acid, phospholipid, small intestinal submucosa, vitamin E, polyglycerol ester of fatty acid, Labrafil, Labrafil M1944CS, cardioxane, glutamic acid, hydroxypropyl methylcellulose, gelatin, isopropyl myristate, Eudragit, tego betain, dimyristoylphosphatidylcholine, scleroglucan and the like; organic solvents such as chromophore EL, ethanol, dimethylsulfoxide and the like; preservatives such as methylparaben: sacchrides as starch, cyclodextrin and its derivative, lactose), glucose, dextran, mannose, sucrose, trehalose, maltose, ficoll and the like; polyols such as inositol, mannitol, sorbitol, and the like; sugar-containing polyols such as sucrose-mannitol, glucose-mannitol and the like; amino acids such as alanin, arginin, glycin and the like; polymer-containing polyols such as trehalose-PEG, sucrose-PEG, sucrose-dextran and the like; sugar-containing amino acids such as sorbitol-glycin, sucrose-glycin and the like; surfactants such as poloxamers having various molecular weights, Tween 20, Tween 80, Triton X-100, sodium dodesyl sulphate (SDS), Brij and the like; sugars-containing ions such as trehalose-$ZnSO_4$, maltose-$ZnSO_4$ and the like; and salts such as silicate, NaCl, KCl, NaBr, NaI, LiCl, n-$Bu_4NBr$, n-$Pr_4NBr$, $Et_4NBr$, $Mg(OH)_2$, $Ca(OH)_2$, $ZnCO_3$, $Ca_3(PO_4)_2$, $ZnCl_2$, $Zn(O_2CCH_3)_2$ $(C_2H_3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, AgCl, $AuCl_3$, $CuCl_2$, sodium dodecyl sulphate), sodium tetradecyl sulphate), dodecyltrimethylammonium bromide), dodecyltrimethylammonium chloride), tetradecyltrimethylammonium bromide and the like.

The hydrogel of poly(organophosphazene)-superparamagnetic nanoparticle complex can be applied for hyperthermia using high frequency magnetic field. In addition, the phosphazene-based magnetic polymer having a functional group can be bound with target material and then controlled by adjusting the sol-to-gel transition temperature to inject into a body in a solution state.

Thus, an embodiment of the present invention provides a contrast agent for magnetic resonance image (MRI) comprising a hydrogel which comprises a poly(organophosphazene)-superparamagnetic nanoparticle complex or a solution of the poly(organophosphazene)-superparamagnetic nanoparticle complex. To make the complex and it's hydrogel be injectable and used for the MRI contrast agent, the poly(organophosphazene)-superparamagnetic nanoparticle complex can be preferably mixed in saline at a concentration of 1 to 3 wt %. The contrast agent is used with intravenous injection and thus must not become a gel. To prevent the gellation of complex with maintaining the efficacy, the concentration of complex in the contrast agent is in the ranges preferably. For the contrast agent be used for intravenous injection, it is preferable to bind to the target materials such as RGD to the phosphazene-based polymer.

The phosphazene-based polymer, phosphazene-based polymer including the chemical crosslinking bond and the hydrogel thereof can be synthesized according to the method disclosed in the present inventor's previous application, KR 2008-0110473A (published on Dec. 18, 2008) which is enclosed herewith for a reference. An embodiment of the present invention provides a method of preparing poly(organophosphazene)-superparamagnetic nanoparticle complex comprising the steps of preparing the phosphazene-based polymer represented by Chemical formula 1a, 1b or 1c; and mixing the produced phosphazene-based polymer with a superparamagnetic nanoparticle represented by Chemical formula 2a or 2b.

When the superparamagnetic nanoparticle has a hydrophobic surfaces such as hydrophobic surfactants of oleic acid (cis-9-Octadecenoic acid, $CH_3(CH_2)_7CH=CH(CH_2)_7COOH$), and/or oleylamine (cis-1-Amino-9-octadecene, $CH_3(CH_2)_7CH=CH(CH_2)_7CH_2NH_2$) on its surface, the bound-type complex can be formed by mixing the phosphazene-based polymer and the superparamagnetic nanoparticle via the interaction between hydrophobic surfactant and hydrophobic functional group of phosphazene-based polymer.

The 'bound-type' or 'mixed-type' complex shows a sol-to-gel behavior due to the chemical crosslinking bond and thermosensitivity depending on the temperature change, and thus the gel solidity can be improved by forming chemical crosslinking bond using UV-radiation, the crosslinking agent addition, additive addition, catalyst addition, and/or the formation of chemical crosslinking bond between the substituents of poly(organophosphazene)-superparamagnetic nanoparticle complex, after easily converting to gel by changing temperature. Thus, the complex with improved gel solidity can be used for a biomaterial injected into a body; for examples, a biomaterial for plastic surgery and orthopedic surgery such as a filler, a biomaterial for tissue engineering such as an artificial cartilage, dental biomaterial, a biomaterial for preventing vascular adhesion such as a stent, a biomaterial for preventing a vessel adhesion, a biomaterial used for vascular occlusion, treatment of cancer hyperthermia and so on. In addition, because the physiologically-active material having various functional groups can be introduced to the polymer directly, the functionality and biocompatibility of the complex can be improved increasingly which can be appropriate for the application objects. Because the pore size of hydrogel can be adjusted freely by using a chemical crosslinking, the hydrogel can have excellent supporting property of hydrophilic drugs so as to release the drugs slowly. In addition, the drug can bind directly to the complex, the drug release rate can be controlled. Thus, the complex can be used for a carrier of physiologically-active materials such as drugs. The magnetic polymer may be injected to body in a form of local injection type and/or intravenous injection type, and make hyperthermia be performed in combination of radiation treatment, chemotherapy, or surgical operation.

Besides the carrier for the physiologically-active materials such as drugs, the complex can be used for a biomaterial required for sufficient gel solidity; for examples, a biomaterial for plastic surgery and orthopedic surgery such as a filler, a biomaterial for tissue engineering such as an artificial cartilage, dental biomaterial, a biomaterial for preventing vascular adhesion such as a stent, a biomaterial for preventing a vessel adhesion, a biomaterial used for vascular occlusion. In addition, besides the high gel solidity, the hydrogel being capable of crosslinking can be bound directly with physiologically-active material having various functional groups and thus can be used as various biomaterial and increase the functionality and biocompatibility.

BRIEF DESCRIPTION OF DRAWINGS

FIG. 3-$b$) is a graph showing the magnetization degree per weight of the ferrite nanoparticle ($Fe_3O_4$, $MnFe_2O_4$, $CoFe_2O_4$, and/or $NiFe_2O_4$) constituting the temperature-sensitive phosphazene-based 'bound-type' and/or 'mixed-type' magnetic polymer according to an embodiment of the present invention, where the magnetization degree was measured by Superconducting Quantum Interference Device.

FIG. 3-$c$) is a graph of X-ray diffraction showing an atomic composition of $CoFe_2O_4$ among the ferrite nanoparticle ($Fe_3O_4$, $MnFe_2O_4$, $CoFe_2O_4$, and/or $NiFe_2O_4$) constituting the temperature-sensitive phosphazene-based 'bound-type' and/or 'mixed-type' magnetic polymer according to an embodiment of the present invention.

FIG. 3-$d$) is a photograph of transmission electron microscopy showing the size and shape of $CoFe_2O_4$ nanoparticle among the ferrite nanoparticle ($Fe_3O_4$, $MnFe_2O_4$, $CoFe_2O_4$, and/or $NiFe_2O_4$) constituting the temperature-sensitive phosphazene-based 'bound-type' and/or 'mixed-type' magnetic polymer according to an embodiment of the present invention.

EXAMPLE

Figure 1:
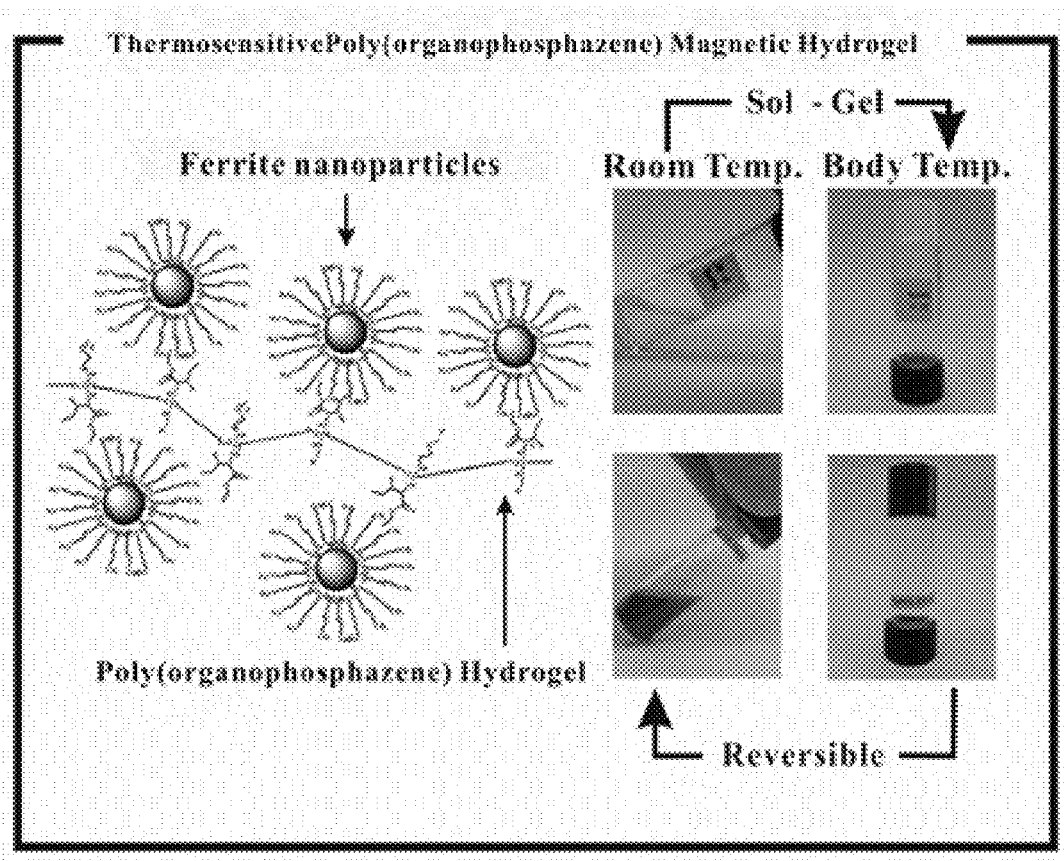
FIG. 1 is a photograph showing a hydrophobic interaction of phosphazene-based 'bound-type' magnetic polymer (left side), and a reversible sol-to-gel phase transition behavior of the temperature-sensitive phosphazene-based 'bound-type' magnetic polymer according to an embodiment of the present invention.
Figure 2:
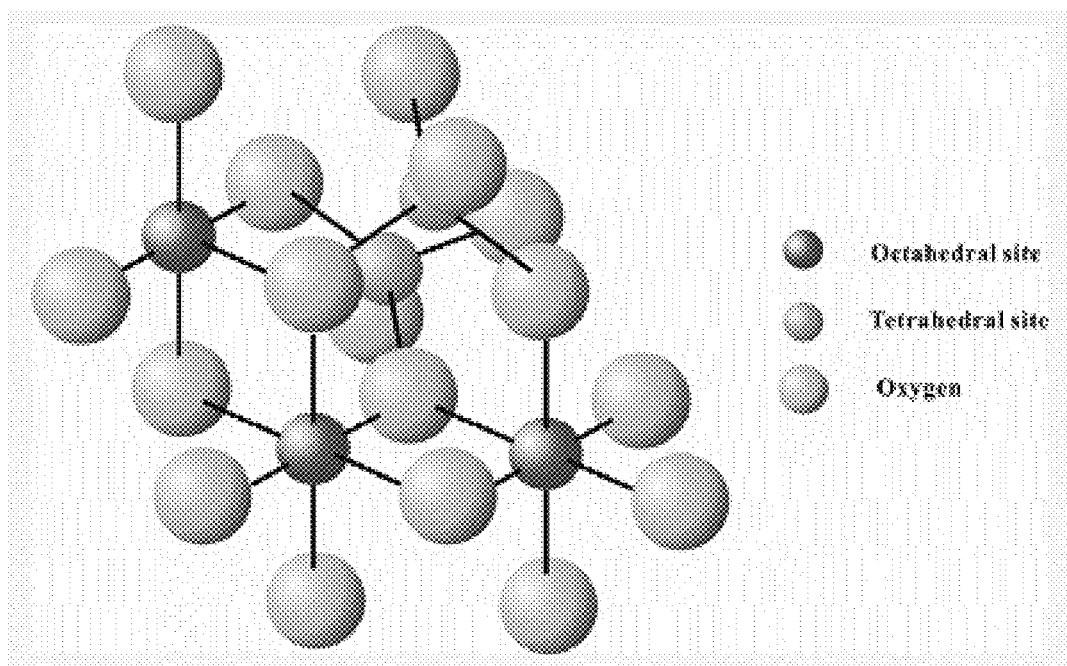
FIG. 2 is a schematic drawing showing the crystal structure of the ferrite nanoparticle ($Fe_3O_4$, $MnFe_2O_4$, $CoFe_2O_4$, and/or $NiFe_2O_4$) constituting the temperature-sensitive phosphazene-based 'bound-type' and/or 'mixed-type' magnetic polymer according to an embodiment of the present invention.

The present invention is further explained in more detail with reference to the following examples. These examples, however, should not be interpreted as limiting the scope of the present invention in any manner.

In the examples below, The nuclear magnetic resonance spectrums with hydrogen and phosphorus were respectively measured by using Varian Gemini-300, and the average molecular weight ($M_w$) is measured through gel permeation chromatography using a Waters 1515 pump and a 2410 differentiation refractometer. The gel solidity of the produced hydrogel was analyzed with Brookfield RVDV-III+ viscometer (Brookfield Engineering Laboratories, Inc.) and AR-2000 rheometer (TA Instruments, Inc.). The analysis for crystal structure of superparamagnetic nanoparticle using X-ray diffraction was performed by D/MAX-2500 (Rigaku international Corporation), The size and shape of nanoparticle using the transmission electron microscopy, and atomic composition of nanoparticle using Energy Dispersive X-ray Spectrometer were performed by Tecnai G2 (FEI Hong Kong Co., Ltd.). The magnetization degree per weight of superparamagnetic nanoparticle using Superconducting Quantum Interference Device was measured by MPMSS (Quantum Design Co.). The coordination binding state of superparamagnetic nanoparticle with hydrophilic surface was confirmed with Thermo Mattson model infinity gold FTIR (Thermo Fisher Scientific Inc.). The iron content in the magnetic polymer was measured by SOLAAR M (Thermo Fisher Scientific Inc.), The slow drug release tendency of 'mixed-type' magnetic polymer was performed by OPTIZEN 2021UV (Mecasys Co., Ltd.), in vivo NMR was analyzed by using 4.7T-Bruker Biospin for animal MRI (Bruker Biospin).

Example 1

Preparation of 'Bound-Type' Magnetic-[NP(IleOEt)$_{1.01}$(AMPEG550)$_{0.64}$(AEMA)$_{0.35}$]$_n$ with the Hydrophobic Bond of Poly[(Isoleucine Ethyl Ester)(Aminomethoxy Polyethyleneglycol 550)(Aminoethylmethacrylate)Phosphazene] and Covalt Ferrite (CoFe$_2$O$_4$) Superparamagnetic Nanoparticle 1-1) Preparation of [NP(IleOEt)$_{1.01}$(AMPEG550)$_{0.64}$(AEMA)$_{0.35}$]$_n$ Dried isoleucine ethyl ester hydrochloride salt (3.00 g, 15.54 mmol) was dissolved in 100 ml of anhydrous tetrahydrofuran, and then, triethylamine (4.65 g, 46.03 mmol) was added thereto. Poly(dichloro phosphazene)(2.00 g, 17.26 mmol) was dissolved in 50 ml of anhydrous tetrahydrofuran, and then slowly added dropwise to the obtained isoleucine ethyl ester hydrochloride salt solution in dry ice-acetone bath at −60° C., allowing to react for 48 hours with slowly increasing the temperature to the room temperature.

After checking the reaction progress by checking $^{31}$P-NMR, the solution of aminomethoxypolyethylene glycol of molecular weight 550 (4.03 g, 7.32 mmol) and triethylamine (3.63 g, 21.98 mmol) dissolved in anhydrous tetrahydrofuran (50 ml) was added dropwise to the obtained resulting product, allowing to react at the room temperature for 24 hours, and at 40-50° C. for 24 hours. After checking again the reaction progress by checking $^{31}$P-NMR, a solution of dried aminoethylmethacrylate hydrochloride salt (3.92 g, 23.92 mmol) dissolved in 10 ml anhydrous dimethylformamide, to which triethylamine (6.68 g, 47.58 mmol) was added, to the obtained reaction solution, allowing to react at the room temperature for 24 hours, and at 40-50° C. for 24 hours.

The reaction solution was filtered to remove a generated triethylamine hydrochloride salt. The remaining solution was concentrated under decompression until the solvent was mostly removed. The obtained concentrate solution was dissolved in tetrahydrofuran (10 ml) and an excess of hexane was added thereto to induce the formation of precipitation. After the process was repeated 2 or 3 times, the obtained precipitate was dissolved again in a small amount of methylalcohol. The resulting solution was put into an MWCO 12000 membrane (Spectrum Laboratories, Inc.), and dialyzed with methylalcohol at room temperature for 5 days and with distilled water for 5 days. The obtained product was dried at a low temperature, to produce poly(dichlorophosphazene) [NP(IleOEt)$_{1.01}$(AMPEG550)$_{0.64}$(AEMA)$_{0.35}$]$_n$ 7.64 g (yield 68%).

Hydrogen Nuclear Magnetic Resonance Spectrum (CDCl$_3$, ppm):
  δ=0.8-1.1 (b, —NHCH(CH(C$\underline{H}_3$)(CH$_2$C$\underline{H}_3$))COOCH$_2$CH$_3$),
  δ=1.1-1.4 (b, —NHCH(CH(CH$_3$)(C$\underline{H}_2$CH$_3$))COOCH$_2$C$\underline{H}_3$),
  δ=1.9 (s, —NHCH$_2$CH$_2$O$_2$C(C$\underline{H}_3$)C=CH$_2$)
  δ=3.4 (s, —NH(CH$_2$CH$_2$O)$_{11}$C$\underline{H}_3$),
  δ=3.5-3.9 (b, —NH(C$\underline{H}_2$C$\underline{H}_2$O)$_{11}$CH$_3$, —NHC$\underline{H}$(CH(CH$_3$)(CH$_2$CH$_3$))COOCH$_2$CH$_3$),
  δ=4.0-4.4 (b, —NHCH(CH(CH$_3$)(CH$_2$CH$_3$))COOC$\underline{H}_2$CH$_3$, —NHC$\underline{H}_2$C$\underline{H}_2$O$_2$C(CH$_3$)C=CH$_2$),
  δ=5.5 (s, —NHCH$_2$CH$_2$O$_2$C(CH$_3$)C=C$\underline{H}_2$)
  δ=6.1 (s, —NHCH$_2$CH$_2$O$_2$C(CH$_3$)C=C$\underline{H}_2$)

Phosphorus Nuclear Magnetic Resonance Spectrum (CDCl$_3$, ppm): δ 19.7

Molecular weight ($M_w$): 530000

1-2) Preparation of CoFe$_2$O$_4$ Superparamagnetic Nanoparticle (Thermal Decomposition Method)

(a) Preparation of reacting solution 1: Cobalt(II) acetylacetonate (4 mmol), 1,2-hexadecanediol (40 mmol), oleic acid (30 mmol), and oleylamine (30 mmol) were added to 120 mL of benzyl ether, and agitated well with magnetic rod at nitrogen atmosphere to produce reacting solution 1.

(b) Preparation of reacting solution 1: Fe(III) acetylacetonate (8 mmol) was dissolved in 40 mL of benzyl ether to obtain reacting solution 2.

(c) In the heating process of reacting solution 1 to 200° C., when the temperature of reacting solution 1 was about 160° C., the reacting solution 1 was added by reacting solution 2 and kept at 200° C. for 30 minutes (the keeping time was at least 30 minutes and the solution was heated sufficiently as long as possible for 3 hr or longer).

(d) After the solution was heated sufficiently at 200° C., whole reacting solution was heated at the temperature of 300° C.~310° C. for 30 minutes again (the heating time was at least 30 minutes and the solution was heated sufficiently as long as possible for 1 hr or longer). At this step, a reflux condenser was used for preventing the solvent evaporation.

(e) After reflux, the heat source was removed and the reacting solution was cooled to a room temperature spontaneously.

(f) After cooling, excess amount of anhydrous ethanl was added to the reacting solution and agitated well with a magnetic rod.

(g) The resultant solution was centrifuged at 4000 rpm for 20 minutes and then the precipitate was collected.

(h) The solvent was removed completely to leave the precipitate.

(i) The steps (f) to (h) were repeated at several times.

(j) The precipitated obtained from the centrifugation was mixed well with addition of suitable amount of hexane, oleic acid (25 mL) and oleylamine (25 mL), and (k) the unreacted precipitate was removed by centrifuging at 4000 rpm for 20 minutes and the solution dispersed in hexane was extracted.

(l) The hexane solution was added by excess anhydrous ethanol and mixed well, and then was centrifuged at 4000 rpm for 20 minutes to induce the formation of precipitation and solution except for precipitate was removed.

(m) A small amount of hexane was added to disperse the precipitate, and the dispersed hexane solution was centrifuged at 4000 rpm for 20 minutes.

(n) After centrifugation, black hexane solution excluding the precipitate was extracted (o) The extracted hexane solution was dried at a nitrogen atmosphere to obtain dry powder of $CoFe_2O_4$ nanoparticle. To keep hexane solution of the product, the solution was kept in a refrigerator.

Figure 3A:
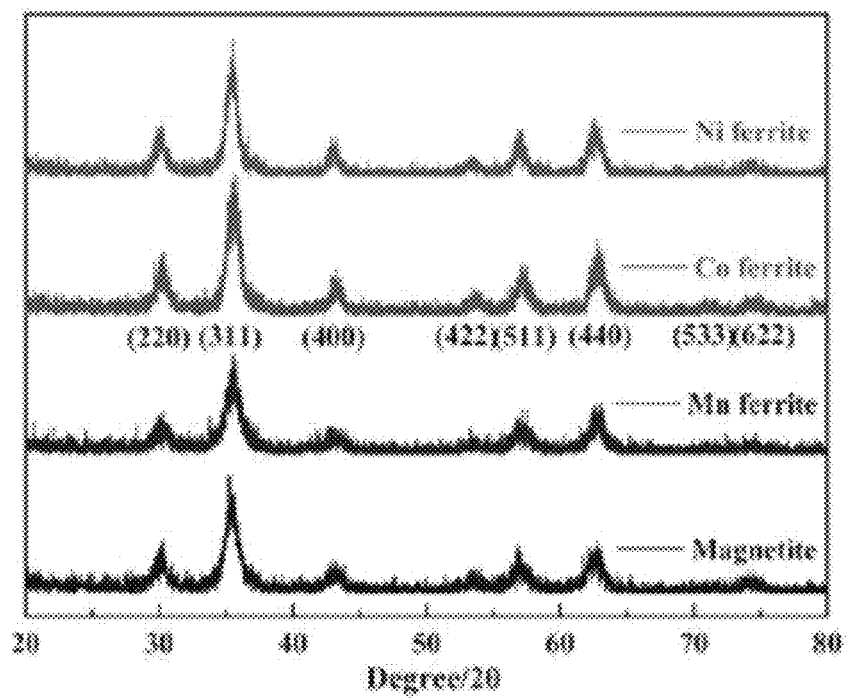
FIG. 3-$a$) is a graph confirming the crystallinity of nanoparticle with X-ray diffraction pattern of the ferrite nanoparticle ($Fe_3O_4$, $MnFe_2O_4$, $CoFe_2O_4$, and/or $NiFe_2O_4$) constituting the temperature-sensitive phosphazene-based 'bound-type' and/or 'mixed-type' magnetic polymer according to an embodiment of the present invention.
Figure 3B:
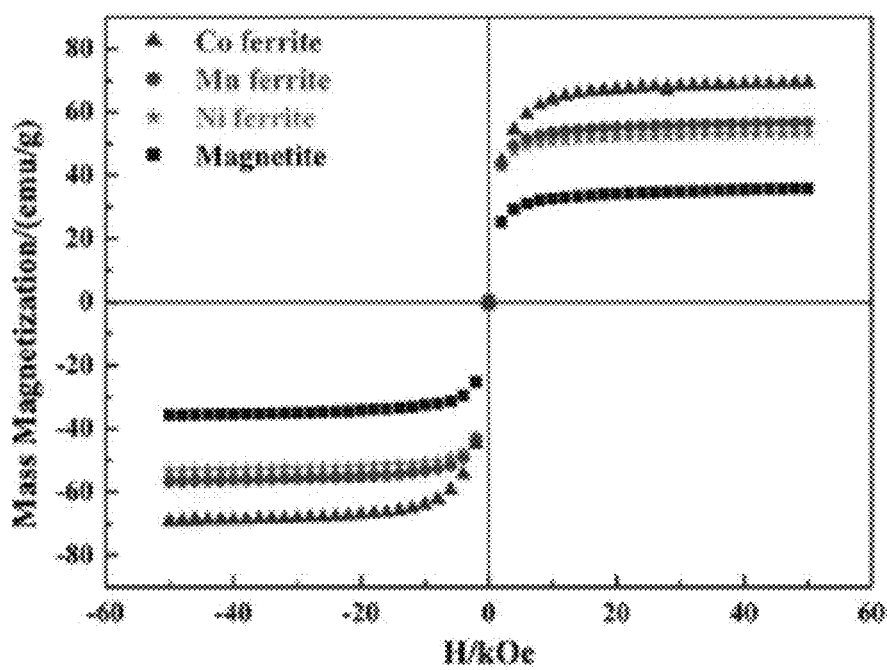
Figure 3C:
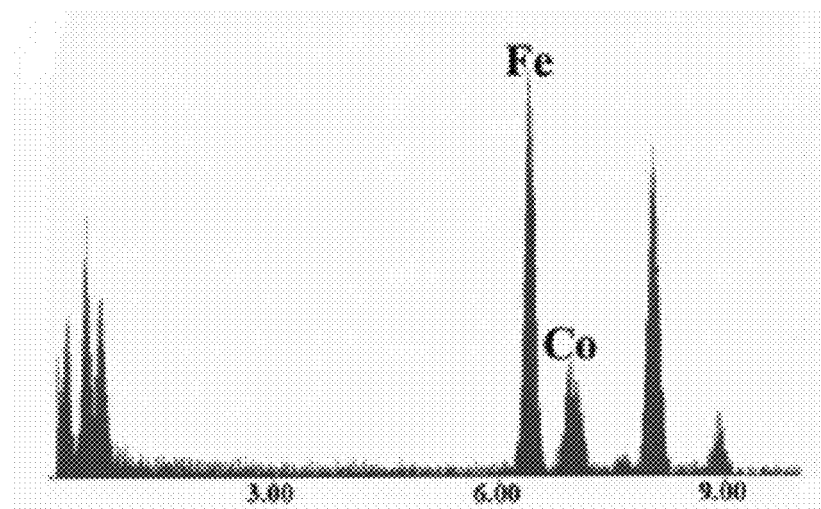
Figure 3D:
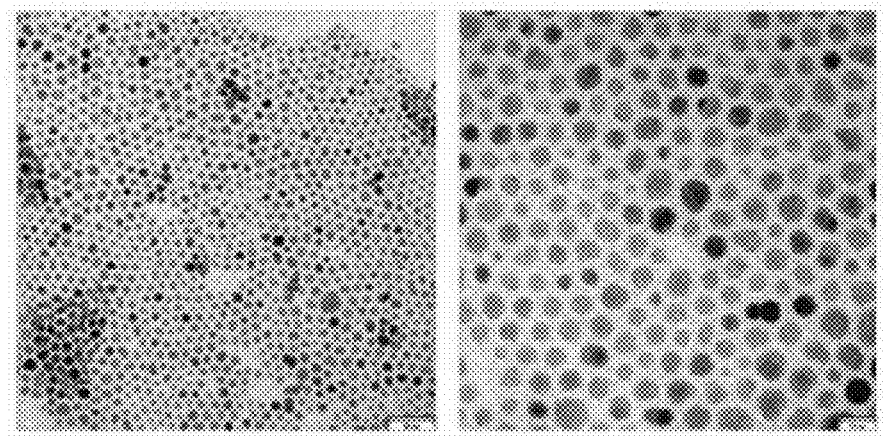

The basic physiochemical properties of obtained $CoFe_2O_4$ nanoparticle such as the crystal structure of nanoparticle, particle size and shape, atomic composition and magnetization degree were analyzed with X-ray diffraction analysis, transmission electron microscopy, disperse X-ray spectrometer, and Superconducting Quantum Interference. The shape of nanoparticle was shown in FIG. 3(d), the average particle size of the product was 7-10 nm, EDX measurement confirmed CO:Fe ratio of 19.1%:80.9%, and SQUID result confirmed that the magnetization degree of $CoFe_2O_4$ was 69.195 emu/g at 20 kOe.

1-3) Preparation of Phosphazene-Based "Bound-Type" Magnetic Polymer, Magnetic-$[NP(IleOEt)_{1.01}(AMPEG550)_{0.64}(AEMA)_{0.35}]_n$ (a) Preparation of Solution 1: The hydrogel solution (10 wt %, 20 mL) of $[NP(IleOEt)_{1.01}(AMPEG550)_{0.64}(AEMA)_{0.35}]_n$ in distilled water was prepared and kept at 0° C.~4° C.

(b) Preparation of Solution 2: 25 μmol of $CoFe_2O_4$ superparamagnetic nanoparticle was dissolved in 20 mL of hexane homogeneously, and then kept at 0° C.~4° C.

(c) Solution 2 was added to Solution 1 and two layers of solution were formed in a container (Upper layer was a hexane solution including $CoFe_2O_4$ superparamagnetic nanoparticle and lower layer was a distilled water layer including $[NP(IleOEt)_{1.01}(AMPEG550)_{0.64}(AEMA)_{0.35}]_n$).

(d) The two layers were agitated strongly with vortex for 5 minutes.

(e) After agitating, the solution was agitated with sonicator for 5 minutes under the condition that the temperature of solution did not exceed To (gellation temperature) of original hydrogel solution.

(f) After agitating with sonicator for 5 minutes, the solution was agitated again with sonicator for 10-20 seconds and then, the mixed solution was left stably to cause the layer separation at 0° C.~4° C. for 10-20 minutes.

(g) After the layer separation, the solution was maintained and left stably at the temperature of $T_{max}$ (maximum gellation temperature) of original hydrogel solution for 10 minutes to cause the lower layer to be gel.

(h) After the lower layer was a gel completely, the upper layer of hexane separated from the supernatant was removed.

(i) After removing the hexane layer, the separated lower layer became to a sol by keeping it at 0° C.~4° C., and added by sufficient amount of hexame.

(j) The unbound nanoparticle was removed by repeating the steps of (d)-(i) at several times to separate the pure product.

(k) The separated product was kept at 4° C. for 24 hr in a refrigerator.

(l) After being kept for 24 hours in a refrigerator, the product was divided into two layer again. The upper layer and lower layer were separated respectively and then centrifuged at 13000 rpm for 5 minutes. If the upper layer was separated from the lower layer, the upper layer was added by 20 mL of distilled water, and agitated with vertex, and kept at 0° C.~4° C. to induce the layer separation. After the layer separation, only lower layer was separated and centrifuged at 13,000 rpm for 5 minutes.

(m) Only pure reactant was extracted from the centrifuged product except for the precipitate and supernatant and then collected in a container.

(n) The collected product was filtered with a 0.45 μm syringe-type filter by maintaining the temperature of 0° C.~4° C. and then re-collected.

(o) The re-collected product was frozen using dryice or liquid nitrogen and then performed by freeze-drying.

(p) After completion of freeze-drying, 'bound-type' Magnetic-$[NP(IleOEt)_{1.01}(AMPEG550)_{0.64}(AEMA)_{0.35}]_n$ polymer was obtained in a gel.

(q) After preparing 10 wt % 'bound-type' magnetic polymer solution, the size and the shape of nanoparticle in 'bound-type' magnetic polymer was measured with transmission electron microscopy, and the iron content of 'bound-type' magnetic polymer was determined with atomic absorption spectroscopy. In addition, the hydrophobic bond between the nanoparticle and the polymer was confirmed by the thermal gravity analysis (TGA)

(r) The viscosity of the final product of 'bound-type' magnetic polymer was measured by viscometer, and the degradation tendency could be estimated by weight reduction assessment of gel.

(s) The physiochemical property of 'bound-type' magnetic polymer as a MRI contrast agent was checked by the phantom study using the conventional MRI apparatus for clinical use such as 1.5T, 3T, and/or 7T MRI apparatus, and/or 4.7T MRI apparatus for the animal use.

As described above, in the preparation of 'bound-type' magnetic polymer of Magnetic-[biodegradable and thermosensitive poly(organophosphazene)], the method of steps 1-2) and 1-3) in Example 1 can be applied for all biodegradable and thermosensitive poly(organophosphazene) of items ①-⑥. These examples should not be interpreted as limiting the scope of the present invention in any manner.

Example 2

Preparation of 'Mixed Type' Magnetic-$[NP(IleOEt)_{1.10}(GlyLacOEt)_{0.02}(AMPEG550)_{0.88}]_n$ by Physical Mixing Poly[(Isoleucinethylester)(Ethyl-2-(O-Glycyl)Lactate)(Aminomethoxypolyethyleneglycol 550)] with Covalt Ferrite ($CoFe_2O_4$) Superparamagnetic Nanoparticle 2-1) Preparation of $[NP(IleOEt)_{1.10}(GlyLacOEt)_{0.02}(AMPEG550)_{0.88}]_n$.

Poly(dichloro phosphazene)(2.00 g, 17.26 mmol) was dissolved in 100 ml tetrahydrofuran, and then isoleucine ethyl ester hydrochloride salt solution (4.08 g, 17.78 mmol) and triethylamine (13.98 g, 69.04 mmol) were added to the obtained isoleucine ethyl ester hydrochloride salt solution in dry ice-acetone bath, allowing to react for 48 hours at a room temperature.

The reaction solution was filtered to remove a generated triethylamine hydrochloride salt.

The remaining solution was concentrated under decompression until the solvent was mostly removed. The obtained concentrate solution was dissolved in tetrahydrofuran (10 ml) and an excess of hexane was added thereto to induce the formation of precipitation. After the process was repeated at 2 or 3 times, the obtained precipitate was dissolved again in a small amount of methylalcohol. The resulting solution was dialyzed with methylalcohol at room temperature for 5 days and with distilled water for 5 days. The obtained product was dried at a low temperature, to produce final product, [NP(IleOEt)$_{1.10}$(GlyLacOEt)$_{0.02}$(AMPEG550)$_{0.88}$]$_n$ 8.90 g (yield 74%).

Hydrogen Nuclear Magnetic Resonance Spectrum (CDCl$_3$, ppm):

$\delta$=0.8 to 1.2 (b, —NHCH(CH(CH$_3$)CH$_2$CH$_3$)OCH$_2$C$\underline{H}_3$), $\delta$=1.3 to 1.5 (b, —NHCH(CH(CH$_3$)C$\underline{H}_2$CH$_3$)OCH$_2$CH$_3$, NHCH$_2$COOCH(CH$_3$)COOCH$_2$C$\underline{H}_3$), $\delta$=1.6 to 1.7 (b, —NHCH(C$\underline{H}$(CH$_3$)CH$_2$CH$_3$)OCH$_2$CH$_3$, —NHCH$_2$COOCH(C$\underline{H}_3$)COOCH$_2$CH$_3$), $\delta$=2.9 to 3.2 (b, —NHC$\underline{H}_2$(CH$_2$)$_3$(NH$_2$)CHCOOCH$_2$CH$_3$), $\delta$=3.4 (s, —NH(CH$_2$CH$_2$O)$_{11}$C$\underline{H}_3$), $\delta$=3.5 to 3.9 (b, —NH(C$\underline{H}_2$C$\underline{H}_2$O)$_{11}$CH$_3$), $\delta$=4.0 to 4.4 (b, —NHC$\underline{H}_2$COOCH(CH$_3$)COOC$\underline{H}_2$CH$_3$), $\delta$=5.2 to 5.4 (b, —NHCH$_2$COOC$\underline{H}$(CH$_3$)COOCH$_2$CH$_3$), Phosphorus Nuclear Magnetic Resonance Spectrum (CDCl$_3$, ppm): $\delta$ 17.9

Molecular weight (Mw): 392000

2-2) Preparation of CoFe$_2$O$_4$ Superparamagnetic Nanoparticle (Thermal Decomposition Method)

This step was carried out according to the same method of step 1-2) of Example 1 to prepare CoFe$_2$O$_4$ superparamagnetic nanoparticle.

2-3) Modification of Hydrophobic CoFe$_2$O$_4$ Superparamagnetic Nanoparticle to Hydrophilic Surface The surface modification of nanoparticle was carried out by surface ligand-exchange method (Langmuir, 15, 8633(1999)), the aminomethoxypolyethyleneglycol 550 having a weight-average molecular weight of 300 to 2,000 was used as a surface modifying agent for exchanging the hydrophobic surfactant.

(a) Solution 1: CoFe$_2$O$_4$ superparamagnetic nanoparticle (300 μmol, 0.0704 g) was dispersed in 20 mL of hexane.

(b) Solution 2: aminomethoxy polyethylene glycol 550 (300 μmol, 0.1647 g) was dissolved in 30 mL solvent (pH 4.0) including a mixture of distilled water and ethyl alcohol at a ratio of 2:1.

(c) Solution 1 was added to Solution 2 where lower layer was transparent and upper layer was in black.

(d) The solution was sufficiently agitated with a sonicator until the color of upper layer was changed from black to transparent, and the color of lower layer was changed from transparent into black. While agitating with sonicator, the solution was cooled with ice to prevent the increase of temperature.

(e) After agitation, the solution was left in a refrigerator for 24 hr to induce the layer separation.

(f) After the layer separation, only lower layer was separated and centrifuged at 3,000 rpm for 20 minutes.

(g) After centrifuging, only solution except for the precipitate and supernant was separated.

(h) The centrifugation was carried out at 13,000 rpm for 10 minutes again.

(i) After centrifuging, the supernant and solution were removed to collect the precipitate.

(j) The collected precipitate was dissolved in distilled water homogeneously, and then centrifuged at 3,000 rpm for 20 minutes.

(k) After centrifuging, only precipitate was collected and dissolved in distilled water homogeneously.

(l) The precipitate was purified by repeating the steps of (h) to (k) at several times.

(m) The final precipitate was collected, dissolved in distilled water and kept in a refrigerator.

Figure 9:
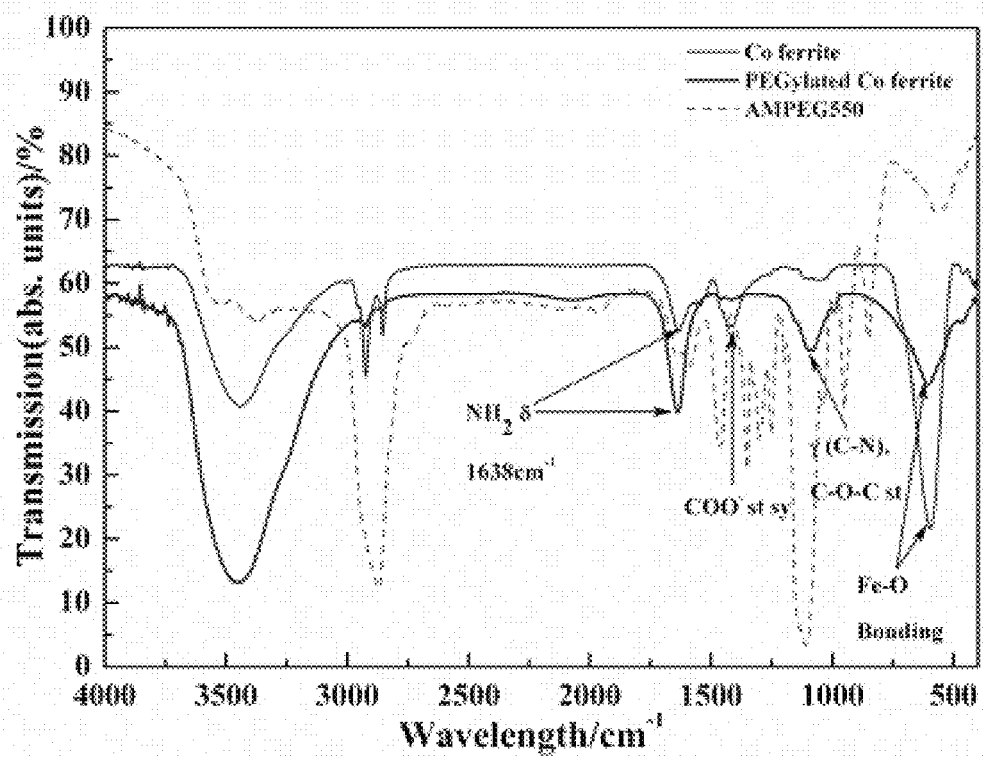
FIG. 9 is a graph of Fourier transform infrared spectroscopy (FTIR) showing the coordination bond of $CoFe_2O_4$ treated with aminomethoxy polyethyelene glycol 550, among the ferrite nanoparticle ($Fe_3O_4$, $MnFe_2O_4$, $CoFe_2O_4$, and/or $NiFe_2O_4$) which has a hydrophilic surface and constitutes the temperature-sensitive phosphazene-based 'mixed-type' magnetic polymers according to an embodiment of the present invention.
Figure 10:
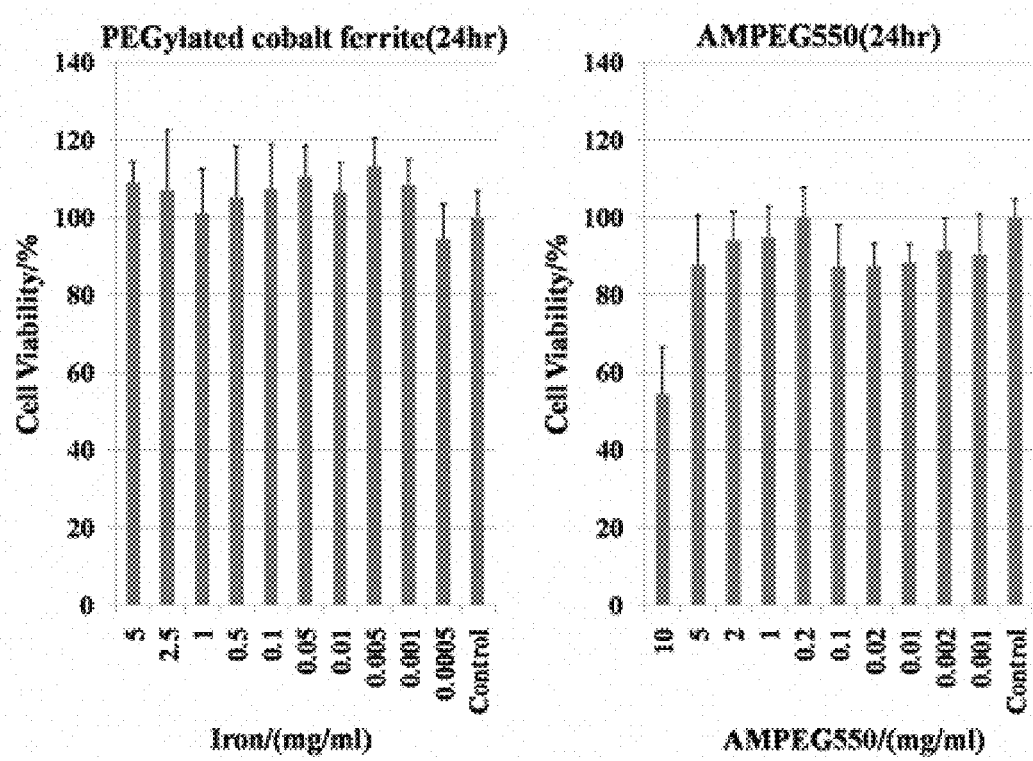
FIG. 10 is a graph of MTT assay confirming in vitro cell toxicity of PEGylated $CoFe_2O_4$ among the ferrite nanoparticle ($Fe_3O_4$, $MnFe_2O_4$, $CoFe_2O_4$, and/or $NiFe_2O_4$) which have hydrophilic surface and constitutes the temperature-sensitive phosphazene-based 'mixed-type' magnetic polymer according to an embodiment of the present invention.
Figure 11:
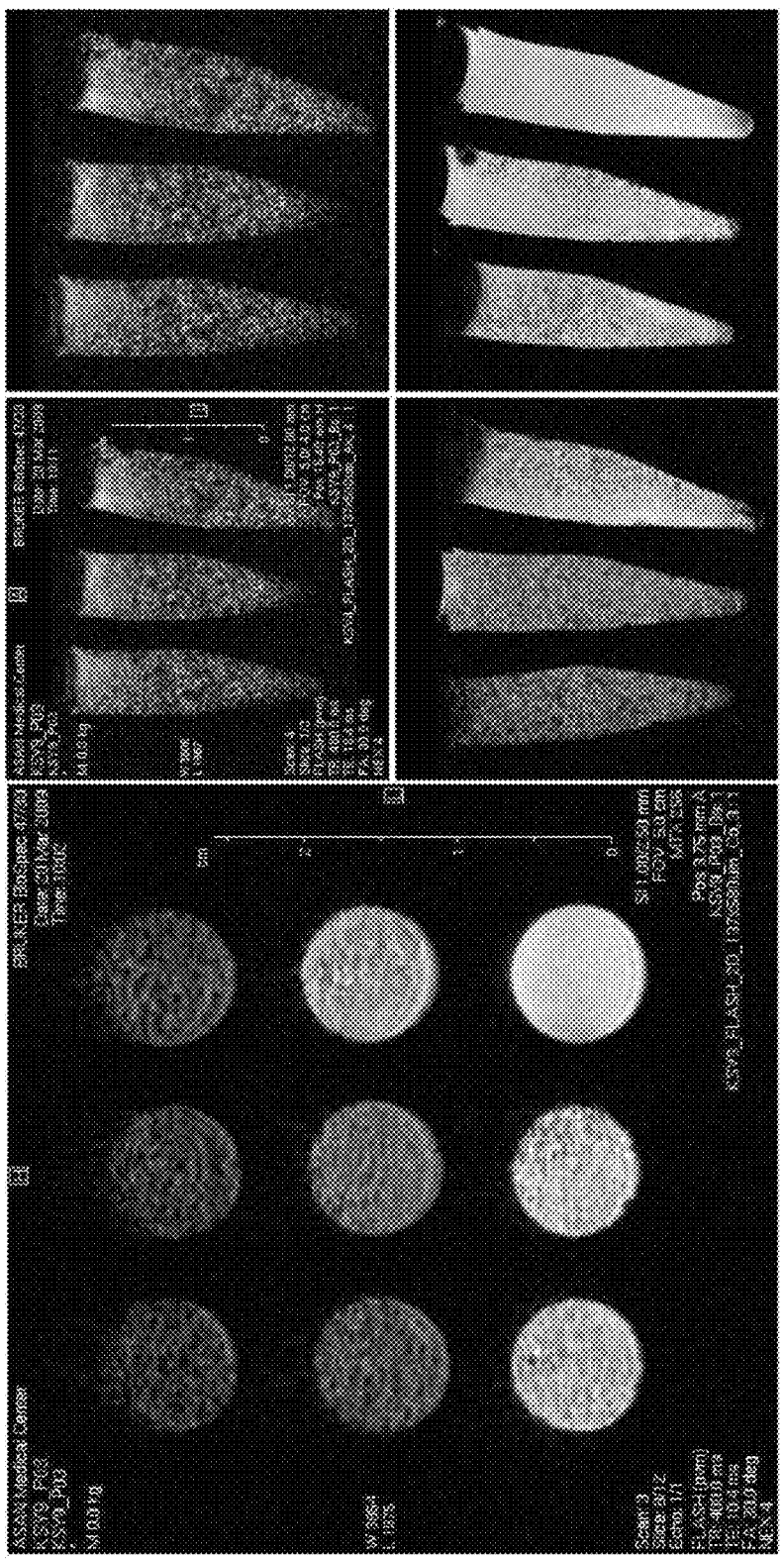
FIG. 11 is a photograph showing phantom study using MRI of phosphazene-based 'mixed-type' magnetic polymers mixed with $CoFe_2O_4$ physically, among the temperature-sensitive phosphazene-based 'mixed-type' magnetic polymers according to an embodiment of the present invention.
Figure 12:
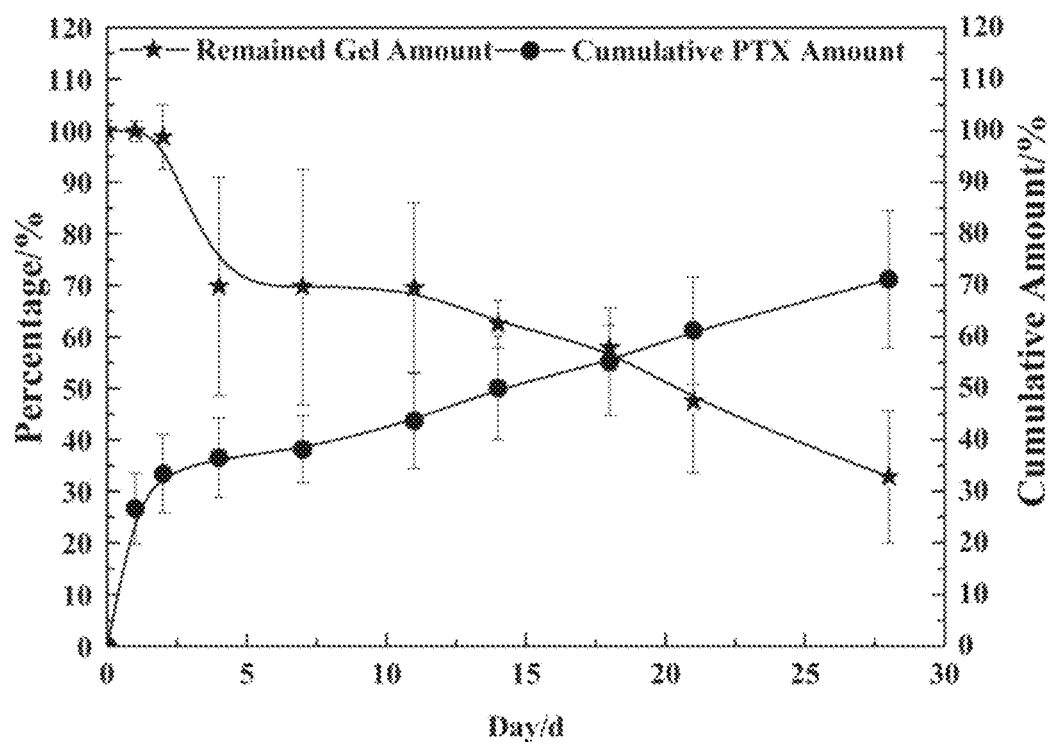
FIG. 12 is a graph showing the weight reduction tendency in vitro depending on the time of phosphazene-based 'mixed-type' magnetic polymers mixed with $CoFe_2O_4$ physically, among the temperature-sensitive phosphazene-based 'mixed-type' magnetic polymers according to an embodiment of the present invention (left-hand axis), and the drug release tendency in vitro of paclitaxel mixed with the 'mixed-type' magnetic polymers (right-hand axis).
Figure 13:
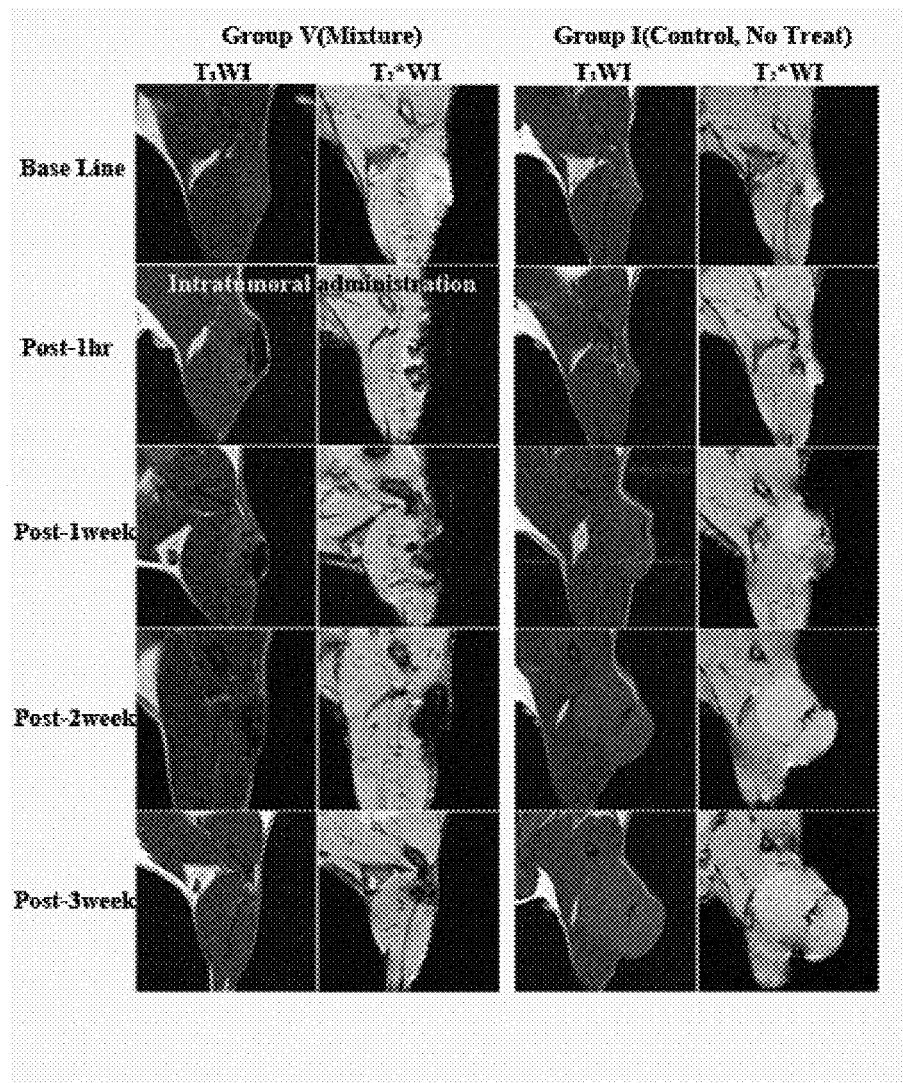
FIG. 13 is a MR images showing the long-term monitoring for the tumor and the drug release tendency in vivo of the magnetic polymer and using paclitaxel mixed physically with the 'mixed-type' magnetic polymer, among the ferrite nanoparticle ($Fe_3O_4$, $MnFe_2O_4$, $CoFe_2O_4$, and/or $NiFe_2O_4$) which has a hydrophilic surface and constitutes the temperature-sensitive phosphazene-based 'mixed-type' magnetic polymers according to an embodiment of the present invention.
Figure 14:
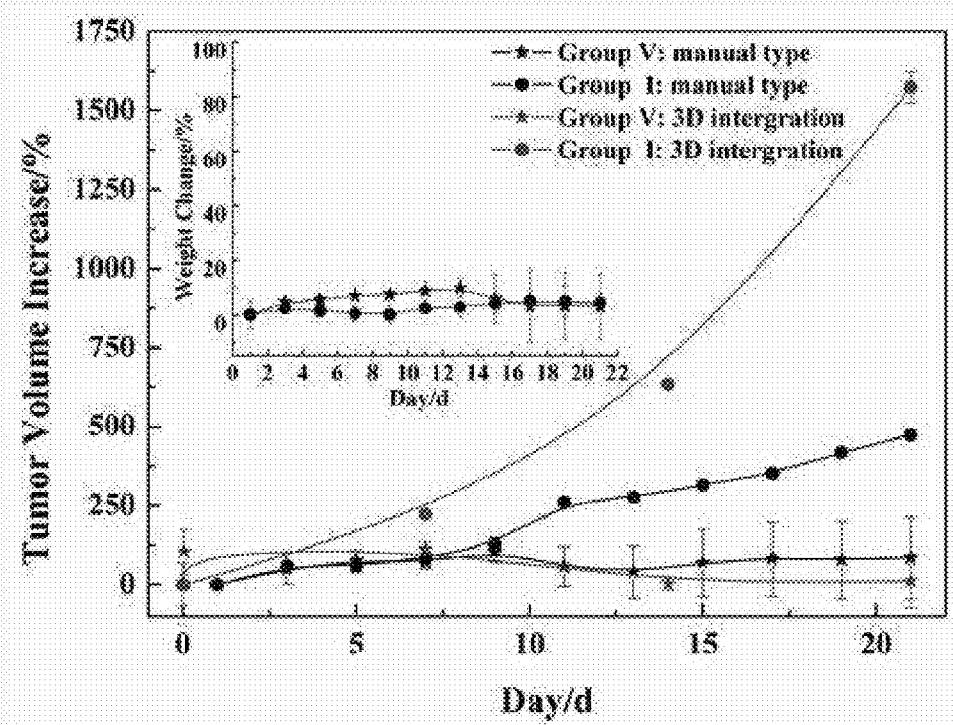
FIG. 14 is a graph showing the long-term monitoring for the tumor of the magnetic polymer and using paclitaxel mixed physically with the 'mixed-type' magnetic polymer, among the ferrite nanoparticle ($Fe_3O_4$, $MnFe_2O_4$, $CoFe_2O_4$, and/or $NiFe_2O_4$) which has a hydrophilic surface and constitutes the temperature-sensitive phosphazene-based 'mixed-type' magnetic polymers according to an embodiment of the present invention.
Figure 15:
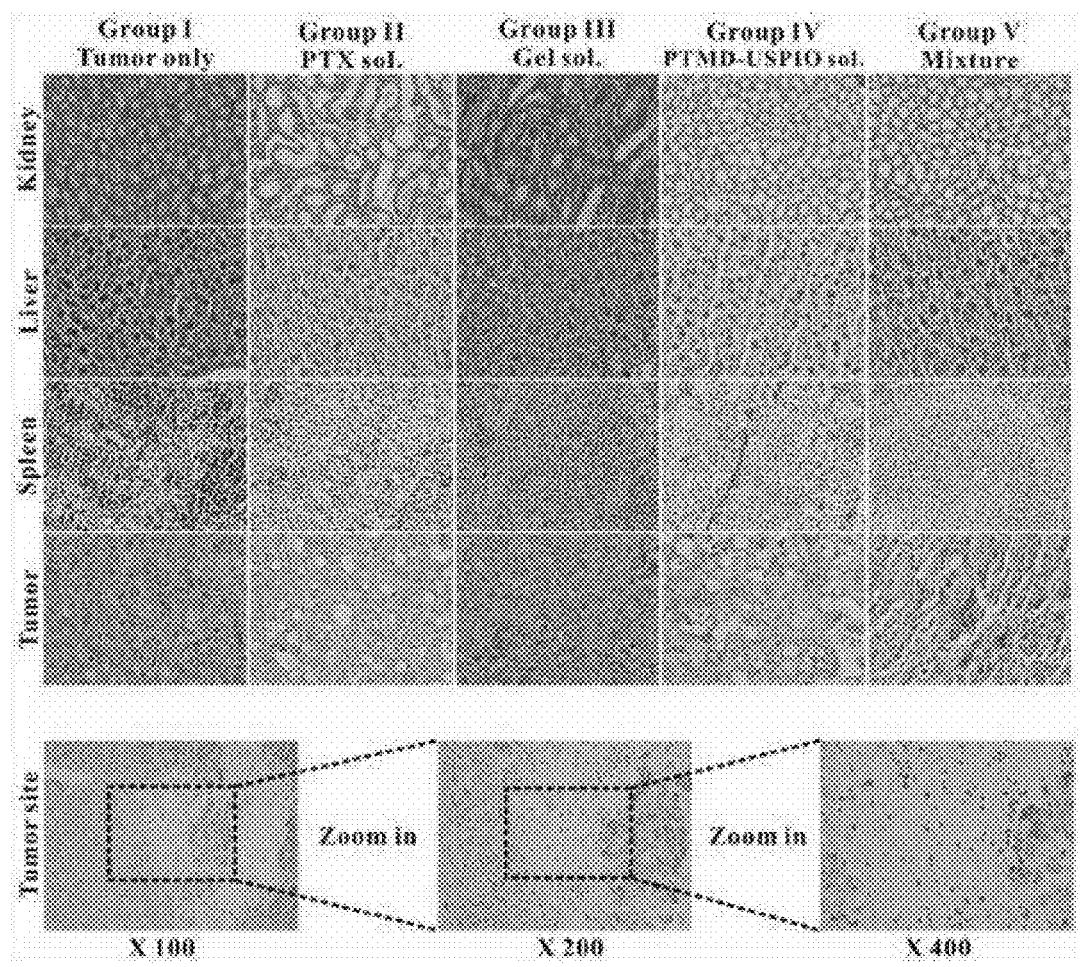
FIG. 15 is a photograph showing cell toxicity and left iron using Hematoxylin & Eosin staining method and Prussian Blue staining (bottom of photograph), after confirming the long-term monitoring for the tumor and the drug release tendency in vivo of the magnetic polymer and using paclitaxel mixed physically with the 'mixed-type' magnetic polymer, among the ferrite nanoparticle ($Fe_3O_4$, $MnFe_2O_4$, $CoFe_2O_4$, and/or $NiFe_2O_4$) which has a hydrophilic surface and constitutes the temperature-sensitive phosphazene-based 'mixed-type' magnetic polymers according to an embodiment of the present invention.

(n) Whether the amine group of AMPEG550 was on the surface of nanoparticle via coordination bond was checked by FTIR (see FIG. 9).

<FTIR>

Vicinity of 1638 cm$^{-1}$: absorption band for amine group (primary NH$_2$) of aminomethoxy polyethylene glycol 550

Vicinity of 1100 cm$^{-1}$: stretching absorption band of aminomethoxy polyethylene glycol 550

2-4) Preparation of Phosphazene-Based 'Mixed-Type' Magnetic Polymer, Magnetic-[NP(IleOEt)$_{1.10}$(GlyLacOEt)$_{0.02}$(AMPEG550)$_{0.88}$]$_n$.

Figure 4:
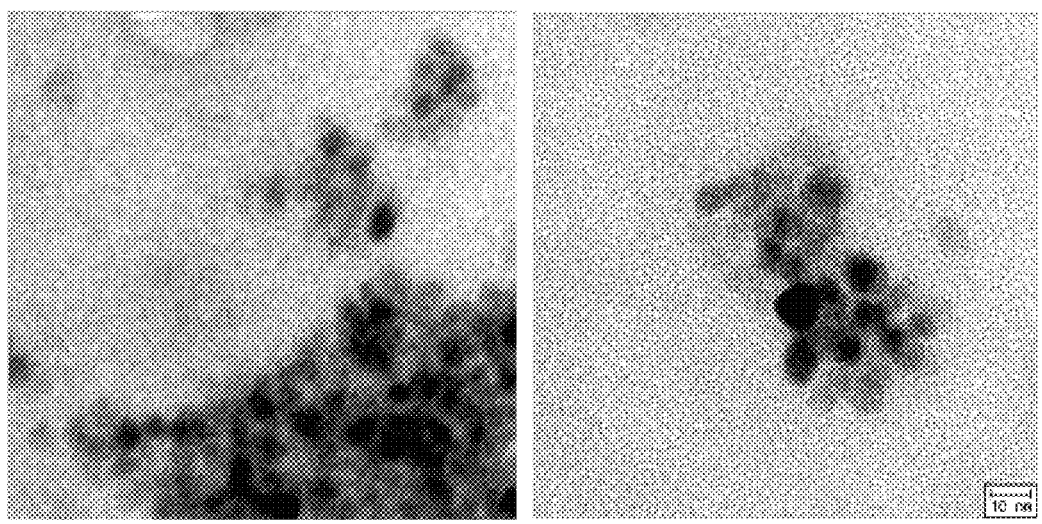
FIG. 4 is a photograph of transmission electron microscopy of phosphazene-based 'bound-type' magnetic polymer bound with $CoFe_2O_4$ via hydrophogic interaction among the temperature-sensitive phosphazene-based 'bound-type' magnetic polymer according to an embodiment of the present invention (left-hand side: 30 nm scale, and right-hand side: 10 nm scale).
Figure 5:
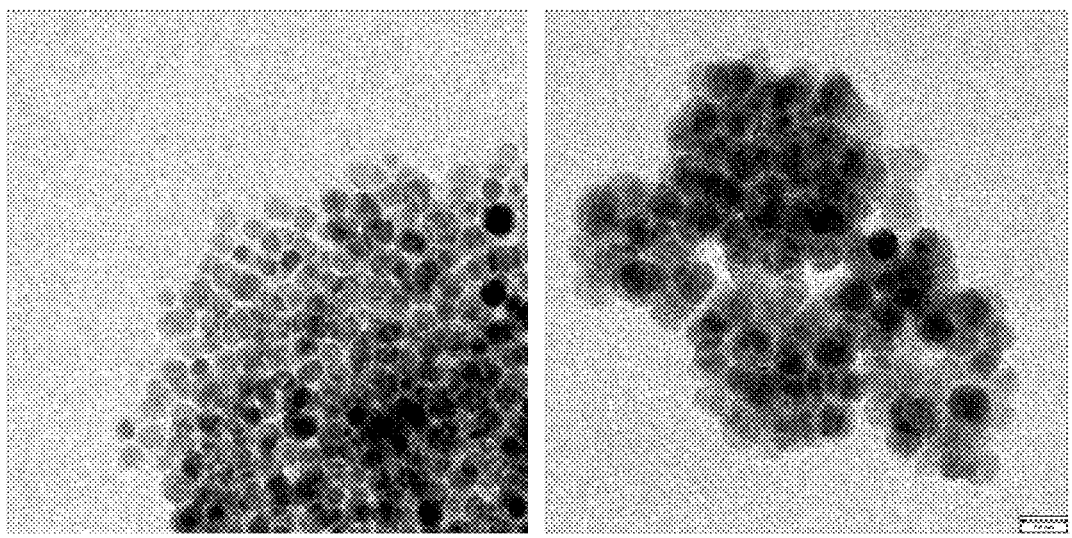
FIG. 5 is a photograph of transmission electron microscopy showing the particle size and shape of $CoFe_2O_4$ treated with aminomethoxy polyethyelene glycol 550, among the ferrite nanoparticle ($Fe_3O_4$, $MnFe_2O_4$, $CoFe_2O_4$, and/or $NiFe_2O_4$) which has a hydrophilic surface and constitutes the temperature-sensitive phosphazene-based 'mixed-type' magnetic polymers according to an embodiment of the present invention (left side: 30 nm scale, and right side: 10 nm scale).
Figure 6:
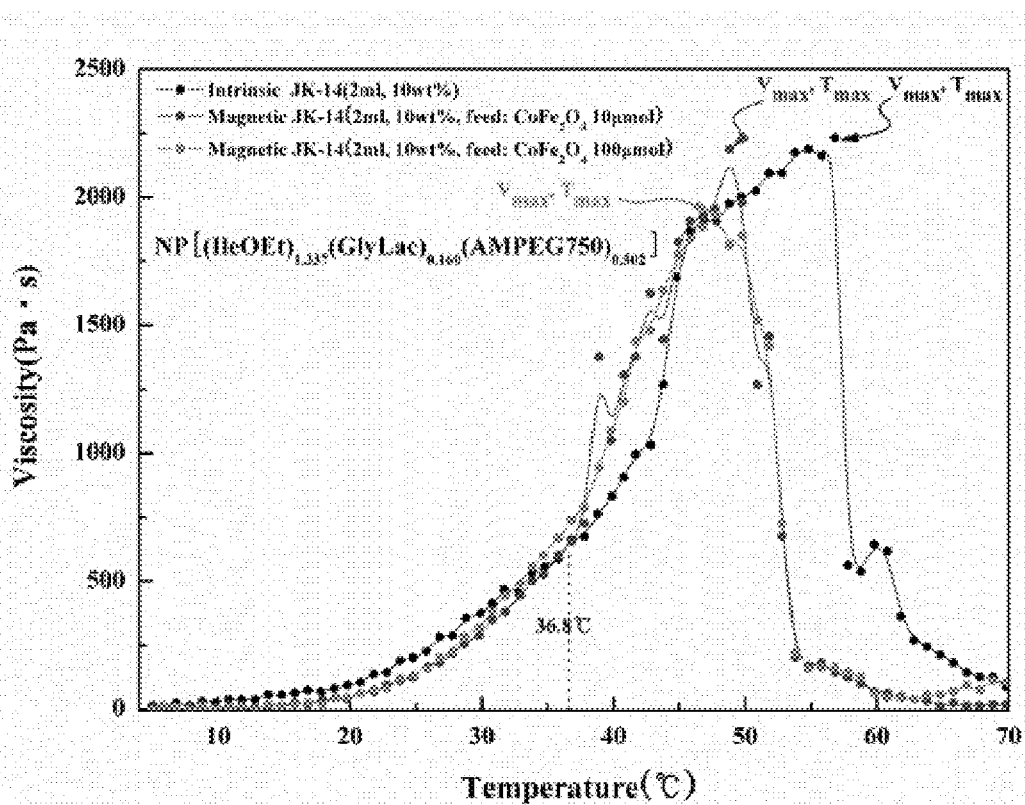
FIG. 6 is a graph showing the viscosity property of phosphazene-based 'bound-type' magnetic polymers bound with $CoFe_2O_4$ via hydrophobic bond, among the temperature-sensitive phosphazene-based 'bound-type' magnetic polymers according to an embodiment of the present invention.
Figure 7:
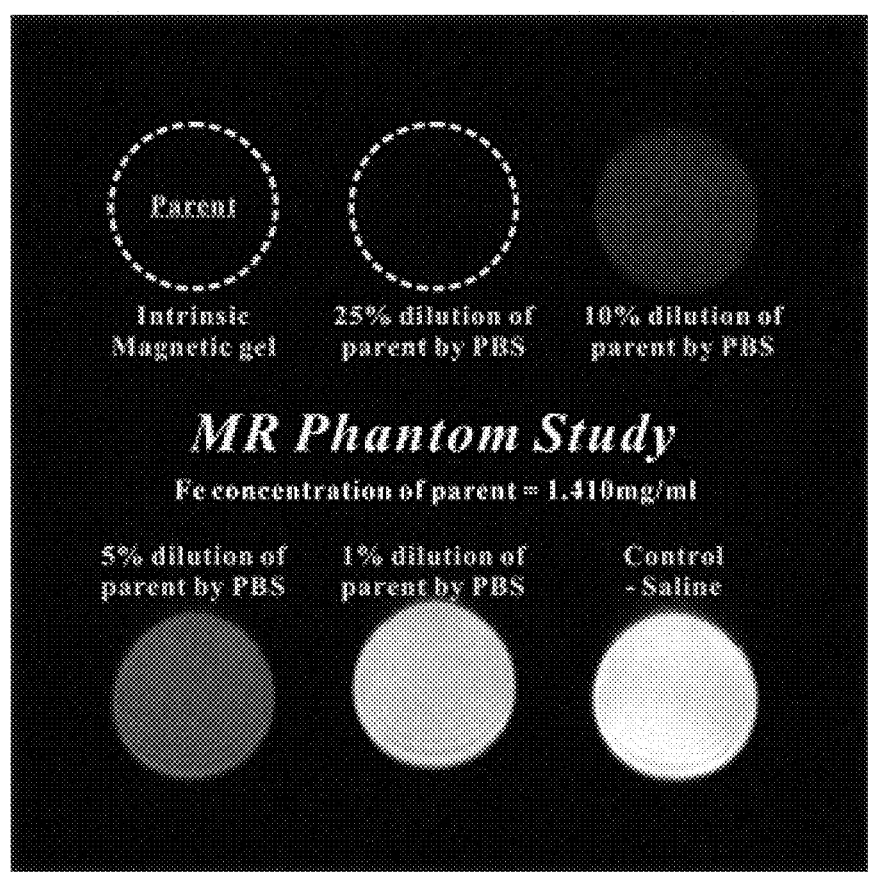
FIG. 7 is a graph showing phantom study using MRI depending on the concentration of phosphazene-based 'bound-type' magnetic polymers bound with $CoFe_2O_4$ via hydrophobic interaction, among the temperature-sensitive phosphazene-based 'bound-type' magnetic polymers according to an embodiment of the present invention.
Figure 8:
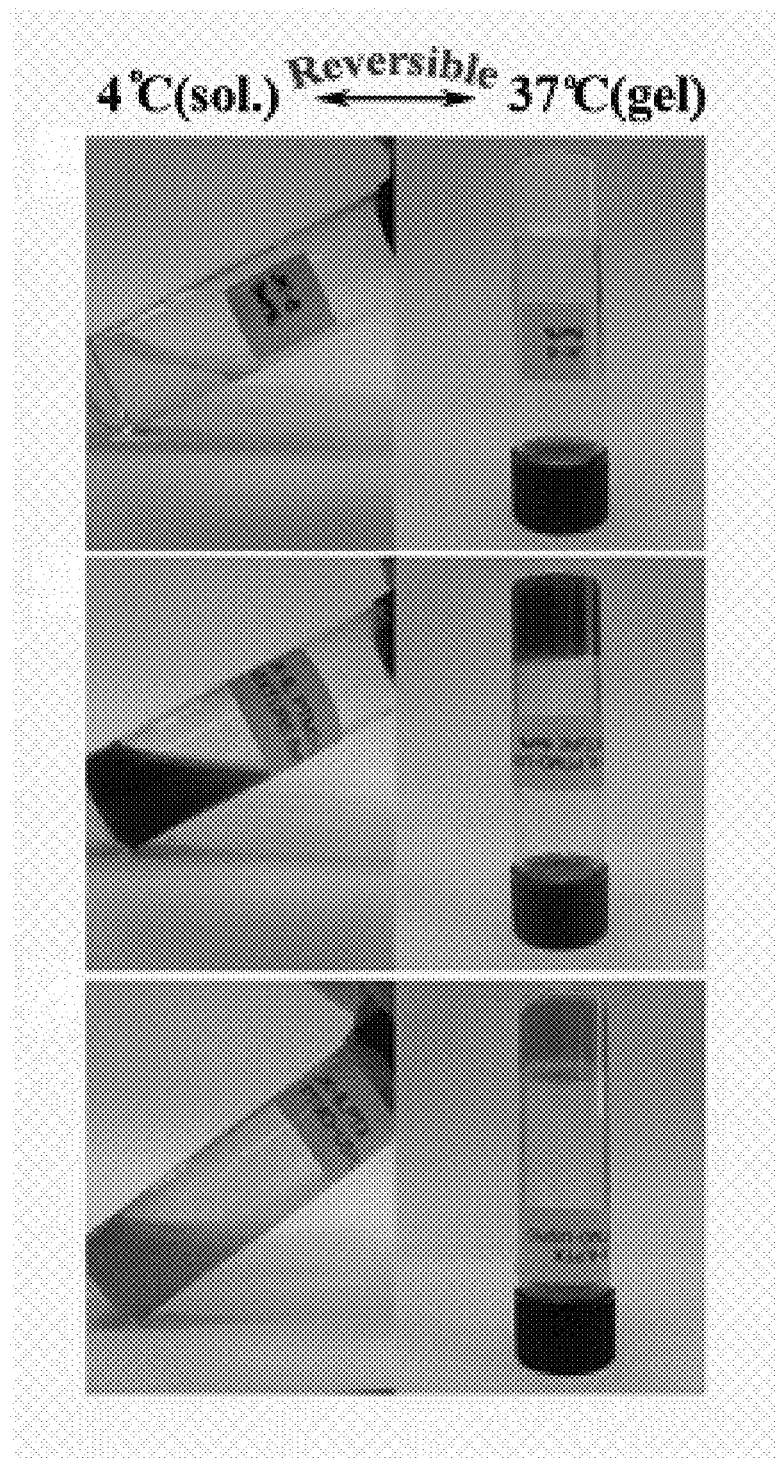
FIG. 8 is a photograph showing a sol-to-gel property of phosphazene-based 'mixed-type' magnetic polymers mixed with $CoFe_2O_4$ physically, among the temperature-sensitive phosphazene-based 'mixed-type' magnetic polymers according to an embodiment of the present invention (upper part for gel solution of phosphazene-based polymer, middle part for gel solution of 'mixed-type' magnetic polymers, bottom part for gel solution of 'mixed-type' magnetic polymers mixed with paclitaxel)

As described above, the phosphazene-based 'mixed-type' magnetic polymer was obtained by physically adding a suitable amount of the phosphazene-based polymer and mixing an aqueous solution of the superparamagnetic nanoparticle modified with hydrophilic surface. For example, to make about 4 mL solution (10 wt %) of the phosphazene-based 'mixed-type' magnetic polymer, Magnetic-[NP(IleOEt)$_{1.10}$(GlyLacOEt)$_{0.02}$(AMPEG550)$_{0.88}$]$_n$, about 0.4 g of [NP(IleOEt)$_{1.10}$(GlyLacOEt)$_{0.02}$(AMPEG550)$_{0.88}$]$_n$ was added to 3.6 g solution of the superparamagnetic nanoparticle modified with hydrophilic surface dissolved in a distilled water, and mixed with a magnetic rod at 4° C. for 24 hr to produce 4 mL solution (10 wt %) of the phosphazene-based 'mixed-type' magnetic polymer. The produced solution was performed by freeze-drying to obtain about 0.4 g of phosphazene-based 'mixed-type' magnetic polymer. 0.4 g of phosphazene-based 'mixed-type' magnetic polymer was dissolved in 3.6 g of distilled water, and dispersed for 24 hr to obtain 10 wt % aqueous solution of phosphazene-based 'mixed-type' magnetic polymer (see FIGS. 4 and 5).

As described above, in the preparation of 'mixed-type' magnetic polymer of Magnetic-[biodegradable and thermosensitive poly(organophosphazene)], the method of step 2-2) in Example 2 is the same as that of step 1-2) in Example 1, step 2-4) can be applied for all biodegradable and thermosensitive poly(organophosphazene) of items ①~⑥. These examples should not be interpreted as limiting the scope of the present invention in any manner.

What is claimed is:

1. A poly(organophosphazene)-superparamagnetic nanoparticle complex comprising a biodegradable and thermosensitive phosphazene-based polymer showing a sol-to-gel behavior depending upon the temperature change; and a superparamagnetic ferrite nanoparticle represented by Chemical formula 2a, or Chemical formula 2b:

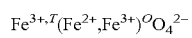

Chemical formula 2a

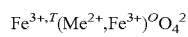

Chemical formula 2b

Wherein, Me is a transitional metal selected from the group consisting of Sc, Ti, V, Cr, Mn, Co, Ni, Cu and Zn, T is tetrahedral site, and O is octahedral site.

2. The poly(organophosphazene)-superparamagnetic nanoparticle complex according to claim 1, the phosphazene-based polymer is represented by Chemical formula 1a:

Chemical formula 1a

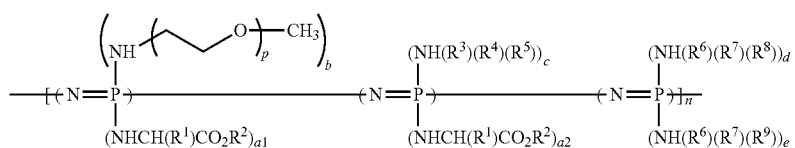

Wherein, p is a number of repeating unit of ethylene glycol ranging from 7 to 50, $NHCH(R^1)CO_2R^2$ is an ester of hydrophobic amino acid, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$, $NH(R^3)(R^4)(R^5)$ is an ester of amino acid, peptide or depsipeptide, $R^3$ is CH(W), $R^4$ is selected from the group consisting of $CO_2$, $CONHCH(X)CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_5NHC(=NH)NH_2$, $CH_2C_3N_2H_3$, and $CH_2SH$, $NH(R^6)(R^7)(R^8)$ and $NH(R^6)(R^7)(R^9)$ are substitutents with a functional group, $R^6$ is CH(Y), $R^7$ is selected from the group consisting of CH, $C_2H_4$, $C_3H_6$, $C_4H_8$, $CH_2C_6H_4$, $CH_2CO_2$, O, CO, $CO_2$, S, N, CON, CONHCH(Z)O, CONHCH(Z)S, CONHCH(Z)N, COCHNH(Z)CON, CONHCH(Z)CO, CONHCH(Z)CO$_2$, CONHCH(Z)CONHCH(M)O, CONHCH(Z)CONHCH(L)CONHCH(L)O, CONHCH(Z)CONHCH(M)S, CONHCH(Z)CONHCH(M)CONHCH(L)S, CONHCH(Z)CONHCH(M)N, CONHCH(Z)CONHCH(M)CONHCH(L)N, COCHNH(Z)CONHCH(M)CON, COCHNH(Z)CONHCH(M)CONHCH(L)CON, COCHNH(Z)CONHCH(M)CO, COCHNH(Z)CONHCH(M)CONHCH(L)CO, COCHNH(Z)CONHCH(M)CO$_2$, and COCHNH(Z)CONHCH(M)CONHCH(L)CO$_2$, $R^8$ is selected from the group consisting of OH, SH, H, $CH_3$, $C_2H_5$, $C_3H_7$, $C_4H_9$, $CH_2C_6H_5$, $CH_2CHCH_2$, and a protecting group listed in Table 1 to Table 5, where Y, Z, L, and M are independently is selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, CH2OH, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)qSH$, $NH(CH_2CH_2NH)rH$, $[NHCH(C_4H_8NH_2)CO]rOH$, $[NHCH[(CH_2)_3C(=NH)(NH_2)]CO]_rOH$, folic acid, hyaluronic acid, polyhistidine, cyclodextrin, heparin, chitosan, and protamine, where q is a number of repeating unit of methylene ranging from 1 to 20, r is a number of repeating unit of ethyleneimine, lysine and arginine which ranges 1 to 18,000, $a_1$, $a_2$, b, c, d and e are the content of each substituent where each $a_1$, $a_2$, $b_1$ and d is 0.01 to 1.9, each c and e is 0 to 1.9, and $a_1+a_2+b+c+d+e=2.0$, n is a polymerization degree of phosphazen polymer ranging from 5 to 100,000.

3. The poly(organophosphazene)-superparamagnetic nanoparticle complex according to claim 2, wherein the complex is
1) a mixed-type where the superparamagnetic ferrite nanoparticle with a hydrophilic surface is physically mixed with the phosphazene-based polymer, or
2) a bound-type where a hydrophobic surfactant on the surface of the superparamagnetic ferrite nanoparticle binds chemically via hydrophobic binding to the ester of hydrophobic amino acid $(NHCH(R^1)CO_2R^2)$ of the phosphazene-based polymer.

4. The poly(organophosphazene)-superparamagnetic nanoparticle complex according to claim 1, wherein the phosphazene-based polymer is represented by Chemical formula 1 b:

Chemical formula 1b

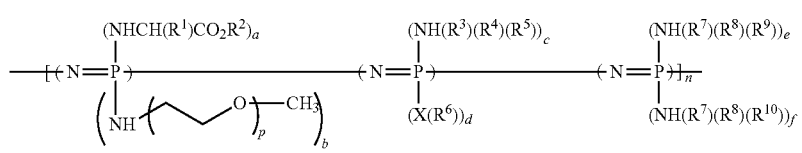

Wherein, p is a numerical value ranging from 7 to 50, in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$ and $CH_2CHCH_2$, in the formula $NH(R^3)(R^4)(R^6)$, $R^3$ is CH(W), $R^4$ is selected from the group consisting of $CO_2$, $CONHCH(X)CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, in the formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substitutent with a functional group where $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z)CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)CO]_q$, $[OCOC_6H_5O(CH_2)_3OC_6H_5CO]_q$ and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_qH$, $[NHCH(C_4H_8NH_2)CO]_qOH$, $[NHCH[(CH_2)_3C(=NH)(NH_2)]CO]_qOH$, folic acid, hyaluronic acid, polyhistidine, cyclodextrin, heparin, chitosan, protamine and a protecting group of general functional group, Where, Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, and q is a number of repeating unit ranging from 1 to 18,000, in the formula, $NH(R^7)(R^6)(R^{10})$, $R^7$ and $R^8$ are the same substitutents as defined in the $NH(R^7)(R^8)(R^9)$, $R^{10}$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substitutent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000.

5. The poly(organophosphazene)-superparamagnetic nanoparticle complex according to claim 4, wherein, in the definition of $R^6$ and $R^{10}$, the acrylate-based compound is an acrylate; an acrylate including a C1 to C30 substituted or unsubstituted linear or branched alkyl substituted with at least one selected from the group consisting of a halogen, a C1 to C12 alkoxy, an acryloyloxy, and an amino acid; an acrylate including an amino acid group; ethylene glycol acrylate; or a polyethyleneglycol acrylate including polyethyleneglycol of a molecular weight of 200 to 2,500, the metacrylate-based compound is metacrylate; metacrylate including a C1 to C30 substituted or unsubstituted linear or branched alkyl substituted with at least one selected from the group consisting of a halogen, a C1 to C12 alkoxy, an acryloyloxy, and an amino acid; metacrylate including an amino acid group; or polyethyleneglycol metacrylate including polyethyleneglycol of a molecular weight of 200 to 2,500, the acrylamide-based compound is acryl amide; acryl amide including a C1 to C30 substituted or unsubstituted linear or branched alkyl substituted with at least one selected from the group consisting of a halogen, a C1 to C12 alkoxy, acryloyloxy, and an amino acid; acryl amide including an amino acid group; ethyleneglycol acrylamide; or polyethyleneglycol amide including polyethyleneglycol of a molecular weight of 200 to 2,500, the vinyl sulfone-based compound is vinyl sulfone, vinyl sulfone-ethyleneglycol, vinyl sulfone-polyethyleneglycol including polyethyleneglycol of a molecular weight of 200 to 2,500, vinyl sulfone-alkylate including a C1 to C30 alkyl, vinyl sulfone-amino acid, or vinyl sulfone-a peptide, the thiol-based compound is thiol-polyethylene glycol including polyethylene glycol of a molecular weight of 200 to 2,500, or thiol-alkylate including a C1 to C30 alkyl, the cysteine-based compound is cysteine, N-acetyl-cysteine, or N-acetyl-cysteine alkyl ester including a C1 to C30 alkyl, the cisteamine-based compound is cisteamine, or N-acetyl-cisteamine, the mercaptic acid-based compound is 2-mercapto succinic acid, the allyl pyrimidine-based compound is 1-allyl-2-aminopyridinium, or 1-allyl-6-amino-3-ethyl-5-nitrosouracil, the tyramine-based compound is tyramine, or 3-methoxytyramine, the tyrosine-based compound is tyrosine, or tyrosine methylester, or tyrosine ethylester, and the phenol-based compound is selected from the group consisting of 2-amino-4-phenylphenol, 2-amino-4-teriaryamylphenol, 2-amino-4-tert-butylphenol phenol, 8-amino-2-naphthol, 5-amino-1-naphthol, 4-amino-1-naphthol, 3-amino-2-naphthol, 1-amino-2-naphthol, 4-amino 2,5 dimethylphenol, 5-amino-2-methoxyphenol, 5-amino-2-methylphenol, 4-amino-3-methylphenol, 4-amino-2-methylphenol, 2-amino-5-methylphenol, 2-amino-4-methylphenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitrophenol, 2-amino-5-nitrophenol, 2-amino-4-nitrophenol, 2-amino-4 fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6nitrophenol, and 4-amino-2,6-dibromophenol.

6. The poly(organophosphazene)-superparamagnetic nanoparticle complex according to claim 4, wherein the complex is 1) a mixed-type where the superparamagnetic ferrite nanoparticle with a hydrophilic surface is physically mixed with the phosphazene-based polymer, or
2) a bound-type where a hydrophobic surfactant on the surface of the superparamagnetic ferrite nanoparticle binds chemically via hydrophobic binding to the ester of hydrophobic amino acid $(NHCH(R^1)CO_2R^2)$ of the phosphazene-based polymer.

7. The poly(organophosphazene)-superparamagnetic nanoparticle complex according to claim 1, wherein the phosphazene-based polymer is represented by Chemical formula 1c, capable of crosslinking chemically, and covalently bound to a physiologically-active material:

[Chemical formula 1c]

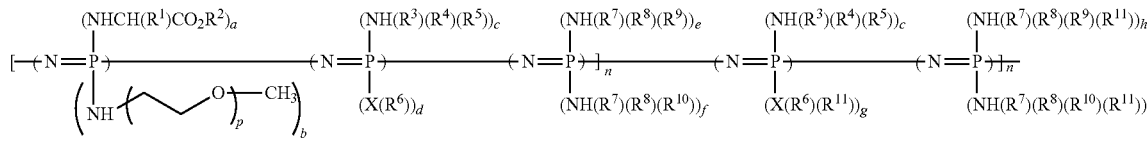

wherein,
p is a numerical value ranging of 7 to 50,
in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$,
in the formula $NH(R^3)(R^4)(R^5)$, $R^3$ is CH(W), $R^4$ is selected from the group consisting of $CO_2$, CONHCH $(X)CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC$ $(=NH)NH_2$, $CH_2C_3N_2H_3$, and $CH_2SH$,
in the formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound,
$NH(R^7)(R^8)(R^9)$ is a substitutent including a functional group, where, $R^7$ is CH(Y), $R^8$ is selected from the group consisting of $CH_2$, $C_2H_4$, $C_3H_6$, $C_4H_e$, $CH_2C_6H_4$, $CH_2CO_2$, $C_2H_4CO_2$, O, CONHCH(Z)O, CONHCH(Z) CONHCH(M)O, CONHCH(Z)CONHCH(N)CON-HCH(L)O, CO, $CO_2$, S, CONHCH(Z)S, CONHCH(Z) CONHCH(M)S, CONHCH(Z)CONHCH(M) CONHCH(L)S, N, CONHCH(Z)N, CONHCH(Z) CONHCH(M)N, CONHCH(Z)CONHCH(M) CONHCH(L)N, CON, CONHCH(Z)CON, CONHCH (Z)CONHCH(M)CON, CONHCH(Z)CONHCH(M) CONHCH(L)CON, CONHCH(Z)CO, COCHNH(Z) CONHCH(M)CO, COCHNH(Z)CONHCH(M) CONHCH(L)CO, CONHCH(Z)$CO_2$, COCHNH(Z) CONHCH(M)$CO_2$, COCHNH(Z)CONHCH(M) CONHCH(L)$CO_2$, $[OCH(CH_3)CO]_q$, $(OCH_2CO)_q$, $[(OCH(CH_3)CO]_q$, $[OCO(CH_2)_8CO]_q$, $[OCOC_6H_5O (CH_2)_3OC_6H_5CO]_q$, and $[OCOC_6H_5O(CH_2)_8 OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_q SH$, $NH(CH_2CH_2NH)_qH$, $[NHCH(C_4H_8NH_2)CO]_q OH$, $[NHCH[(CH_2)_3C(=NH)(NH_2)]CO]_qOH$, folic acid, hyaluronic acid, polyhistidine, cyclodextrin, heparin, chitosan, protamine, and a general protecting group of a functional group, where Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4HNH_2$, $C_3H_6NHC$ $(=NH)NH_2$, $CH_2C_3N_2H_3$, and $CH_2SH$, and q represents a number of a repeating unit and ranges from 1 to 18000, $R^{10}$ is a compound including thiol, vinyl, tyramine, tyrosine, or phenol-based compound, and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $R^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, a, b, c, d, e, f, g, h and i are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

8. The poly(organophosphazene)-superparamagnetic nanoparticle complex according to claim 7, wherein in the definition of $R^6$ and $R^{10}$,
the acrylate-based compound is an acrylate; an acrylate including a C1 to C30 substituted or unsubstituted linear or branched alkyl substituted with at least one selected from the group consisting of a halogen, a C1 to C12 alkoxy, an acryloyloxy, and an amino acid; an acrylate including an amino acid group; ethylene glycol acrylate; or a polyethyleneglycol acrylate including polyethyleneglycol of a molecular weight of 200 to 2,500, the metacrylate-based compound is metacrylate; metacrylate including a C1 to C30 substituted or unsubstituted linear or branched alkyl substituted with at least one selected from the group consisting of a halogen, a C1 to C12 alkoxy, an acryloyloxy, and an amino acid; metacrylate including an amino acid group; or polyethyleneglycol metacrylate including polyethyleneglycol of a molecular weight of 200 to 2,500, the acrylamide-based compound is acryl amide; acryl amide including a C1 to C30 substituted or unsubstituted linear or branched alkyl substituted with at least one selected from the group consisting of a halogen, a C1 to C12 alkoxy, acryloyloxy, and an amino acid; acryl amide including an amino acid group; ethyleneglycol acrylamide; or polyethyleneglycol amide including polyethyleneglycol of a molecular weight of 200 to 2,500, the vinyl sulfone-based compound is vinyl sulfone, vinyl sulfone-ethyleneglycol, vinyl sulfone-polyethyleneglycol including polyethyleneglycol of a molecular weight of 200 to 2,500, vinyl sulfone-alkylate including a C1 to C30 alkyl, vinyl sulfone-amino acid, or vinyl sulfone-a peptide, the thiol-based compound is thiol-polyethylene glycol including polyethylene glycol of a molecular weight of 200 to 2,500, or thiol-alkylate including a C1 to C30 alkyl, the cysteine-based compound is cysteine, N-acetyl-cysteine, or N-acetyl-cysteine alkyl ester including a C1 to C30 alkyl, the cisteamine-based compound is cisteamine, or N-acetyl-cisteamine, the mercaptic acid-based compound is 2-mercapto succinic acid, the allyl pyrimidine-based compound is 1-allyl-2-aminopyridinium, or 1-allyl-6-amino-3-ethyl-5-nitrosouracil, the tyramine-based compound is tyramine, or 3-methoxytyramine, the tyrosine-based compound is tyrosine, or tyrosine methylester, or tyrosine ethylester, and the phenol-based compound is selected from the group consisting of 2-amino-4-phenylphenol, 2-amino-4-teriaryamylphenol, 2-amino-4-tert-butylphenol phenol, 8-amino-2-naphthol, 5-amino-1-naphthol, 4-amino-1-naphthol, 3-amino-2-naphthol, 1-amino-2-naphthol, 4-amino 2,5 dimethylphenol, 5-amino-2-methoxyphenol, 5-amino-2-methylphenol, 4-amino-3-methylphenol, 4-amino-2-methyl phenol, 2-amino-5-methylphenol, 2-amino-4-methylphenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitrophenol, 2-amino-5-nitrophenol, 2-amino-4-nitrophenol, 2-amino-4 fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6nitrophenol, and 4-amino-2,6-dibromophenol.

9. The poly(organophosphazene)-superparamagnetic nanoparticle complex according to claim 7, wherein the protein, the polypeptide, the peptide, the fusion protein and the antibody are selected from the group consisting of erythropoietin (EPO), Interferon-alpha, Interferon-beta, Interferon-gamma, growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, Insulin, albumin, Botulinum toxin, oxytocin, vasopressin, fibroblast growth factor (FGF), epidermal growth factor (EGF), platelet-derived growth factor (PDGF), keratinocyte growth factor, insulin-like growth factor (IGF), vascular endothelial growth factor (VEGF), transforming growth factor-beta, (TGF-β), nerve growth factor, brain-derived neurotrophic factor (BDNF), neurotrophin-3 (NT-3), neurotrophin-4/5, prolactin, luliberin, LHRH agonists, LHRH antagonists, glucagon, Interleukin-2 (IL-2), Interleukin-11 (IL-11), gastrin, tetragastrin, pentagastrin, urogastrone, secretin, enkephalins, endorphins, angiotensins, tumor necrosis factor (TNF), tumor necrosis factor related apoptosis inducing ligand (TRAIL), heparinase, bone morphogenic proteins (BMPs), human atrial natriuretic peptide (hANP), glucagon-like peptide (GLPep), Exnatide, Calcitonin (human or salmon), Teriparatide, Coagulation factors, hirudin, Anakinra, renin, bradykinin, bacitracins, polymyxins, colistins, tyrocidine, gramicidins, cyclosporins, neurotensin, tachykinin, neuropeptide Y(NPY), peptide YY (PYY), vasoactive intestinal polypeptide (VIP), pituitray adenylate cyclase-activating polypeptide (PACAP) and synthetic analogues thereof, RGD, Collagen, Fibronectin, Laminin, Vitronectin, Proteoglycan, monoclonal antibody, fusion protein, beta-glucocerebrosidase, Lactase, Alglucosidase-α, alpha-galactosidase A, Lipase, Amylase, Protease, Hyaluronidase, L-asparaginase, and cytokines, the hormone is selected from the group consisting of growth hormone (somatotropin), luteinizing hormone releasing hormone (LHRH), somatostatin, thyrotropin releasing hormone (TRH), adrenocorticotropic hormone), Follicle-stimulating hormone (FSH), Human Chorionic Gonadotropin (HCG), Lutropin-α, testosterone, estradiol, progesterone, prostaglandins, and their synthetic analogues, modified material and material having the same efficacy, the vaccine is selected from the group consisting of hepatitis vaccine, HPV vaccine, and lyme disease vaccine, the gene is selected from the group consisting of small interfernce RNA (siRNA), small hairpin RNA (shRNA), micro RNA (miRNA), aptamer, plasmid DNA and antisense oligodeoxynucleotide (AS-ODN), the anti-cancer drug is selected from the group consisting of paclitaxel, doxorubicin, 5-fluorouracil, cisplatin, carboplatin, oxaliplatin, tegafur, irinotecan, docetaxel, cyclophosphamide, gemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassuim, medroxypogexterone acetate, epirubicin, letrozole, pirarubicin, topotecan, altretamine, toremifene citrate, BCNU, taxotere, actinomycin D, Anasterozole, Belotecan, Imatinib, Floxuridine, Gemcitabine, Hydroxyurea, Zoledronate, Vincristine, Flutamide, Valrubicin, Streptozocin, Silibinin, polyethyleneglycol conjugated anti-cancer drug, and their synthetic analogue, modified material and material having the same efficacy, and the angiogenesis inhibitor is selected from the group consisting of BMS-275291 (Bristol-Myers Squibb, New York), Clodronate, 6-deoxy-6-demethyl-4-dedimethylaminotetracycline (COL-3), Doxycycline, Marimastat, 2-methoxyestradiol, Squalamine, SU5164, Thalidomide, TNP-470, Combretastatin A4, Soy isoflavone, Enzastaurin, CC 5013 (Revimid; Celgene Corp, Warren, N.J.), Celecoxib, ZD 6474 (inhibitor of vascular endotherial growth factor receptor tyrosine kinase, Halofuginone hydrobromide, Interferon-alpha, Bevacizumab, AE-941 (Neovastat), Interleukin-12, vascular endothelial growth factor trap (VEFG-trap), Cetuximab, Rebimastat, matrix metalloprotrease (MMP) inhibitor, Protein kinase C beta inhibitor, Endinhibit, vatalanib (PTK787/ZK 222584), sunitinib malate (SU11248), cilenqitide (EMD-121974), humanized monoclonal antibody MEDI-522, EOS-200-4, integrin-alpha-5-beta-1 antagonist (ATN-161), and their synthetic analogue, modified material and material having the same efficacy.

10. The poly(organophosphazene)-superparamagnetic nanoparticle complex according to claim 7, wherein the complex is
1) a mixed-type where the superparamagnetic ferrite nanoparticle with a hydrophilic surface is physically mixed with the phosphazene-based polymer, or
2) a bound-type where a hydrophobic surfactant on the surface of the superparamagnetic ferrite nanoparticle binds chemically via hydrophobic binding to the ester of hydrophobic amino acid $(NHCH(R^1)CO_2R^2)$ of the phosphazene-based polymer.

11. A hydrogel comprising a solution of poly(organophosphazene)-superparamagnetic nanoparticle complex according to claim 1, and showing a sol-to-gel behavior depending upon the temperature change.

12. The hydrogel according to claim 11, wherein the poly(organophosphazene)-superparamagnetic nanoparticle complex is contained in at least a solvent selected from the group consisting of buffer solution, acidic solution, basic solution, salt solution, water, saline, water for injection at a concentration of 1 to 50 wt %.

13. The hydrogel according to claim 11, wherein the phosphazene-based polymer is represented by Chemical formula 1b or Chemical formula 1c, shows a sol-to-gel behavior depending upon the temperature change, and includes a intramolecular chemical bond formed in the poly(organophosphazene)-superparamagnetic nanoparticle complex or an intermolecular chemical bond formed between the poly(organophosphazene)-superparamagnetic nanoparticle complexes by performing at least one treatment selected from the methods of:
1) UV-radiation;
2) addition of at least an additive selected from the group consisting of a thiol-based crosslinking agent and a vinyl-based crosslinking agent;
3) addition of at least an additive selected from the group consisting of a pH-adjusting agent, a catalyst, and an organic solvent;
4) addition of catalyst; and
5) use of a mixed solution of at least a poly(organophosphazene)-superparamagnetic nanoparticle complex including a thiol group and at least a poly(organophosphazene)-superparamagnetic nanoparticle complex including a vinyl group, as a solution of poly(organophosphazene)-superparamagnetic nanoparticle complex, Chemical formula 1c

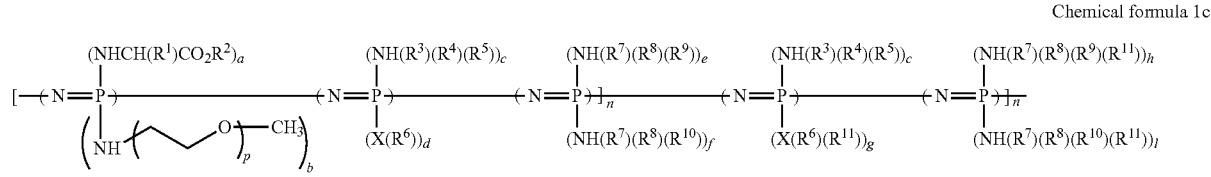

Wherein, p is a numerical value ranging from 7 to 50,
in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_8H_4$, and $R^2$ is selected from the group consisting of $CH_3$, $C_2H_5$, $C_3H_7$, $C_4H_9$, $CH_2C_6H_5$ and $CH_2CHCH_2$,
in the formula $NH(R^3)(R^4)(R^6)$, $R^3$ is $CH(W)$, $R^4$ is selected from the group consisting of $CO_2$, $CONHCH(X)CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_5NH_2$, $C_3H_6NHC(=NH)NH_2$, $CH_2C_3N_2H_3$ and $CH_2SH$,
in formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound,
$NH(R^7)(R^8)(R^9)$ is a substitutent with a functional group where $R^7$ is $CH(Y)$, $R^8$ is selected from the group consisting of $CH_2$, $C_2H_4$, $C_3H_6$, $C_4H_6$, $CH_2C_6H_4$, $CH_2CO_2$, $C_2H_4CO_2$, O, $CONHCH(Z)O$, $CONHCH(Z)CONHCH(M)O$, $CONHCH(Z)CONHCH(N)CONHCH(L)O$, CO, $CO_2$, S, $CONHCH(Z)S$, $CONHCH(Z)CONHCH(M)S$, $CONHCH(Z)CONHCH(M)CONHCH(L)S$, N, $CONHCH(Z)N$, $CONHCH(Z)CONHCH(M)N$, $CONHCH(Z)CONHCH(M)CONHCH(L)N$, CON, $COCHNH(Z)CON$, $COCHNH(Z)CONHCH(M)CON$, $COCHNH(Z)CONHCH(M)CONHCH(L)CON$, $CONHCH(Z)CO$, $COCHNH(Z)CONHCH(M)CO$, $COCHNH(Z)CONHCH(M)CONHCH(L)CO$, $CONHCH(Z)CO_2$, $COCHNH(Z)CONHCH(M)CO_2$, $COCHNH(Z)CONHCH(M)CONHCH(L)CO_2$, $[OCH(CH_3)CO]_q$, $(OCH_2CO)_q$, $[(OCH(CH_3)CO]_q$, $[OCO(CH_2)_8$ CO]$_q$, [OCOC$_6$H$_5$O(CH$_2$)$_8$OC$_6$H$_5$CO]$_q$ and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine and a protecting group of general functional group, Where, Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$ and CH$_2$SH, and q is a number of repeating unit ranging from 1 to 18,000, in the formula, NH(R$^7$)(R$^6$)(R$^{10}$), R$^7$ and R$^8$ are the same substitutents as defined in the NH(R$^7$)(R$^8$)(R$^9$), R$^{10}$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substituent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000;

late-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, NH(R$^7$)(R$^8$)(R$^9$) is a substitutent including a functional group, where, R$^7$ is CH(Y), R$^8$ is selected from the group consisting of CH$_2$, C$_2$H$_4$, C$_3$H$_8$, C$_4$H$_8$, CH$_2$C$_6$H$_4$, CH$_2$CO$_2$, C$_2$H$_4$CO$_2$, O, CONHCH(Z)O, CONHCH(Z)CONHCH(M)O, CONHCH(Z)CONHCH(N)CONHCH(L)O, CO, CO$_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO$_2$, COCHNH(Z)CONHCH(M)CO$_2$, COCHNH(Z)CONHCH(M)CONHCH(L)CO$_2$, [OCH(CH$_3$)CO]$_q$, (OCH$_2$CO)$_q$, [(OCH(CH$_3$)CO]$_q$, [OCO(CH$_2$)$_8$CO]$_q$, [OCOC$_6$H$_5$O(CH$_2$)$_3$OC$_6$H$_5$CO]$_q$, and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH$_2$)H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine, and a general protecting group of a functional group, Chemical formula 1c

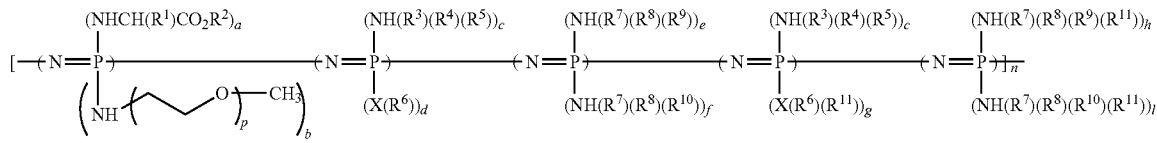

wherein, p is a numerical value ranging of 7 to 50, in group NHCH(R$^1$)CO$_2$R$^2$, R$^1$ is selected from the group consisting of H, CH$_3$, CH$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, and CH$_2$C$_2$NH$_2$C$_6$H$_4$, and R$^2$ is selected from the group consisting of CH$_3$, C$_2$H$_5$, C$_3$H$_7$, C$_4$H$_9$, CH$_2$C$_6$H$_5$, and CH$_2$CHCH$_2$, in group NH(R$^3$)(R$^4$)(R$^5$), R$^3$ is CH(W), R$^4$ is selected from the group consisting of CO$_2$, CONHCH(X)CO$_2$CO$_2$, CH$_2$CO$_2$, and CO$_2$CH(CH$_3$)CO$_2$, and R$^5$ is selected from the group consisting of H, CH$_3$, and C$_2$H$_5$, where W and X are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, in group XR$^6$, X is N or O, R$^6$ is selected from the group consisting of an acrylate-based compound, a metacrywhere Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_8$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_5$NH$_2$, C$_3$H$_6$NHC(=NH)NH$_2$, CH$_2$C$_3$N$_2$H$_3$, and CH$_2$SH, and q represents a number of a repeating unit and ranges from 1 to 18000, R$^{10}$ is a compound including thiol, vinyl, tyramine, tyrosine, or phenol-based compound and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $R^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, a, b, c, d, e, f, g, h and I are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

14. The hydrogel according to claim 13, wherein the chemical bond is formed between the thiol group and the vinyl group by using a mixed solution of at least a poly(organophosphazene)-superparamagnetic nanoparticle complex including a thiol group in $R^6$ and $R^{10}$ and at least a poly(organophosphazene)-superparamagnetic nanoparticle complex including a vinyl group in $R^6$ and $R^{10}$.

15. The hydrogel according to claim 13, wherein the chemical bond is formed by performing UV-radiation with the addition of at least a photoinitiator selected from the group consisting of keton compounds, phosphin oxide compounds, alkylester compounds, benzoyl compounds, titanium salts, iodoinum salts, dibenzoyl compounds, thiocarbonate compounds, dion compounds and potassium salts, in an amount of $1 \times 10^{-6}$ to 10 wt % based on the weight of poly(organophosphazene)-superparamagnetic nanoparticle complex.

16. The hydrogel according to claim 13, wherein the chemical bond is formed between the vinyl group or the thiol group of crosslinking agent and the vinyl group or the thiol group of poly(organophosphazene)-superparamagnetic nanoparticle complex, by adding and reacting at least an additive selected from the group consisting of a thiol-based crosslinking agent and a vinyl-based crosslinking agent, at an amount of $1 \times 10^{-6}$ to 30 wt % based on the weight of poly(organophosphazene)-superparamagnetic nanoparticle complex.

17. The hydrogel according to claim 13, wherein the chemical bond is formed between the phosphazene-based polymer with a thiol group and the phosphazene-based polymer with a vinyl group, or between the phosphazene-based polymers with a thiol group, by adding and reacting at least an additive which is selected from the group consisting of at least a pH-adjusting agent selected from the group consisting of sodium hydroxide, ammonia, potassium hydroxide, triethylamine, sodium phosphate, TRIS base, and 4-(2-hydroxyethyl)-1-piperazineethanesulfonic acid (HEPES); at least a catalyst selected from the group consisting of hydrogen peroxide and ammonium peroxide; and an organic solvent, in an amount of additives of $1 \times 10^{-6}$ to 30 wt % based on the weight of poly(organophosphazene)-superparamagnetic nanoparticle complex.

18. The hydrogel according to claim 13, wherein the chemical bond is formed by reacting the enzyme and tyramine, tyrosine or phenyl derivatives of poly(organophosphazene)-superparamagnetic nanoparticle complex, with the addition of oxidoreductase in an amount of $1 \times 10^{-6}$ to 200 wt % based on the weight of poly(organophosphazene)-superparamagnetic nanoparticle complex.

19. A composition for carrying a physiologically-active material which comprises a hydrogel which comprises a poly(organophosphazene)-superparamagnetic nanoparticle complex of claim 1 or a solution of the poly(organophosphazene)-superparamagnetic nanoparticle complex, and shows a sol-to-gel behavior depending upon the temperature change.

20. The composition according to claim 19, wherein the hydrogel comprises the phosphazene-based polymer represented by Chemical formula 1b or Chemical formula 1c, shows a sol-to-gel behavior depending upon the temperature change, and includes a intramolecular chemical bond formed in the poly(organophosphazene)-superparamagnetic nanoparticle complex or an intermolecular chemical bond formed between the poly(organophosphazene)-superparamagnetic nanoparticle complexes by performing at least one treatment selected from the methods of:

1) UV-radiation;
2) addition of at least an additive selected from the group consisting of a thiol-based crosslinking agent and a vinyl-based crosslinking agent;
3) addition of at least an additive selected from the group consisting of a pH-adjusting agent, a catalyst, and an organic solvent;
4) addition of catalyst; and
5) use of a mixed solution of at least a poly(organophosphazene)-superparamagnetic nanoparticle complex including a thiol group and at least a poly(organophosphazene)-superparamagnetic nanoparticle complex including a vinyl group, as a solution of poly(organophosphazene)-superparamagnetic nanoparticle complex, Chemical formula 1b

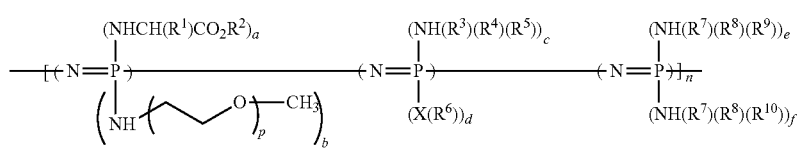

Wherein, p is a numerical value ranging from 7 to 50, in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$ and $CH_2CHCH_2$, in the formula $NH(R^3)(R^4)(R^5)$, $R^3$ is CH(W), $R^4$ is selected from the group consisting of $CO_2$, CONHCH(X)$CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC$(=NH)$NH_2$, $CH_2C_3N_2H_3$ and $CH_2SH$, in formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substituent with a functional group where $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z)CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$ and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, NHCH(SH)$CO_2$H, $NH(CH_2)_qSH$, $NH(CH_2CH_2NH)_qH$, $[NHCH(C_4H_8NH_2)CO]_qOH$, $[NHCH[(CH_2)_3C(=NH)(NH_2)]CO]_qOH$, folic acid, hyaluronic acid, polyhistidine, cyclodextrin, heparin, chitosan, protamine and a protecting group of general functional group, Where, Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, and q is a number of repeating unit ranging from 1 to 18,000, in the formula, $NH(R^7)(R^8)(R^{10})$, $R^7$ and $R^8$ are the same substitutents as defined in the $NH(R^7)(R^6)(R^9)$, $R^{10}$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substitutent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000;

[Chemical formula 1c]

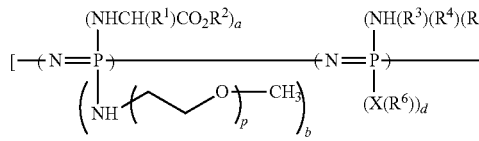 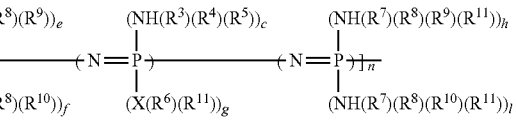

wherein, p is a numerical value ranging of 7 to 50, in group $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$, in group $NH(R^3)(R^4)(R^5)$, $R^3$ is CH(W), $R^4$ is selected from the group consisting of $CO_2$, CONHCH(X)$CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, in group $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substituent including a functional group, where, $R^7$ is CH(Y), $R^8$ is selected from the group consisting of $CH_2$, $C_2H_4$, $C_3H_8$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z)CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$, and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_8H_5$, $CH_2CHCH_2$, $NHCH(SH)CO_2H$, $NH(CH_2)_q$ SH, $NH(CH_2CH_2NH)_qH$, $[NHCH(C_4H_8NH_2)CO]_q$ OH, $[NHCH[(CH_2)_3C(=NH)(NH_2)]CO]_qOH$, folic acid, hyaluronic acid, polyhistidine, cyclodextrin, heparin, chitosan, protamine, and a general protecting group of a functional group, where Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2CH_4OH$, $CH_2COOH$, $CH_2CH_2COOH$, $CH_2CONH_2$, $C_4H_6NH_2$, $C_3H_6NHC(=NH)NH_2$, $CH_2C_3N_2H_3$, and $CH_2SH$, and q represents a number of a repeating unit and ranges from 1 to 18000, $R^{10}$ is a compound including thiol, vinyl, tyramine, tyrosine, or phenol-based compound, and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $R^{11}$ is at least a bioactive substance selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, a, b, c, d, e, f, g, h and I are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

21. A carrier for physiologically-active material comprising a hydrogel which comprises a poly(organophosphazene)-superparamagnetic nanoparticle complex of claim 1 or a solution of the poly(organophosphazene)-superparamagnetic nanoparticle complex, and shows a sol-to-gel behavior depending upon the temperature change; and at least a physiologically-active material selected from the group consisting of protein, polypeptide, peptide, vaccine, gene, hormone, anti-cancer drug, angiogenesis inhibitor, and therapeutic cell.

22. The carrier for physiologically-active material according to claim 21, wherein the hydrogel comprises the phosphazene-based polymer represented by Chemical formula 1 b or Chemical formula 1c, shows a sol-to-gel behavior depending upon the temperature change, and includes a intramolecular chemical bond formed in the poly(organophosphazene)-superparamagnetic nanoparticle complex or an intermolecular chemical bond formed between the poly(organophosphazene)-superparamagnetic nanoparticle complexes by performing at least one treatment selected from the methods of:

1) UV-radiation;
2) addition of at least an additive selected from the group consisting of a thiol-based crosslinking agent and a vinyl-based crosslinking agent;
3) addition of at least an additive selected from the group consisting of a pH-adjusting agent, a catalyst, and an organic solvent;
4) addition of catalyst; and
5) use of a mixed solution of at least a poly(organophosphazene)-superparamagnetic nanoparticle complex including a thiol group and at least a poly(organophosphazene)-superparamagnetic nanoparticle complex including a vinyl group, as a solution of poly(organophosphazene)-superparamagnetic nanoparticle complex, Chemical formula 1b

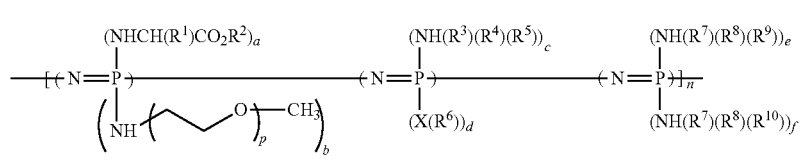

Wherein, p is a numerical value ranging from 7 to 50, in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$ and $CH_2CHCH_2$, in the formula $NH(R^3)(R^4)(R^5)$, $R^3$ is CH(W), $R^4$ is selected from the group consisting of $CO_2$, $CONHCH(X)CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, in formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substitutent with a functional group where $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, $CONHCH(Z)O$, $CONHCH(Z)CONHCH(M)O$, $CONHCH(Z)CONHCH(N)CONHCH(L)O$, CO, $CO_2$, S, $CONHCH(Z)S$, $CONHCH(Z)CONHCH$ (M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO$_2$, COCHNH(Z)CONHCH(M)CO$_2$, COCHNH(Z)CONHCH(M)CONHCH(L)CO$_2$, [OCH(CH$_3$)CO]$_q$, (OCH$_2$CO)$_q$, [(OCH(CH$_3$)CO]$_q$, [OCO(CH$_2$)CO]$_q$, [OCOC$_6$H$_5$O(CH$_2$)$_3$OC$_6$H$_5$CO]$_q$ and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine and a protecting group of general functional group, Where, Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$ and CH$_2$SH, and q is a number of repeating unit ranging from 1 to 18,000, in the formula, NH(R$^7$)(R$^8$)(R$^{10}$), R$^7$ and R$^8$ are the same substitutents as defined in the NH(R$^7$)(R$^8$)(R$^9$), R$^{10}$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substitutent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000;

selected from the group consisting of H, CH$_3$, and C$_2$H$_5$, where W and X are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, in group XR$^6$, X is N or O, R$^8$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, NH(R$^7$)(R$^6$)(R$^9$) is a substitutent including a functional group, where, R$^7$ is CH(Y), R$^8$ is selected from the group consisting of CH$_2$, C$_2$H$_4$, C$_3$H$_6$, C$_4$H$_6$, CH$_2$C$_6$H$_4$, CH$_2$CO$_2$, C$_2$H$_4$CO$_2$, O, CONHCH(Z)O, CONHCH(Z)CONHCH(M)O, CONHCH(Z)CONHCH(N)CONHCH(L)O, CO, CO$_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO$_2$, COCHNH(Z)CONHCH(M)CO$_2$, COCHNH(Z)CONHCH(M)CONHCH(L)CO$_2$, [OCH(CH$_3$)CO]$_q$, (OCH$_2$CO)$_q$, [(OCH(CH$_3$)CO]$_q$, [OCO(CH$_2$)CO]$_q$, [OCOC$_6$H$_5$O(CH$_2$)$_3$OC$_6$H$_5$CO]$_q$, and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine, and a general protecting group of a functional group,

[Chemical formula 1c]

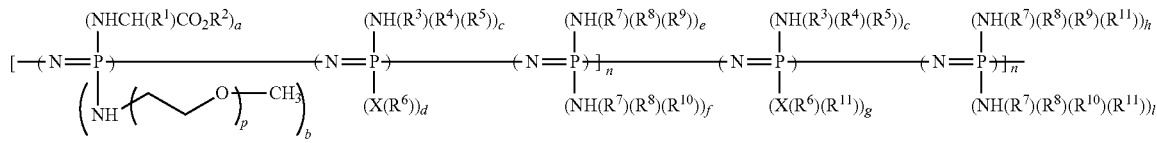

wherein, p is a numerical value ranging of 7 to 50, in group NHCH(R$^1$)CO$_2$R$^2$, R$^1$ is selected from the group consisting of H, CH$_3$, CH$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, and CH$_2$C$_2$NH$_2$C$_6$H$_4$, and R$^2$ is selected from the group consisting of CH$_3$, C$_2$H$_5$, C$_3$H$_7$, C$_4$H$_9$, CH$_2$C$_6$H$_5$, and CH$_2$CHCH$_2$, in group NH(R$^3$)(R$^4$)(R$^5$), R$^3$ is CH(W), R$^4$ is selected from the group consisting of CO$_2$, CONHCH(X)CO$_2$CO$_2$, CH$_2$CO$_2$, and CO$_2$CH(CH$_3$)CO$_2$, and R$^5$ is where Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, and q represents a number of a repeating unit and ranges from 1 to 18000, R$^{10}$ is a compound including thiol, vinyl, tyramine, tyrosine, or phenol-based compound, and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $R^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, a, b, c, d, e, f, g, h and I are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

23. The carrier for physiologically-active material according to claim 21, wherein the physiologically-active material is contained in the carrier at an amount of $1 \times 10^{-8}$ to 50 vol % based on the total volume of composition.

24. A biomaterial comprising a hydrogel which comprises a poly(organophosphazene)-superparamagnetic nanoparticle complex of claim 1 or a solution of the poly(organophosphazene)-superparamagnetic nanoparticle complex, and shows a sol-to-gel behavior depending upon the temperature change.

25. The biomaterial according to claim 24, wherein the hydrogel comprises the phosphazene-based polymer represented by Chemical formula 1b or Chemical formula 1c, shows a sol-to-gel behavior depending upon the temperature change, and includes a intramolecular chemical bond formed in the poly(organophosphazene)-superparamagnetic nanoparticle complex or an intermolecular chemical bond formed between the poly(organophosphazene)-superparamagnetic nanoparticle complexes by performing at least one treatment selected from the methods of:

1) UV-radiation;
2) addition of at least an additive selected from the group consisting of a thiol-based crosslinking agent and a vinyl-based crosslinking agent;
3) addition of at least an additive selected from the group consisting of a pH-adjusting agent, a catalyst, and an organic solvent;
4) addition of catalyst; and 5) use of a mixed solution of at least a poly(organophosphazene)-superparamagnetic nanoparticle complex including a thiol group and at least a poly(organophosphazene)-superparamagnetic nanoparticle complex including a vinyl group, as a solution of poly(organophosphazene)-superparamagnetic nanoparticle complex, Chemical formula 1b

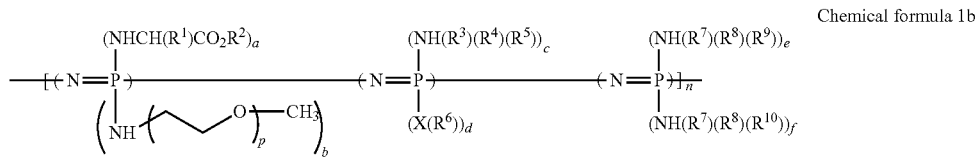

Wherein, p is a numerical value ranging from 7 to 50, in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$ and $CH_2CHCH_2$, in the formula $NH(R^3)(R^4)(R^5)$, $R^3$ is CH(W), $R^4$ is selected from the group consisting of $CO_2$, CONHCH$(X)CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4HNH_2$, $C_3H_6NHC(=NH)NH_2$, $CH_2C_3N_2H_3$ and $CH_2SH$, in formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substitutent with a functional group where $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO_2, COCHNH(Z)CONHCH(M)CO_2, COCHNH(Z)CONHCH(M)CONHCH(L)CO_2, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$ and

[OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine and a protecting group of general functional group, Where, Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_6$NH$_2$, C$_3$H$_6$NHC(=NH)NH$_2$, CH$_2$C$_3$N$_2$H$_3$ and CH$_2$SH, and q is a number of repeating unit ranging from 1 to 18,000, in the formula, NH(R$^7$)(R$^6$)(R$^{10}$), R$^7$ and R$^8$ are the same substitutents as defined in the NH(R$^7$)(R$^8$)(R$^9$), R$^{10}$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substitutent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000;

a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, NH(R$^7$)(R$^8$)(R$^9$) is a substitutent including a functional group, where, R$^7$ is CH(Y), R$^6$ is selected from the group consisting of CH$_2$, C$_2$H$_4$, C$_3$H$_6$, C$_4$H$_8$, CH$_2$C$_6$H$_4$, CH$_2$CO$_2$, C$_2$H$_4$CO$_2$, O, CONHCH(Z)O, CONHCH(Z)CONHCH(M)O, CONHCH(Z)CONHCH(N)CONHCH(L)O, CO, CO$_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO$_2$, COCHNH(Z)CONHCH(M)CO$_2$, COCHNH(Z)CONHCH(M)CONHCH(L)CO$_2$, [OCH(CH$_3$)CO]$_q$, (OCH$_2$CO)$_q$, [(OCH(CH$_3$)CO]$_q$, [OCO(CH$_2$)$_8$CO]$_q$, [OCOC$_6$H$_5$O(CH$_2$)$_3$OC$_6$H$_5$CO]$_q$, and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine, and a general protecting group of a functional group,

[Chemical formula 1c]

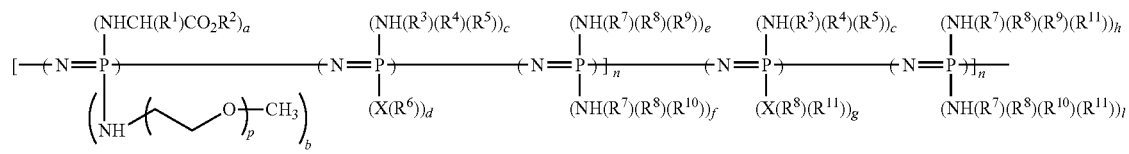

wherein, p is a numerical value ranging of 7 to 50, in group NHCH(R$^1$)CO$_2$R$^2$, R$^1$ is selected from the group consisting of H, CH$_3$, CH$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, and CH$_2$C$_2$NH$_2$C$_6$H$_4$, and R$^2$ is selected from the group consisting of CH$_3$, C$_2$H$_5$, C$_3$H$_7$, C$_4$H$_9$, CH$_2$C$_6$H$_5$, and CH$_2$CHCH$_2$, in group NH(R$^3$)(R$^4$)(R$^5$), R$^3$ is CH(W), R$^4$ is selected from the group consisting of CO$_2$, CONHCH(X)CO$_2$CO$_2$, CH$_2$CO$_2$, and CO$_2$CH(CH$_3$)CO$_2$, and R$^5$ is selected from the group consisting of H, CH$_3$, and C$_2$H$_5$, where W and X are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$HNH$_2$, C$_3$H$_6$NHC(=NH)NH$_2$, CH$_2$C$_3$N$_2$H$_3$, and CH$_2$SH, in group XR$^6$, X is N or O, R$^6$ is selected from the group consisting of an acrylate-based compound, a metacrylate-based compound, an acrylamide-based compound, where Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, and q represents a number of a repeating unit and ranges from 1 to 18000, R$^{10}$ is a compound including thiol, vinyl, tyramine, tyrosine, or phenol-based compound and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, R$^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, a, b, c, d, e, f, g, h and I are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

26. The bio-material according to claim 24, wherein the bio-material is selected from the group consisting of a bio-material for plastic surgery and orthopedic surgery, a bio-material for tissue engineering, a dental bio-material, a bio-material for preventing vascular adhesion, and a bio-material used for vascular occlusion.

27. The bio-material according to claim 26, wherein the bio-material for plastic surgery and orthopedic surgery is filler, the bio-material for tissue engineering is an artificial cartilage, and the bio-material for preventing vascular adhesion is a stent.

28. The bio-material according to claim 24, wherein the bio-material is used for treatment of cancer hyperthermia.

29. A contrast agent of magnetic resonance image (MRI) used for intravenous injection, comprising a hydrogel which comprises a poly(organophosphazene)-superparamagnetic nanoparticle complex of claim 1 or a solution of the poly(organophosphazene)-superparamagnetic nanoparticle complex, and shows a sol-to-gel behavior depending upon the temperature change.

30. The contrast agent for MRI according to claim 29, wherein the hydrogel comprises the phosphazene-based polymer represented by Chemical formula 1b or Chemical formula 1c, shows a sol-to-gel behavior depending upon the temperature change, and includes a intramolecular chemical bond formed in the poly(organophosphazene)-superparamagnetic nanoparticle complex or an intermolecular chemical bond formed between the poly(organophosphazene)-superparamagnetic nanoparticle complexes by performing at least one treatment selected from the methods of:
 1) UV-radiation;
 2) addition of at least an additive selected from the group consisting of a thiol-based crosslinking agent and a vinyl-based crosslinking agent;
 3) addition of at least an additive selected from the group consisting of a pH-adjusting agent, a catalyst, and an organic solvent;
 4) addition of catalyst; and
 5) use of a mixed solution of at least a poly(organophosphazene)-superparamagnetic nanoparticle complex including a thiol group and at least a poly(organophosphazene)-superparamagnetic nanoparticle complex including a vinyl group, as a solution of poly(organophosphazene)-superparamagnetic nanoparticle complex, Wherein, p is a numerical value ranging from 7 to 50, in the formula $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$ and $CH_2CHCH_2$, in the formula $NH(R^3)(R^4)(R^5)$, $R^3$ is $CH(W)$, $R^4$ is selected from the group consisting of $CO_2$, $CONHCH(X)CO_2CO_2$, $CH_2CO_2$ and $CO_2CH(CH_3)CO_2$, $R^5$ is selected from the group consisting of H, $CH_3$ and $C_2H_5$, W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_6NH_2$, $C_3H_5NHC(=NH)NH_2$, $CH_2C_3N_2H_3$ and $CH_2SH$, in formula $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substitutent with a functional group where $R^7$ is $CH(Y)$, $R^8$ is selected from the group consisting of $CH_2$, $C_2H_4$, $C_3H_6$, $C_4He$, $CH_2C_6H_4$, $CH_2CO_2$, $C_2H_4CO_2$, O, $CONHCH(Z)O$, $CONHCH(Z)CONHCH(M)O$, $CONHCH(Z)CONHCH(N)CONHCH(L)O$, CO, $CO_2$, S, $CONHCH(Z)S$, $CONHCH(Z)CONHCH(M)S$, $CONHCH(Z)CONHCH(M)CONHCH(L)S$, N, $CONHCH(Z)N$, $CONHCH(Z)CONHCH(M)N$, $CONHCH(Z)CONHCH(M)CONHCH(L)N$, CON, $COCHNH(Z)CON$, $COCHNH(Z)CONHCH(M)CON$, $COCHNH(Z)CONHCH(M)CONHCH(L)CON$, $CONHCH(Z)CO$, $COCHNH(Z)CONHCH(M)CO$, $COCHNH(Z)CONHCH(M)CONHCH(L)CO$, $CONHCH(Z)CO_2$, $COCHNH(Z)CONHCH(M)CO_2$, $COCHNH(Z)CONHCH(M)CONHCH(L)CO_2$, $[OCH(CH_3)CO]_q$, $(OCH_2CO)_q$, $[(OCH(CH_3)CO]_q$, $[OCO(CH_2)_6CO]_q$, $[OCOC_6H_5O(CH_2)_3OC_6H_5CO]_q$ and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_qH$, $[NHCH(C_4H_8NH_2)CO]_qOH$, $[NHCH[(CH_2)_3C(=NH)(NH_2)]CO]_qOH$, folic acid, hyaluronic acid, polyhistidine, cyclodextrin, heparin, chitosan, protamine and a protecting group of general functional group, Where, Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, Chemical formula 1b

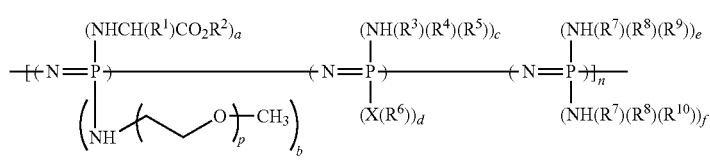

$CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$ and $CH_2SH$, and q is a number of repeating unit ranging from 1 to 18,000, in the formula, $NH(R^7)(R^8)(R^{10})$, $R^7$ and $R^8$ are the same substitutents as defined in the $NH(R^7)(R^8)(R^9)$, $R^{10}$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e and f represent the content of each substituent, each a and b is 0.01 to 1.9, each c, d, e, and f is 0 to 1.9, d and f are not zero simultaneously, a+b+c+d+e+f=2.0, and n is a polymerization degree of phosphazen-based polymer ranging from 5 to 100,000;

CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)$CO_2$, COCHNH(Z)CONHCH(M)$CO_2$, COCHNH(Z)CONHCH(M)CONHCH(L)$CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$, and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_qH$, $[NHCH(C_4H_5NH_2)CO]_qOH$, $[NHCH[(CH_2)_3C(=NH)(NH_2)]CO]_qOH$, folic acid, hyaluronic acid, polyhistidine, cyclodextrin, heparin, chitosan, protamine, and a general protecting group of a functional group, where Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$,

[Chemical formula 1c]

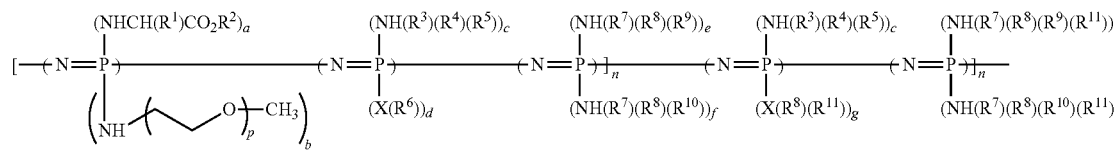

wherein, p is a numerical value ranging of 7 to 50, in group $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_5$, $CH_2O CH_5$, and $CH_2CHCH_2$, in group $NH(R^3)(R^4)(R^5)$, $R^3$ is CH(W), $R^4$ is selected from the group consisting of $CO_2$, CONHCH(X)$CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, in group $XR^6$, X is N or O, $R^6$ is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substitutent including a functional group, where, $R^7$ is CH(Y), $R^8$ is selected from the group consisting of $CH_2$, $C_2H_4$, $C_3H_6$, $C_4H_8$, $CH_2CH_4$, $CH_2CO_2$, $C_2H_4CO_2$, O, CONHCH(Z)O, CONHCH(Z)

$CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, and q represents a number of a repeating unit and ranges from 1 to 18000, $R^{10}$ is a compound including thiol, vinyl, tyramine, tyrosine, or phenol-based compound, and is selected from the group consisting of an acrylate-based compound, a metacrylate-based compound, an acrylamide-based compound, a vinylsulfone-based compound, a thiol-based compound, a cysteine-based compound, a cisteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $R^{11}$ is at least a physiologically-active material selected from the group consisting of protein, polypeptide, peptide, fusion protein, antibody, hormone, vaccine, gene, anti-cancer drug, and angiogenesis inhibitor which include at least a functional group selected from the group consisting of hydroxyl, amide, amino, carboxyl, thiol, vinyl, aldehyde, halogen, and keton group, a, b, c, d, e, f, g, h and I are the content of each substitutents, each a and b is 0.01 to 1.9, each c, d, e, f, g, h, and i is 0 to 1.9, d and f are not zero simultaneously, g, h and i are not zero simultaneously, and a+b+c+d+e+f+g+h+i=2.0, and n represents a polymerization degree of polyphosphazene and ranges 5 to 100,000.

* * * * *